US006218179B1

(12) United States Patent
Webster et al.

(10) Patent No.: US 6,218,179 B1
(45) Date of Patent: *Apr. 17, 2001

(54) TISSUE SPECIFIC HYPOXIA REGULATED CONSTRUCTS

(75) Inventors: Keith A. Webster; Nanette H. Bishopric, both of Key Biscayne, FL (US); Brian Murphy, Palo Alto; Keith R. Laderoute, Menlo Park; Christopher J. Green, Novato, all of CA (US)

(73) Assignee: SRI International, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/880,342

(22) Filed: Jun. 23, 1997

Related U.S. Application Data

(63) Continuation-in-part of application No. 08/365,486, filed on Dec. 23, 1994, and a continuation of application No. PCT/IB95/00996, filed on Nov. 13, 1995.

(51) Int. Cl.$^7$ .................................................. C12N 15/85

(52) U.S. Cl. ...................... 435/320.1; 435/325; 435/455; 536/23.1; 536/24.1; 935/22; 935/36

(58) Field of Search .................... 435/325, 455, 435/320.1; 536/23.1, 23.5, 24.1; 514/44; 424/93.1

(56) References Cited

U.S. PATENT DOCUMENTS 5,834,306 * 11/1998 Webster et al. .................... 435/320.1

FOREIGN PATENT DOCUMENTS

PCT/US91/01280   2/1991 (WO).

OTHER PUBLICATIONS

Friedmann, Gene Therapy 1:217–218, 1994.*
Mulligan, Science 260:925–932, 1993.*
Lewis et al J.Virol. 68(1):510–516, 1994.*
Finkel et al, FASEB J. 9: 843–851, 1995.*
Blu et al N Engl J Med. 333(18):1204–7. 1995.*
Semenza et al Mol Cell. Bio. 12:12, pp. 5447–5454, 1992.*
Karin et al Nature 299:5886, pp. 797–802, 1982.*
Beck, I., et al., Characterization of Hypoxia–Responsive Enhancer in the Human Erythropoietin Gene Shows Presence of Hypoxia–Inducible 120–Kd Nuclear DNA–Binding Protein in Erythropoietin–Producing and Nonproducing Cells,: *Blood* 82(3):704–711 (1993).
Berr et al., "Stable Delivery of Physiologic Levels of Recombinant Erythropoietin to the Systemic Circulation by Intramuscular Injection of Replication–Defective Adenovirus", *Basic Science* (1994) 90(4):1–3.

Blanchard et al., "Hypoxic Induction of the Human Erythropoietin Gene: Cooperation between the Promoter and Enhancer, Each of Which Contains Steroid Receptor Response Elements" *Molecular and Cellular Biology* (1992) 12(12):5373.
Bredt et al., "Cloned and expressed nitric oxide synthase structurally resembles cytochrome P–450 reductase" *Nature* (1991) 351:714.
Culver, et al., "Gene Therapy for Cancer," *TIG* 10(5):174–178 (1994).
Doria–Medina et al., "Immunolocalization of GLUT–1 glucose transporter in rat skeletal muscle and in normal and hypoxic cardiac tissue" *American Journal of Physiology* (1993) 265:E454.
Firth, J.D., et al., "Oxygen–Regulated Control Elements in the Phosphoglycerate Kinase 1 and Lactate Dehydronase A Genes: Similarities with the Erythropoietin 3' Enhancer," *Proc. Nat'l. Acad. Sci. USA* 91:6496–6500 (1994).
Franz et al., "Heart–Specific Targeting of Firefly Luciferase by the Myosin Light Chain–2 Promoter and Developmental Regulation in Transgenic Mice" *Circulation Research* (1993) 73:629.
Gordon et al., "Expression of Neural Cell Adhesion Molecule Immunoreactivity in Hypertrophic Myocardium" *Life Sciences* (1990) 47:601.
Hodgson, "Advances in Vector Systems for Gene Therapy," *Exp. Opin. Ther. Pat.* 5(5):459–468 (1995).
Kourembanas et al., "Nitric Oxide Regulates the Expression of Vasoconstrictors and Growth Factors by Vascular Endothelium under both Normoxia and Hypoxia" *J. Clin. Invest.* (1993) 92:99.
Ladoux et al., "Hypoxia is a Strong Inducer of Vascular Endothelial Growth Factor mRNA expression in the Heart" *Academic Press* (1993) 195(2):1005.
Lafont, et al., "Which Gene for Which Restenosis," *The Lancet* 346:1442–1443 (1995).
Madan et al., "A 24–base–pair sequence 3't the human erythropoietin gene contains a hypoxia–responsive transcriptional enhancer" *Proc. Natl. Acad. Sci USA* (1993) 90:3928.
Marshall, E., "Gene Therapy's Growing Pains," *Science* 269:1050–1055 (Aug. 25, 1995).

(List continued on next page.)

*Primary Examiner*—John L. LeGuyader
*Assistant Examiner*—Sumesh Kaushal
(74) *Attorney, Agent, or Firm*—Carol L. Francis; Bozicevic, Field & Francis LLP

(57) ABSTRACT

Methods and compositions relating to chimeric genes containing (i) a tissue-specific promoter and (ii) a hypoxia response enhancer element, both of which are operably linked to a selected gene, such as a reporter gene, therapeutic gene (e.g., bcl-2, NOS, catalase and SOD), or deleterious gene are disclosed. Expression of the selected gene is enhanced in the target tissue under hypoxia conditions, such as conditions encountered during episodes of ischemia and reperfusion. The methods and compositions may be used as therapeutics and/or diagnostics.

33 Claims, 10 Drawing Sheets

OTHER PUBLICATIONS

Maxwell et al., "Inducible operation of the erythropoietin 3' enhancer in multiple cell lines: Evidence for a widespread oxygen–sensing mechanism" *Proc. Natl. Acad. Sci. USA* (1993) 90:2423.

Metzger et al., "Skeletal troponin C reduces contractile sensitivity to acidosis in cardiac myocytes from transgenic mice" *Proc. Natl. Acad. Sci. USA* (1993) 90:9036.

Milano et al., "Enhanced Myocardial Function in Transgenic Mice Overexpressing the $\beta_2$–Adrenergic Receptor" *Science* (1994) 264:582.

Miller, et al., "Targeted Vectors for Gene Therapy," *FASEB Journal* 9:190–199 (1995).

Minchenko, A., et al., "Hypoxia–Regulatory Elements of the Human Vascular Endothelial Growth Factor Gene," *Cellular and Molecular Biology Research* 40(1):35–39 (1994).

Murphy, B.J., et al., "Metallothionein IIA is Up–Regulated by Hypoxia in Human A431 Squamos Carcinoma Cells," *Cancer Research* 54:5808–5810 (1994).

Murphy, B.J., et al., "Metallothionein IIA is Up–Regulated by Hypoxia in Human A431 Squamos Carcinoma Cells," *FASEB Journal* 8(4–5):A128 (1994).

Prentice, et al., *Circulation* 88:(4 part 2), I475 (1993).

Semenza et al., "A Nuclear Factor Induced by Hypoxia via De Nova Protein Synthesis Binds to the Human Erythropoietin Gene Enhancer at a Site Required for Transcriptional Activation" *Molecular and Cellular Biology* (1992) 12(12):5447.

Semenza et al., "Hypoxia–inducible nuclear factors bind to an enhancer element located 3' to the human erythropoietin gene" *Proc. Natl. Acad. Sci. USA* (1991) 88:5680.

Subramaniam et al., "Transgenic Analysis of the Thyroid–responsive Elements in the $\alpha$–Cardiac Myosin Heavy Chain Gene Promoter" *The Journal of Biological Chemistry* (1993) 268(6):4331.

Tsuchiya et al., "Erythropoietin 5'–Flanking Sequence–Binding Protein Induced during Hypoxia and Cobalt Exposure" *J. Biochem.* (1993) 113(3):395.

Wang, G.L., et al., "General Involvement of Hypoxia–Inducible Factor 1 in Transcriptional Response to Hypoxia," *Proc. Nat'l. Acad. Sci. USA* 90:4304–4308 (1993).

Webster, et al., "Induction and Nuclear Accumulation of Fos and Jun Proto–oncogenes in Hypoxic Cardiac Myocytes" *The Journal of Biological Chemistry* (1993) 268(22)b:16852.

NIH "Report and Recommendations," (Dec. 7, 1995) 1–40.

Haslinger et al., "Upsteam Promoter Element of the Human Metallothionein–II$_A$ Gene Can Act Like an Enhancer Element," *Proc. Natl. Acad. Sci. USA,* (Dec. 1985), vol. 82(24):8572–8576.

Heguy, et al., "Structure and Tissue–Specific Expression of the Human Metallothionein I$_B$ Gene," *Molecular and Cellular Biology,* (Jun. 1986), vol. 6(6):2149–2157.

Karin, et al., "Characterization of DNA Sequences Through Which Cadmium and Glucocorticoid Hormones Induce Human Metallothionein–II$_A$ Gene," *Nature,* (Apr. 1984), vol. 308(5959):513–519.

Karin, et al., "Transcriptional Control Mechanisms Which Regulate The Expression of Human Metallothionein Genes," *Metallothionein II–Experientia Supplementum,* (1987), vol. 52:401–405.

Karin, et al., "Metal–Responsive Elements Act as Positive Modulators of Human Metallothionein–II$_A$ Enhancer Activity," *Molecular and Cellular Biology,* (Feb. 1997) vol. 7(2):606–613.

Lee, et al., "Activation of Transcription by Two Factors That Bind Promoter and Enhancer Sequences of the Human Metallothionein Gene and SV40," *Nature* (Jan. 1987), vol. 325(6102):368–372.

Losordo et al. "Gene Therapy for Myocardial Angiogenesis: Initial Clinical Results With Direct Myocardial Injection of phVEGF$_{165}$ As Sole Therapy for Myocardial Ischemia," *Circulation,* (Dec. 1998), vol. 98(25):2800–2804.

Prentice et al. "Regulated Expression of a Foreign Gene Targeted to the Ischaemic Myocardium," *Cardiovascular Research,* (1997) vol. 35(3):567–574.

Tsurumi et al., "Direct Intramuscular Gene Transfer of Naked DNA Encoding Vascular Endothelial Growth Factor Augments Collateral Development and Tissue Perfusion," *Circulation,* (Dec. 1996), vol. 94(12):3281–3290.

\* cited by examiner

To Fig. 6C

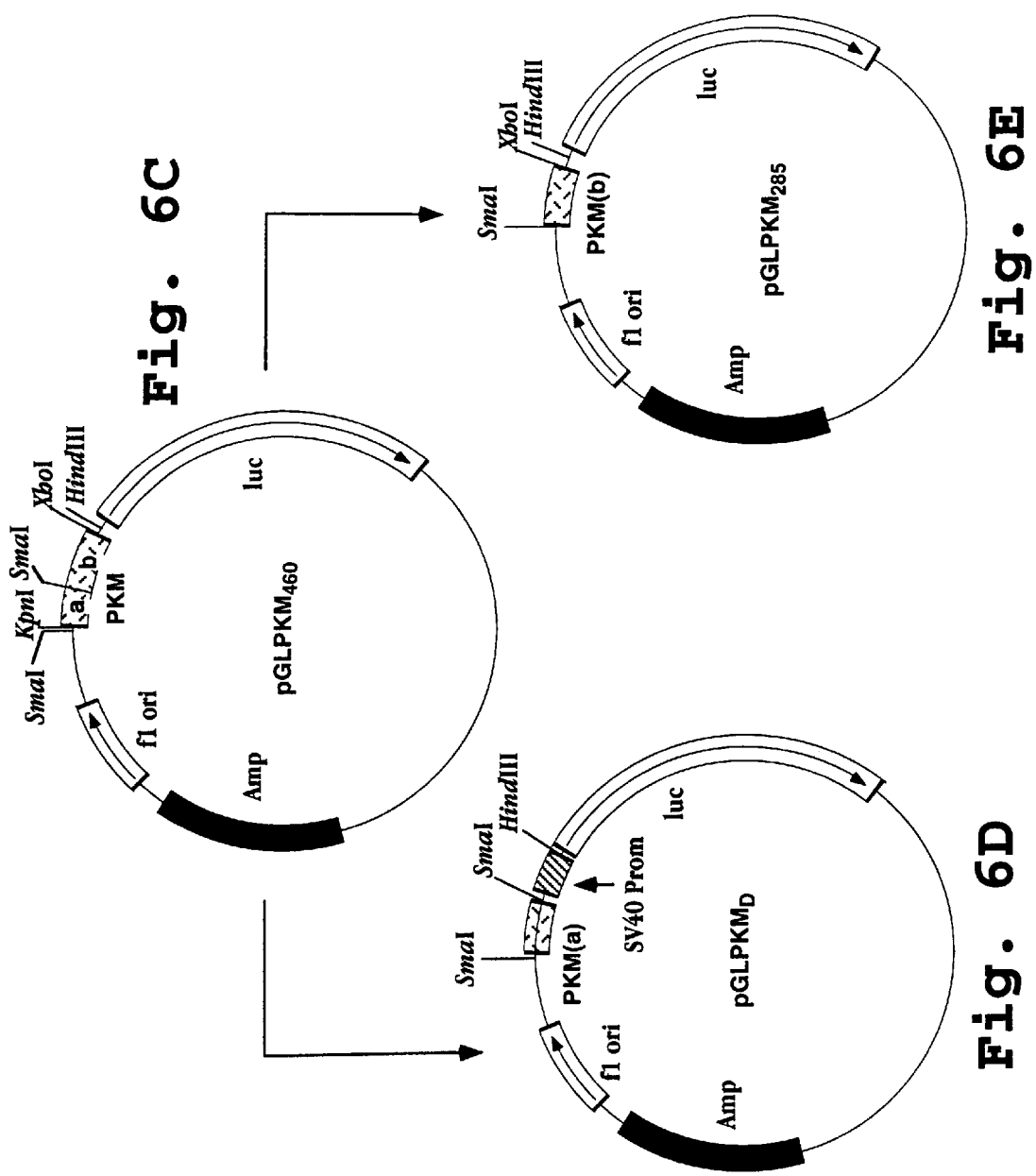

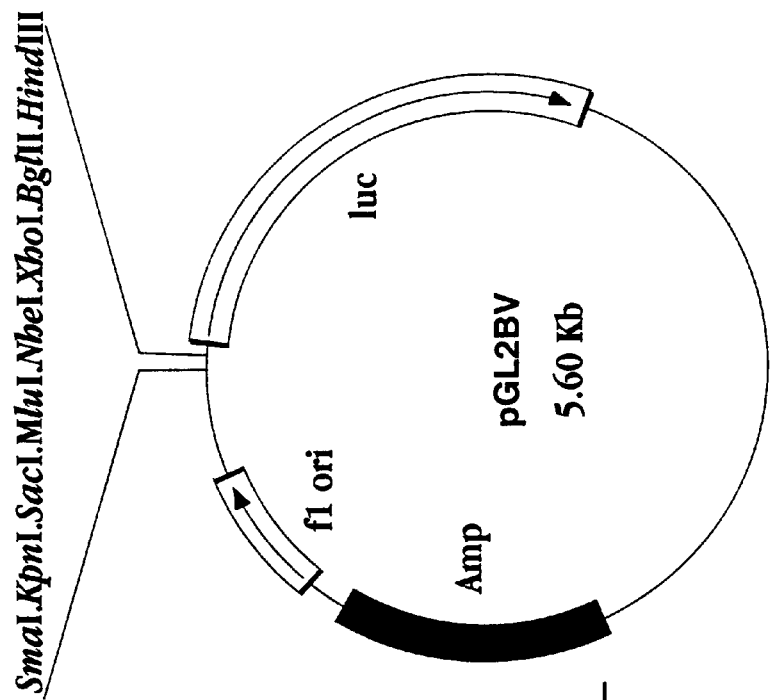
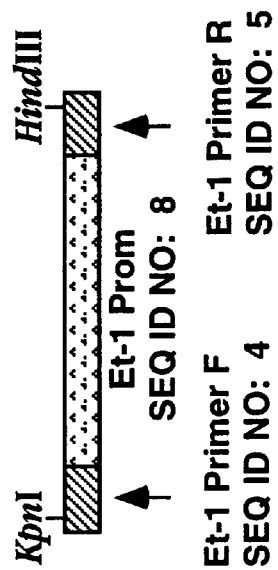
Fig. 7B
Fig. 7A

TISSUE SPECIFIC HYPOXIA REGULATED CONSTRUCTS

This application is a continuation-in-part of U.S. patent application Ser. No. 08/365,486 filed Dec. 23, 1994, now U.S. Pat. No. 5,834,306 and a continuation of PCT Patent Application No. PCT/IB95/00996, filed Nov. 13, 1995, and both of which are incorporated herein by reference.

FIELD OF THE INVENTION

This invention relates to chimeric genes (e.g., carried on expression vectors) containing therapeutic genes whose expression is under the control of tissue specific and hypoxia response enhancer elements.

REFERENCES

Ascadi, G., et al., *New Biology* 3:71 (1991a).
Ascadi, G., et al., *Nature* 352:815 (1991b).
Atkins, C. E., et al., *J. Am. Vet. Med. Assoc.* 201:613–618 (1992).
Ausubel, F. M., et al., *CURRENT PROTOCOLS IN MOLECULAR BIOLOGY*, John Wiley and Sons, Inc., Media Pa. (1992).
Berkner, K. L., *BioTechniques* 6:616 (1988).
Bisphopric, et al., *J. Clin. Invest.* 80:1194 (1987).
Breakefield, X. O., and DeLuca, N. A., *New Biol.* 3:230 (1992).
Bredt, D. S., et al., *Nature* 351:714–718 (1991).
Buttrick, P. M., et al., *Circ. Res.* 70:193–198 (1992).
Buttrick, P. M., et al., *Circ. Res.* 72:1211–1217 (1993).
Chatterjee, J., et al., *Science* 258:1485 (1992).
Chomczynski, P., and Sacchi, N., *Anal. Biochem.* 162:156–159 (1987).
Christiano, R. J., et al., *Proc. Natl. Acad. Sci. U.S.A.* 90:212 (1993).
Clair, D. K. S., et al., *Cancer Res.*, 51:939 (1991).
Cleveland, J. L., and Ihle, J. N., *Cell* 81:479–482 (1995).
Dabareiner, R. M., et al., *Am. J. Vet. Res.* 54:1683–1692 (1993).
Dayhoff, M. O., *ATLAS OF PROTEIN SEQUENCE AND STRUCTURE*, suppl. 3, National Biomedical Research Foundation, Washington, D.C. (1978).
Doolittle, R. F., *OF URFs AND ORFs*, University Science Books (1986).
Flugelman, et al., *Circulation* 82:2217 (1990).
Fox, P. R., et al., *Am. J. Vet. Res.* 54:563–569 (1993).
Franz, W.-M., et al., *Circ. Res.* 73:629 (1993).
Freese, A., et al., *Biochem. Pharm.* 40:2189 (1990).
Frei, B., *Am. J. Med.* 97 suppl 3A:5s–13s (1993)
Friedman, J. M., et al., *Mol. Cell Biol.* 6:3791–3797 (1986).
Fujisawa, H., et al., *J. Neurochem.* 63:140 (1994).
Fukamizu, A., et al., *Biochem. Biophys. Res. Commun.* 199:183 (1994).
Giallongo, A., et al., *Eur. J. Biochem.* 214:367 (1993).
Gorechi, et al., *Free Radic. Res. Commun.* 12–13:401 (1991).
Gottlieb, R. A., et al., *J. Clin. Invest.*, 94:1612–1628 (1994).
Graham, F. L., and Prevea, L., in *METHODS IN MOLECULAR BIOLOGY, Vol. 7* (Murray, E. J., Ed.) Humana, Clifton, N.J., pp. 109–127 (1991).
Grunhaus, A., and Horowitz, M. S., *Semin. Virol.*, 3:237–252 (1992).
Gulick, J., et al., *J. Biol. Chem.* 266:9180–85 (1991).
Gustafson, T. A., et al., *Proc. Natl. Acad. Sci. U.S.A.* 84:3122–3126 (1987).
Hansen, P. R., and Stawaski, G., *Cardiovasc. Res.*, 28:565–569 (1994).
Heakock, C. S., and Sutherland, R. M., *Br. J. Cancer* 62:217–228 (1990).
Hertz, J., and Gerard, R. D., *Proc. Natl. Acad. Sci. U.S.A.*, 90:2812–2816 (1993).
Hockenbery, D. M., et al., *Nature* 348:334–336 (1990).
Hockenbery, D. M., et al., *Cell* 75:241 (1993).
Hope, T. J., et al., *J. Virol.* 66:1849 (1992).
Inoue, A., et al., *J. Biol. Chem.* 264:14954–14959 (1989).
Jaffe, H. A., et al., *Nat. Genet.* 1:374 (1992).
Jahrondi, N., and Lynch, D. C., *Mol. Cell. Biol.* 14:999–1008 (1994).
Jones, N., and Shenk, T., *Cell* 16:683 (1979).
Karin, M., and Herrlich, P., in *GENES AND SIGNAL TRANSDUCTION IN MULTISTAGE CARCINOGENESIS* (Colburn, N. H., Ed.) Marcel Dekker, New York, N.Y., pp. 415–440 (1989).
Kasahara, N., et al., *Science* 266:1373 (1994).
Kass-Eisler, et al., *Proc. Natl. Acad. Sci.* 90:11498–11502 (1993).
Kennedy, P. G. and Steiner, I., *Q.J. Med.* 86:697–702 (1993).
Kirshenbaum, L. A., et al., *J. Clin. Invest.* 92:381 (1993).
Kitsis, R., et al., *Proc. Natl. Acad. Sci. U.S.A.* 88:4138 (1991).
Kourembanas, S., et al., *J. Clin. Invest.* 92:99 (1993).
Kwok, T. T., and Sutherland, R. M., *JNCI* 81:1020–1024 (1989).
Laderoute, K. R., et al., *Int. J. Cancer* 52:428–432 (1992).
Lantz, G. C., et al., *Am. J. Vet. Res.* 53:1594–1598 (1992).
Leclere, G., et al., *J. Clin. Invest.* 90:936 (1992).
Lefer, et al., *Circulation* 88:1779–1787 (1994).
Lin, H., et al., *Circulation* 82:2217 (1990).
Lord, E. M., et al., *J. Cancer Res.* 53:5721–5726 (1993).
Luke, M. C., et al., *J. Androl* 15:41 (1994).
Madan, A., et al., *Proc. Natl. Acad. Sci.* 90:3928 (1993).
Mahdavi, V., et al., *Proc. Natl. Acad. Sci.* 81:2626 (1984).
Malim, M. H., et al., *J. Exp. Med.* 176:1197 (1992).
Malin, M. H., et al., *Cell* 58:205 (1989).
Marci, P., et al., *Hum. Gene Ther.* 5:175 (1994).
Miller, A. D., *Hum. Gene Ther.* 1:5 (1990).
Miller, et al., *Vet. Clin. North Am. Anim. Pract.* 19:87–102 (1989).
Minty, A., and Kedes, L., *Mol. Cell Biol.* 6:2125–2136 (1986).
Molkentin, J. D., et al., *Mol. Cell Biol.* 144:947–4957 (1994).
Morishita, R., et al., *J. Clin. Invest.* 91:2580 (1993).
Mullis, K. B., et al., U.S. Pat. No. 4,683,195, issued Jul. 28, 1987.
Mullis, K. B., U.S. Pat. No. 4,683,202, issued Jul. 28, 1987.
Murtha, P., et al., *Biochem.* 32:6459 (1993).
Muscat, G. E. O., and Kedes, L., *Mol. Cell Biol.* 7:4089–4099 (1987).
Nabel, E. G., et al., *Science* 249:1285 (1990).
Nakane, M., et al., *FEBS Lett.* 316:175 (1993).
Pennica, D., et al., *Nature* 312:724–729 (1984).
Peshavaria, M., and Day, I. N. M., *Biochem. J.* 275:427–433 (1991).
Quantin, B., et al., *Proc. Natl. Acad. Sci. U.S.A.* 89:2581 (1992).
Reimer, D. L., et al., *Genomics,* 21:325 (1994).
Rosenberg, M. E., and Paller, M. S., *Kidney International,* 39:1156–1161 (1991).
Rosenfeld, M. A., et al., *Science* 252:431 (1991).
Rosenfeld, M. A., et al., *Cell* 68:143–155 (1992).
Rossi, J. J., and Sarver, N., *Adv. Exp. Med. Biol.* 312:95 (1992).
Sambrook, J., et al., *MOLECULAR CLONING: A LABORATORY MANUAL*, Second Edition, Cold Spring Harbor Laboratory Press, Cold Spring Harbor, N.Y. (1989).

Sasaoka, T., et al., *Brain Res. Mol. Brain Res.* 16:274 (1992).
Schulz, G. E., et al., *PRINCIPLES OF PROTEIN STRUCTURE*, Springer-Verlag New York Inc. (1979).
Scott-Moncrieff, J. C., et al., *J. Am. Vet. Med. Assoc.* 201:1553–1558 (1992).
Semenza, G. L., and Wang, G. L., *Mol. Cell Biol.* 12:5447–5454 (1992).
Seto, M., et al., *EMBO J.* 7:123 (1988).
Shirai, T., et al., *Nature* 313:803–806 (1985).
Smith, E. F., et al., *Am. J. Physiol.* 255:H1060–H1068 (1988).
Stratford-Perricaudet, L. D., et al., *J. Clin. Invest.* 90:626 (1992a).
Stratford-Perricaudet, L. D., et al., *Bone Marrow Transplant* 9(suppl. 1):151 (1992b).
Subramaniam, A., et al., *J. Biol. Chem.* 268:4331–4336 (1993).
Sullenger, B. A., et al., *J. Virol.* 65:6811 (1991).
Sullivan, K. E., et al., *Vet. Surg.* 22:343–350 (1993).
Takenaka, M., et al., *J. Biol. Chem.* 264:2363–2367 (1989).
Takiguchi, M., et al., *J. Biol. Chem.* 266:9186 (1991).
Thornton, J. D., et al., *J. Mol. Cell Cardiol.* 25:311 (1993).
Titus, D. E., Ed., *PROMEGA PROTOCOLS AND APPLICATIONS GUIDE*, Second Edition, Promega Corporation, Madison, Wis. (1991).
Tsujimoto, Y., et al., *Proc. Natl. Acad. Sci.* 83:5214–18 (1986).
Vibert, M., et al., *Eur. J. Biochem.* 181:33 (1989).
Wagner, E., et al., *Proc. Natl. Acad. Sci. U.S.A.* 89:6099 (1992a).
Wagner, E., et al., *Proc. Natl. Acad. Sci. U.S.A.* 89:7934 (1992b).
Webster, K. A., and Bishopric, N. H., *J. Mol. Cell Cardiol.* 24:741–751 (1992).
Webster, K. A. and Kedes, L., *Mol. Cell Biol.* 10:2402–2406 (1990).
Webster, K. A., et al., *J. Biol. chem.* 268:16852–16858 (1993).
Williams, G. T., and Smith, C. A., *Cell* 74:777–778 (1993).
Wilson, D. V., and Stick, J. A., *Am. J. Vet. Res.* 54:442–448 (1993).
Wolf, A., et al., *Science* 247:1465 (1990).
Wu, G. Y., *J. Biol. Chem.* 266:14338 (1991).
Youker, et al., *J. Clin. Invest.* 89:602–609 (1992).
Yung, W. K., *Curr. Opin. Oncol.* 6:235–239 (1994).
Zhang, L. X., et al., *Neuroreport* 3:700 (1992).

BACKGROUND OF THE INVENTION

Each year, over a half-million Americans die from heart attacks. Even more—close to 700,000—have non-fatal heart attacks. For these surviving victims, a portion of the heart is usually damaged irreparably. Such cell death of cardiac tissue, called myocardial infarction, is due in large part to tissue damage caused by ischemia and/or ischemia followed by reperfusion.

Similar ischemic damage may occur in many other tissues when the blood supply to the tissue is reduced or cut off. Stroke, deep vein thrombosis, pulmonary embolus, and renal failure are examples.

Surviving victims of ischemic episodes, such as heart attacks, are at substantially greater risk for subsequent episodes of ischemia, which in many cases prove debilitating or fatal. Thus, it would be desirable to have therapeutic methods and compositions by which survivors of heart attacks and other types of ischemic insults could lower the risk of tissue damage due to recurrent ischemic/reperfusion episodes.

SUMMARY OF THE INVENTION

In one aspect, the invention includes a method for reducing ischemic injury to a cell exposed to hypoxic conditions. The method includes introducing into the cell a chimeric gene containing a hypoxia response element, a therapeutic gene, and a tissue-specific promoter operably linked to the therapeutic gene to control transcription of the therapeutic gene in the cell, where the element is effective to modulate expression of the therapeutic gene. Exposing the cell to hypoxic conditions enhances expression of the gene and expression of the gene is effective in reducing ischemic injury to the cell. The method may be applied to, for example, cardiac cells using a cardiac-specific promoter, kidney cells using a kidney-specific promoter, brain cells using a brain-specific promoter, and vascular endothelium cells using a vascular endothelium-specific promoter. The hypoxia response element may be selected from, for example, the erythropoietin HRE element (HREE1), muscle pyruvate kinase (PKM) HRE element, β-enolase (enolase 3; ENO3) HRE element, endothelin-1 (ET-1) HRE element and metallothionein II (MTII) HRE element. The therapeutic gene may be selected from, for example, nitric oxide synthase (NOS), B-cell leukemia/lymphoma 2 (bcl-2), superoxide dismutase (SOD) and catalase. In a preferred embodiment, the promoter is heterologous to said element.

In another aspect, the invention includes a chimeric gene, containing a hypoxia response element, a tissue-specific promoter heterologous to the element, and a therapeutic gene. The promoter is operably linked to the therapeutic gene and the element is effective to modulate expression of the therapeutic gene. The method may be used with a variety of cell types and corresponding promoters, for example, as identified above. Suitable cardiac-specific promoters include the α-MHC$_{5.5}$ promoter, α-MHC$_{86}$ promoter, and human cardiac actin promoter. Suitable kidney-specific promoters include the renin promoter. Suitable brain-specific promoters include the aldolase C promoter and the tyrosine hydroxylase promoter. Suitable vascular endothelium-specific promoters include the Et-1 promoter and vonwillebrand factor promoter. Hypoxia response enhancer element useful with the method include HREE1, PKM HRE element, ENO3 HRE element and ET-1 HRE element. Exemplary therapeutic genes useful with the method include NOS, Bcl-2, SOD and catalase.

Another aspect of the present invention includes the above-described chimeric gene carried in an expression vector. The expression vector may be a plasmid, adenovirus vector, retrovirus vector, or the like.

In still another aspect, the invention includes a chimeric gene which contains a hypoxia response element, a tissue-specific promoter heterologous to the element, and a deleterious gene. The promoter is operably linked to the deleterious gene, and the element is effective to modulate expression of the deleterious gene. Suitable promoters include tumor-specific promoters, such as alpha fetoprotein (AFP) promoter. Suitable hypoxia response elements are as articulated above. Deleterious genes useful in this aspect include a viral thymidine kinase gene (tk), such as the herpes simplex virus (HSV) tk, and tumor necrosis factor (TNF).

In a related aspect, the invention includes a method of causing injury to a cell exposed to hypoxic conditions. The method includes introducing into the cell a vector containing a hypoxia response element, a deleterious gene, and a tissue-specific promoter operably linked to the gene and capable of controlling transcription of the gene in the cell. Exposing the cell to hypoxic conditions enhances expression of the gene, and expression of the gene is effective to cause injury to the cell. Promoters useful with this method include tumor-specific promoters such as the AFP promoter. Specific hypoxia response elements and deleterious genes useful with the method are also as identified above.

The invention also includes a chimeric gene which contains a hypoxia response element isolated from the metallothionein II promoter (e.g., an HRE contained in a fragment having the sequence represented as SEQ ID NO:35), a promoter and a heterologous gene. In one general embodiment, the heterologous gene is a therapeutic gene, as described above. In another general embodiment, the heterologous gene is a deleterious gene as described above (e.g., a DNA sequence encoding tumor necrosis factor).

The invention further includes a method of causing injury to a cell exposed to hypoxic conditions. The method includes introducing into the cell a vector containing a hypoxia response element isolated from the metallothionein II promoter (e.g., an HRE contained in a fragment having the sequence represented as SEQ ID NO:35), a promoter and a deleterious gene (e.g., TNF). Exposing the cell to hypoxic conditions enhances expression of the deleterious gene, and expression of the gene is effective to cause injury to the cell.

The invention further includes a substantially isolated polynucleotide having a sequence corresponding to hypoxia response enhancer element(s) (HREE(s)) present in a control region of the muscle pyruvate kinase gene. The element may be derived from the promoter region, 5' untranslated region, or 3' untranslated region. In a related aspect, the invention includes an HRE element derived from a muscle pyruvate kinase gene.

Also included in the invention is a substantially isolated polynucleotide having a sequence corresponding to hypoxia response element(s) present in a control region of the endothelin-1 gene. The element may be derived from the promoter region, 5' untranslated region, or 3' untranslated region. In a related aspect, the invention includes an HRE element derived from an endothelin-1 gene.

Another aspect of the invention includes a substantially isolated polynucleotide having a sequence corresponding to hypoxia response element(s) present in a control region of the enolase 3 (EN03) gene. The element may be derived from the promoter region, 5' untranslated region, or 3' untranslated region. In a related aspect, the invention includes an HRE element derived from an EN03 gene. In another related aspect, the invention includes a hypoxia responsive element (HRE) contained in the region of the metallothionein II (MTAII) promoter corresponding to SEQ ID NO:35. In a preferred embodiment, the HRE element consists of a sequence derived from SEQ ID NO:35.

These and other objects and features of the invention will become more fully apparent when the following detailed description is read in conjunction with the accompanying drawings.

BRIEF DESCRIPTION OF THE FIGURES

FIGS. 6A, 6B, 6C, 6D and 6E show a schematic diagram of the construction of plasmids pGLPKM$_{460}$ (FIG. 6C), pGLPKM$_D$ (FIG. 6D), and pGLPKM$_{285}$ (FIG. 6E) from plasmid pGL2BV (FIG. 6B) and a fragment of the PKM promoter (FIG. 6A; SEQ ID NO:7).

FIGS. 7A, 7B and 7C show a schematic diagram of the construction of plasmid pGLET-1$_{700}$ (FIG. 7C) from plasmid pGL2BV (FIG. 7B) and a fragment of the ET-1 promoter (FIG. 7A; SEQ ID NO:8).

BRIEF DESCRIPTION OF THE SEQUENCES

Figure 1A:
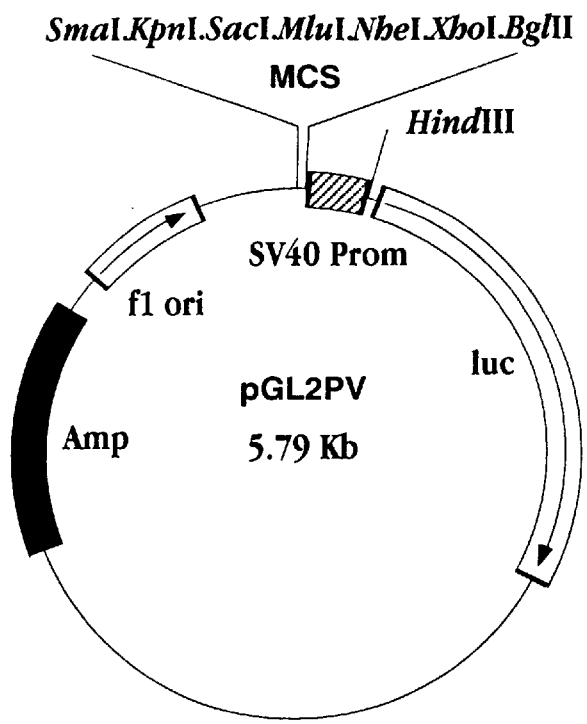
FIGS. 1A and 1B show a schematic diagram of the construction of plasmid pGLHRE (FIG. 1B) from plasmid pGL2PV (FIG. 1A).

SEQ ID NO:1 is the sense strand nucleotide sequence of a GATA4 enhancer element (Molkentin, et al., 1984).

SEQ ID NO:2 is the nucleotide sequence of muscle pyruvate kinase (PKM) sense strand primer F.

SEQ ID NO:3 is the nucleotide sequence of PKM reverse strand primer R.

SEQ ID NO:4 is the nucleotide sequence of endothelin-1 (Et-1) sense strand primer F.

SEQ ID NO:5 is the nucleotide sequence of Et-1 reverse strand primer R.

SEQ ID NO:6 is the nucleotide sequence of hypoxia response enhancer element 1 (HREE1), derived from the erythropoietin (EPO) gene (Semenza and Wang), and containing 4 tandem copies of a hypoxia response enhancer (HRE) sequence and cloning linkers.

SEQ ID NO:7 is the nucleotide sequence of a rat muscle pyruvate kinase (PKM) promoter region (Takenaka, et al.).

SEQ ID NO:8 is the nucleotide sequence of a human Et-1 promoter region (Inoue, et al.).

SEQ ID NO:9 is the nucleotide sequence of a human cardiac actin promoter region (Minty and Kedes).

SEQ ID NO:10 is a nucleotide sequence containing a portion of the rat cardiac α-myosin heavy chain promoter region (Mahdavi, et al.; GenBank Accession # K01464).

SEQ ID NO:11 is a nucleotide sequence containing a portion of the mouse cardiac α-myosin heavy chain promoter region (Gulick, J., et al.; GenBank Accession # M62404).

SEQ ID NO:12 is the nucleotide sequence of a human B-cell leukemia/lymphoma 2 (bcl-2) gene (Tsujimoto, et al.; GenBank Accession # M13994).

SEQ ID NO:13 is the predicted amino acid sequence from SEQ ID NO:12.

SEQ ID NO:14 is the nucleotide sequence of a rat nitric oxide synthase (bNOS) gene (Bredt, et al.; EMBL Accession # X59949).

SEQ ID NO:15 is the predicted amino acid sequence from SEQ ID NO:14.

SEQ ID NO:16 is the nucleotide sequence of a human bcl-2 fusion gene (Seto, et al.; EMBL Accession # X06487).

SEQ ID NO:17 is the predicted amino acid sequence from SEQ ID NO:16.

SEQ ID NO:18 is the nucleotide sequence of a human NOS-1 gene (Fujisawa, et al.); DDBJ Accession # D16408; NCBI Seq ID 506339).

SEQ ID NO:19 is the predicted amino acid sequence from SEQ ID NO:18.

SEQ ID NO:20 is the nucleotide sequence of a human NOS-SN gene (Nakane, et al.; GenBank Accession # L02881).

SEQ ID NO:21 is the predicted amino acid sequence from SEQ ID NO:20.

SEQ ID NO:22 is the nucleotide sequence of a 256 base pair (bp) 3' EPO-1 hypoxia response enhancer element (Semenza and Wang).

SEQ ID NO:23 is the nucleotide sequence of a 42 bp 3' EPO-1 hypoxia response enhancer element (Madan, et al.).

SEQ ID NO:24 is the nucleotide sequence of an 86 bp rat αMHC promoter region.

SEQ ID NO:25 is the nucleotide sequence of a mouse catalase gene (Reimer, et al.; GenBank #L25069).

SEQ ID NO:26 is the predicted amino acid sequence from SEQ ID NO:25.

SEQ ID NO:27 is the nucleotide sequence of a human manganese superoxide dismutase (SOD) gene (Clair, et al.; EMBL #X59445).

SEQ ID NO:28 is the predicted amino acid sequence from SEQ ID NO:27.

SEQ ID NO:29 is the nucleotide sequence of a human β-enolase (ENO3) gene (Giallongo, et al.; EMBL #X56832) between nucleotides −628 to +63.

SEQ ID NO:30 is the predicted amino acid sequence from SEQ ID NO:29.

SEQ ID NO:31 is a consensus sequence of a region present in both the PKM and ENO3 promoters.

SEQ ID NO:32 is the DNA sequence of the −760 fragment of the human metallothionein IIA (hMTAIIa) promoter.

SEQ ID NO:33 is the DNA sequence of the −345 fragment of the hMTAIIa promoter.

SEQ ID NO:34 is the DNA sequence of the −163 fragment of the hMTAIIa promoter.

SEQ ID NO:35 is the DNA sequence of the −90 fragment of the hMTAIIa promoter.

SEQ ID NO:36 is a cDNA sequence encoding human tumor necrosis factor (hTNF; EMBL Accession #X01394; Pennica, et al., Shirai, et al.).

SEQ ID NO:37 is the predicted amino acid sequence from SEQ ID NO:36.

DETAILED DESCRIPTION OF THE INVENTION

Definitions

"Ischemia" is defined as an insufficient supply of blood to a specific organ or tissue. A consequence of decreased blood supply is an inadequate supply of oxygen to the organ or tissue (hypoxia). Prolonged hypoxia may result in injury to the affected organ or tissue. "Anoxia" refers to a virtually complete absence of oxygen in the organ or tissue, which, if prolonged, may result in death of the organ or tissue.

"Hypoxic condition" is defined as a condition under which a particular organ or tissue receives an inadequate supply of oxygen.

"Anoxic condition" refers to a condition under which the supply of oxygen to a particular organ or tissue is cut off.

"Reperfusion" refers to the resumption of blood flow in a tissue following a period of ischemia.

"Ischemic injury" refers to cellular and/or molecular damage to an organ or tissue as a result of a period of ischemia and/or ischemia followed by reperfusion.

An "element", when used in the context of nucleic acid constructs, refers to a region of the construct or a nucleic acid fragment having a defined function. For example, a hypoxia response enhancer element is a region of DNA that, when associated with a gene operably linked to a promoter, enhances the transcription of that gene under hypoxic conditions.

The term "operably linked", as used herein, denotes a relationship between a regulatory region (typically a promoter element, but may include an enhancer element) and the coding region of a gene, whereby the transcription of the coding region is under the control of the regulatory region.

A polynucleotide sequence or fragment is "derived" from another polynucleotide sequence or fragment when it has the same sequence (or complement or reverse complement sequence) of nucleic acid residues as the corresponding region of the fragment from which it is derived.

Two nucleic acid elements are said to be "heterologous" if the elements are derived from two different genes, or alternatively, two different species. For example, a hypoxia response enhancer element from a human erythropoietin gene is heterologous to a promoter from a human myosin gene. Similarly, a hypoxia response enhancer element from a human erythropoietin gene, for example, is heterologous to a promoter from a mouse erythropoietin gene.

"Control region" refers to specific sequences at the 5' and 3' ends of eukaryotic genes which may be involved in the control of either transcription or translation. For example, most eukaryotic genes have an AT-rich region located approximately 25 to 30 bases upstream from the site where transcription initiation site. Similarly, most eukaryotic genes have a CXCAAT region (X may be any nucleotide) 70 to 80 bases upstream from the start of transcription. At the 3' end of most eukaryotic genes is an AATAAA sequence, which may be the signal for addition of the polyadenylation tail to the 3' end of the transcribed mRNA.

"Chimeric gene" refers to a polynucleotide containing heterologous DNA sequences, such as promoter and enhancer elements operably linked to a therapeutic gene. For example, a construct containing a human α-myosin heavy chain (α-MHC) promoter fragment operably linked to a human bcl-2 gene and containing a human erythropoietin gene hypoxia response element comprises an exemplary chimeric gene.

I. Overview of the Invention

The present invention relates to chimeric genes having at least three functional elements: (i) a therapeutic gene, (ii) a tissue-specific promoter, and (iii) a hypoxia response enhancer (HRE) element. The tissue-specific promoter in combination with the HRE element directs expression of the therapeutic gene in a selected tissue under hypoxic conditions.

The gene is preferably introduced into a target tissue as part of a complete expression vector in a pharmaceutically-acceptable vehicle, either by direct administration to the target tissue (e.g., injection into the target tissue), or by systemic administration (e.g., intravenous injection). In the latter case, the gene may be targeted to a selected tissue, for example, by incorporating it in a virion expressing a modified envelope protein designed to bind to receptors preferentially expressed on cells from the selected, or targeted, tissue. Regardless of the delivery means, expression of the gene in tissues other than the target tissue, and under conditions other than hypoxic or anoxic is preferably minimal.

As described below, a variety of therapeutic genes, promoters, HRE elements and gene delivery means may be employed in the practice of the present invention.

II. Tissue Specific Promoters

A promoter, in the context of the present specification, refers to a polynucleotide element capable of regulating the transcription of a gene adjacent and downstream (3') of the promoter. The promoter may contain all of, or only a portion of, the complete 5' regulatory sequences of the gene from which it is derived. A sequence in the promoter region is typically recognized by RNA polymerase molecules that start RNA synthesis.

A promoter may be functional in a variety of tissue types and in several different species of organisms, or its function may be restricted to a particular species and/or a particular tissue. Further, a promoter may be constitutively active, or it may be selectively activated by certain substances (e.g., a tissue-specific factor), under certain conditions (e.g., hypoxia, or the presence of an enhancer element in the chimeric gene containing the promoter), or during certain developmental stages of the organism (e.g., active in fetus, silent in adult).

Promoters useful in the practice of the present invention are preferably tissue-specific—that is, they are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the present invention typically has a selectivity ratio of greater than about 5. Preferably, the selectivity ratio is greater than about 15.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the present invention. For example, promoters that are active in a variety of central nervous system (CNS) neurons may be therapeutically useful in protecting against damage due to stroke, which may effect any of a number of different regions of the brain.

Tissue-specific promoters may be derived, for example, from promoter regions of genes that are differentially expressed in different tissues. For example, a variety of promoters have been identified which are suitable for upregulating expression in cardiac tissue. Included are the cardiac α-myosin heavy chain (αMHC) promoter and the cardiac α-actin promoter.

A further desirable characteristic of promoters useful in the present invention is that they possess a relatively low activity in the absence of activated hypoxia-regulated enhancer elements, even in the target tissues. One means of achieving this is to select promoters of genes encoding proteins that have a relatively low turnover rate in adult tissue, such as the actin and α-MHC promoters described herein. Another means is to use "silencer" elements, which suppress the activity of a selected promoter in the absence of hypoxia.

The level of expression of a gene under the control of a particular promoter can be modulated by manipulating the promoter region. For example, different domains within a promoter region may possess different gene-regulatory activities. The roles of these different regions are typically assessed using vector constructs having different variants of the promoter with specific regions deleted (i.e., deletion analysis). Vectors used for such experiments typically contains a reporter gene, which is used to determine the activity of each promoter variant under different conditions. Application of such a deletion analysis enables the identification of promoter sequences containing desirable activities.

This approach may be used to identify, for example, the smallest region capable of conferring tissue specificity, or the smallest region conferring hypoxia sensitivity.

A number of tissue specific promoters, described below, may be particularly advantageous in practicing the present invention. In most instances, these promoters may be isolated as convenient restriction digest fragments suitable for cloning into a selected vector.

Alternatively, promoter fragments may be isolated using the polymerase chain reaction (PCR; Mullis, Mullis, et al.). Cloning of amplified fragments may be facilitated by incorporating restriction sites at the 5' ends of the primers.

Promoters suitable for cardiac-specific expression include the promoter from the murine cardiac α-myosin heavy chain gene. The gene contains a 5.5 kbp promoter region which may be obtained as a 5.5 kbp SacI/SalI fragment from the murine αMHC gene (Subramaniam, et al., 1991). Reporter gene constructs utilizing this 5.5 kbp αMHC promoter are expressed at relatively high levels selectively in cardiac tissue (whether or not an HREE is present) and, when present in transgenic animals, are regulated in a similar fashion to the endogenous gene (Subramaniam, et al., 1991).

A smaller fragment of the rat α-MHC promoter may be obtained as a 1.2 kbp EcoRI/HindIII fragment (Gustafson, et al.). As shown in Example 1 and Table 1, below, constructs utilizing the 1.2 kbp rat αMHC promoter are expressed at a low level in the absence of an HREE, and at an intermediate level in the presence of an HREE. These results indicate that the $\alpha MHC_{1.2}$ promoter is an exemplary promoter to target expression of chimeric genes of the present invention to cardiac tissue. Expression of genes under the control of this promoter fragment is very low in cardiac cells under normal oxygenation conditions, but is increased by about a factor of four under hypoxic conditions when the construct contains HREE1. Expression in cells other than cardiac cells is at background levels.

An 86 bp fragment of the rat αMHC promoter, presented herein as SEQ ID NO:24, restricts expression of reporter genes to cardiac and skeletal muscle (i.e., it has lost some tissue selectivity). Additional cardiac specificity may be conferred to the fragment by ligating (e.g., blunt end ligating) a 36-mer oligonucleotide (SEQ ID NO:1) containing cardiac-specific GATA4 enhancer elements just upstream of base pair –86 (Molkentin, et al., 1984). This promoter fragment also results in low levels of expression in the absence of additional enhancers such as HRE elements. The low level of basal expression induced by the 86 bp fragment, and the ability to upregulate this basal level of expression with a hypoxia response enhancer element are useful properties for a promoter for use with the present invention.

The sequences of exemplary cardiac-specific promoter regions from the rat and mouse αMHC genes are presented herein as SEQ ID NO:10 and SEQ ID NO:11, respectively. Both sequences end just upstream of the ATG initiation codons of their respective genes. Other cardiac-specific promoters include the cardiac α-actin promoter and the myosin light chain-2 (MLC-2) promoter. Constructs described herein utilizing a 118 bp fragment (SEQ ID NO:9) from the human cardiac α-actin (HCA) promoter result in a relatively low level of cardiac-specific expression, which may be increased by the inclusion of an HREE in the expression construct (Example 1, Table 1). The cardiac-specific myosin light chain-2 promoter may be obtained as a 2.1 kbp KpnI/EcoRI fragment from the rat cardiac myosin light chain-2 (MLC-2) gene (Franz, et al.).

Prostate-specific promoters include the 5'-flanking regions of the human glandular kallikrein-1 (hKLK2) gene and the prostate-specific antigen (hKLK3; PSA) gene (Murtha, et al.; Luke, et al.). The renin promoter is suitable for directing kidney-specific expression (Fukamizu, et al.), while the aldolase-C promoter (Vibert, et al.) or the tyrosine hydroxylase promoter (Sasaoka, et al.) may be used to direct expression in the brain. Promoters specific for vascular endothelium cells include the Et-1 promoter (Inoue, et al.) and vonWillebrand factor (Jahrondi and Lynch) promoter.

Tumor-specific promoters include the α-fetoprotein (AFP) promoter, contained in a 7.6 kbp fragment of 5'-flanking DNA from the mouse AFP gene (Marci, et al.). This promoter normally directs expression of the AFP gene in fetal liver and is transcriptionally silent in adult tissues. However, it can be abnormally reactivated in hepatocellular carcinoma (HCC), conferring tumor-specific expression in adult tissue (Marci, et al.).

The above promoters are exemplary promoters for use with the present invention. Other promoters suitable for use with the present invention may be selected by one of ordinary skill in the art following the guidance of the present specification.

III. Hypoxia Response Enhancer Elements

Therapeutic genes contained in constructs of the present invention are preferably expressed at low levels, if at all, under conditions of normal oxygenation (minimizing any side effects). Under conditions of hypoxia, however, expression of the genes is increased, affording protection to the target tissue. The elevated expression under hypoxic conditions is conferred by the presence of one or more hypoxia response enhancer (HRE) elements.

HRE elements contain polynucleotide sequences that may be located either upstream (5') or downstream (3') of the promoter and/or therapeutic gene. The HRE element (HREE) is typically a cis-acting element, usually about 10–300 bp in length, that acts on a promoter to increase the transcription of a gene under the control of the promoter. Preferably, the promoter and enhancer elements are selected such that expression of a gene regulated by those elements is minimal in the presence of a healthy supply of oxygen, and is upregulated under hypoxic or anoxic conditions.

Hypoxia response enhancer elements are found in association with a number of genes, including the erythropoietin (EPO) gene. Exemplary HRE elements from the EPO gene are presented herein as SEQ ID NO:6, SEQ ID NO:22 and SEQ ID NO:23. The element having the sequence represented as SEQ ID NO:22 results in approximately a five-fold induction of reporter gene expression under hypoxic conditions (Semenza and Wang), while, the element having the sequence represented as SEQ ID NO:23 results in approximately a 17-fold increase in activity under hypoxic conditions (Madan, et al.).

Experiments performed in support of the present invention (e.g., Example 1) demonstrate that expression of constructs containing HREE1 (SEQ ID NO:6) is increased by approximately 5- to 7-fold in response to hypoxic conditions. These results indicate that the HREE1 element is fully functional when fused to muscle and cardiac specific promoters and that muscle and cardiac cells are fully responsive to hypoxia in terms of the regulation of these promoters.

Expression of constructs containing a fragment (SEQ ID NO:29) from the control region of the enolase 3 (ENO3) gene was induced approximately 5 to 8 fold by hypoxia in C2C12 cells and cardiac myocytes respectively (see Table 1). These results suggest that the HREE in the ENO3 promoter fragment may be a particularly effective HREE for hypoxia induction in constructs containing a tissue-specific promoter, such as a cardiac or skeletal muscle promoter.

According to the present invention, exemplary hypoxia response enhancer elements may also be isolated from regulatory regions of both the muscle glycolytic enzyme pyruvate kinase (PKM) gene (Takenaka, et al.), the human muscle-specific β-enolase gene (ENO3; Peshavaria and Day), and the endothelin-1 (ET-1) gene (Inoue, et al.). The HRE regions from the PKM gene and the ET-1 gene, identified in experiments performed in support of the present invention (see Materials and Methods, Examples 4 and 5), are presented herein as SEQ ID NO:7 and SEQ ID NO:8, respectively.

Example 4 demonstrates that the expression of pGLPKM, a plasmid containing the HRE element from the PKM gene, in transfected C2C12 myotubes and neonatal cardiac myocytes was increased by 6±2 (n=4) fold in both cell types by incubation of the cells in a hypoxic atmosphere. A portion of this HRE element, obtained by digesting with SmaI to cut at an internal SmaI site, localized the hypoxia response sequence to a 200 bp fragment. This fragment, termed $HREPKM_{285}$, confers hypoxia-induced expression in C2C12 myotubes and cardiac myocytes that is at least equivalent to that obtained using HREE1 (SEQ ID NO:6).

Both PKM and ENO3 promoters contain a common sequence element (SEQ ID NO:31) located at 5' −88 and −70 bp respectively from the transcription start sites. An oligonucleotide containing this sequence may be sufficient to confer hypoxia response characteristics to constructs of the present invention.

Data presented in Example 5 show that expression of $pGLET-1_{700}$, containing 700 bp of the human ET-1 gene promoter (SEQ ID NO:8), in transfected human arterial endothelial cells was increased approximately 5-fold by incubation of the cells in a hypoxia atmosphere. No hypoxia-induced increase in $pGLET-1_{700}$ expression was seen in other cell types, including HeLa cells, C2C12 cells, and cardiac myocytes. Accordingly, the 700 bp fragment may be used to target hypoxia regulated genes specifically to cells of the vascular endothelium, since the fragment contains element(s) conferring tissue specificity (i.e., elements effective to target expression exclusively to the vascular endothelium), as well as HRE element(s) effective to upregulate transcription of a gene under control of the fragment during hypoxia conditions.

Data presented in Example 6 show that hypoxia stress can increase transcription from constructs containing fragments of the hMTIIa proximal promoter. Enhancements in CAT activity relative to the aerobic controls were observed at both 8 and 14 hr of hypoxia. The levels of induction (2–3 fold) were within the same range as those found in the cadmium chloride-treated positive controls. Hypoxia responsiveness of the −760 construct (SEQ ID NO:32) was similar to that of the −345 (SEQ ID NO:33) construct.

Deletion analyses described in Example 7 show that extracts from cells transfected with constructs containing the −163 fragment (SEQ ID NO:34) and the −90 fragment (SEQ ID NO:35) showed significant upregulation of reporter activity (luciferase activity) under hypoxia conditions, with levels of induction (approximately 3.0-fold) similar to those observed in Example 6. These results suggest that at least one HRE element is contained in the proximal 90 bp fragment (SEQ ID NO:35) of the hMTIIa promoter. Such an HRE element may be utilized in the methods and constructs of the present invention.

It will be appreciated that deletion analyses such as described in Example 7 may be used to identify the shortest sequence present in the −90 fragment (SEQ ID NO:35) that still confers hypoxia sensitivity or inducibility, and that this shorter sequence may be used as the HRE element in the compositions and methods of the present invention.

It will further be appreciated that the present invention includes the use of HRE elements not explicitly identified above. Additional HRE elements may be identified, for example, as detailed in Examples 4 and 5. Further, promoter deletion and mutation analyses (e.g., as described above and in Webster and Kedes) may be used to identify such elements in other hypoxia responsive genes. A number of such responsive target genes have been shown to be induced when cells are exposed to hypoxia in vitro (e.g., Heakock and Sutherland).

It will also be appreciated that, in certain circumstances, the tissue-specific promoter and the hypoxia response enhancer element(s) of the present invention may be derived from a contiguous polynucleotide sequence from a single gene (e.g., as shown above for the ET-1 promoter region, which contains HRE element(s) and also imparts endothelial cell-specific expression).

IV. Therapeutic Genes

The present invention may be used to alleviate a number of disease conditions resulting from hypoxic and/or anoxic conditions due to ischemia where cell and tissue damage results from ischemia and ischemia followed by reperfusion. The invention is particularly suitable in cases where the subject is diagnosed to be at risk for an ischemic episode in a particular tissue.

For example, it is recognized that virtually all surviving heart attack victims are at significantly increased risk for recurrent episodes of myocardial ischemia. Such subjects would benefit from the introduction of constructs capable of expressing therapeutic genes into their cardiac tissue in order to decrease the risk of injury to the tissue during any subsequent ischemic episodes. Such constructs may serve to protect, for example, cardiac and vascular endothelial tissues from ischemic damage and thereby prevent the progression of the heart disease.

Recurrent ischemia and reperfusion typically results in oxidative damage to cells from reactive oxygen species (free radicals), such as peroxides, that are generated during redox switching (Frei). Contact of fresh blood with damaged or dead cells induces the influx of neutrophils, or pus cells, which kill heart cells which would otherwise have recovered. Much of the damage caused by neutrophils has been attributed to superoxide ions. The superoxide anion can damage tissue in several ways. The interaction of the superoxide anion with hydrogen peroxide leads to the production of hydroxyl radicals which are potentially toxic and react rapidly with most organic molecules. Lipids, proteins, and nucleic acids may all be primary targets for such oxidative damage. The extent and type of damage depend on the severity and nature of the hypoxic stress. For example, the stress may cause cellular damage, initiating an inflammatory response with neutrophil attack and subsequent tissue necrosis. Alternatively, the stress may initiate apoptosis (programmed cell death) to eliminate the damaged cells.

Regardless of the mechanism by which tissue death occurs (necrosis or apoptosis), the damage caused by ischemia-reperfusion episodes is typically the result of redox reactions and is quantitatively related to the severity and duration of the ischemia. For example, in the case of the myocardium, a severe heart attack may result in extensive damage (e.g., infarction of 30% to 40% of the left ventricle), whereas moderate angina and silent repetitive ischemia may result in relatively minor damage during each episode.

While the pathology of ischemia in tissues is complex, resulting in multiple potential targets for therapeutic intervention, several classes of targets are particularly suitable for therapeutic intervention in accordance with the teachings of the present invention. These include antioxidant systems, that may intervene immediately at the sites of intracellular redox reactions to minimize damage, and vasodilator systems, that may minimize the severity of the ischemia by increasing blood flow to vulnerable tissues. Antioxidant proteins amenable for use with the present invention include gene products of Bcl-2, catalase and superoxide dismutase (SOD) genes, while proteins with vasodilative properties include nitric oxide synthase (NOS), which produces the vasodilator nitric oxide (NO).

Bcl-2, an integral inner mitochondrial membrane protein of relative molecular mass ~25 kDa, has been shown to protect certain cells against apoptosis (Hockenbery, et al., 1990) by acting as an antioxidant (Hockenbery, et al., 1993). Bcl-2 may be an effective therapeutic gene for reducing damage to tissues during ischemic episodes because apoptosis may be a common response of many tissues, including the heart, to oxidative stress (Williams and Smith; Gottlieb, et al.

The enzyme superoxide dismutase (SOD) catalyzes the decomposition of the superoxide anion to peroxide. Enzymes such as superoxide dismutase, free radical scavengers or agents which prevent the influx on neutrophils are able to increase the salvage of heart muscle cells. The enzyme catalase in turn catalyzes the conversion of peroxides to water. Exemplary sequences of a SOD gene and a catalase gene are presented herein as SEQ ID NO:27 and SEQ ID NO:25, respectively. The sequence presented herein as SEQ ID NO:27 encodes a manganese SOD, which has a relatively long half-life. A related sequence, of a human Cu/Zn SOD, may be found in Gorechi, et al. The Cu/Zn SOD has a shorter half-life than the manganese SOD.

Endothelial-derived nitric oxide (NO) regulates the expression of vasoconstrictors and growth factors by the vascular endothelium (Kourembanas, et al.). Under hypoxia, endothelial cells typically increase expression and secretion of endothelin-1 (ET-1), a potent vasoconstrictor. This increase in expression can be reduced or prevented by exposure to NO (Kourembanas, et al.). One of the effects of ET-1 induced vasoconstriction is decreased blood flow to the affected organ or tissue, which can exasperate hypoxic damage due to ischemia. According to the present invention, such damage may be reduced by providing NO to the affected tissue through the expression of a NOS gene under the control of a vascular epithelium or cardiac-specific promoter and hypoxia response enhancer element.

Therapeutic genes of the present invention may be preferably derived from the same or related species as the one to which the methods and compositions of the present invention are applied. For example, for therapeutic treatment of a dog, it may be desirable to utilize a construct containing a therapeutic gene cloned from a dog. Similarly, for treatment of human conditions, it may be desirable to utilize therapeutic genes cloned from human-derived nucleic acids.

The genes encoding the proteins discussed above represent exemplary therapeutic genes useful in the practice of the present invention. It will be appreciated, however, that following the teachings and guidance of the present specification, one of skill in the art may select other therapeutic genes effective to reduce cellular damage due to hypoxia or ischemia, and that the use of such genes is considered to be within the scope of the present invention.

V. Deleterious Genes

In another aspect, the present invention includes constructs containing deleterious genes, rather than therapeutic genes. Expression of the deleterious genes is targeted to tissues which are harmful (e.g., malignant tumors) or otherwise undesirable. Promoters and hypoxia response elements may be selected as described above. Promoters useful in this aspect of the invention preferably restrict expression only to the undesirable tissue. For example, as discussed above, the AFP promoter can be activated in hepatocellular carcinoma (HCC), conferring tumor-specific expression in adult tissues (Marci, et al.).

Deleterious genes include a viral thymidine kinase gene (tk), such as the herpes simplex virus (HSV) tk. This gene is not deleterious by itself, but when expressed, viral TK can phosphorylate ganciclovir (GCV), turning GCV into a cytotoxic compound. Since tumor cells are typically hypoxic, constructs having a tumor-specific promoter operably linked to a viral tk and an HREE may be used in conjunction with GCV to selectively kill tumor cells. Another exemplary deleterious gene is tumor necrosis factor (TNF). TNF is a growth factor that rapidly and induces programmed cell death or apoptosis (Cleveland and Ihle, 1995).

VI. Expression Vectors

Chimeric genes of the present invention are preferably incorporated into expression vectors capable of expressing a therapeutic gene product in a selected eukaryotic host cell (i.e., a target tissue). Such expression vectors may contain, in addition to the chimeric gene, various other sequences useful for effective expression of the therapeutic gene in selected tissues. Such sequences may include, for example, sequences necessary for the termination of transcription. These sequences are transcribed as polyadenylated segments in the untranslated portion of the mRNA encoding the desired therapeutic protein. The 3' untranslated regions may also include transcription termination sites.

Molecular techniques and methods useful in the construction of expression vectors are well known in the art (e.g., Ausubel, et al., Sambrook, et al.). Vector constructs made in support of the present invention are designed to express either a reporter gene (e.g., luciferase), or therapeutic genes (e.g., Bcl-2 or NOS). Therapeutic gene expression is under the control of either a ubiquitous promoter (e.g., SV40), or a tissue-specific promoter (e.g., striated muscle or cardiac-specific promoter). Further regulation of expression by hypoxia or anoxia is provided by inclusion of hypoxia response enhancer (HRE) elements (e.g., from the erythropoietin (EPO) gene, muscle specific pyruvate kinase (PKM) gene, enolase 3 (ENO3) gene or the endothelial cell endothelin-1 (Et-1) gene).

The generation of exemplary constructs is described in the Materials and Methods section, below. The results of in vitro experiments to assess the performance of constructs having HREE1 and tissue specific promoters are presented in Example 1 and Table 1. The relative amount of gene expression was measured using a reporter gene (luciferase) in place of a therapeutic gene.

The data shown in Table 1 demonstrate that cells containing constructs having a hypoxia response enhancer element, such as HREE1, in combination with a compatible promoter, express the reporter at levels that are 5 to 7 times greater under hypoxic conditions than under aerobic conditions, and that HREE1 is equally active in different cells and independent of the promoter. The data also demonstrate that expression of constructs containing α-MHC promoters is cardiac specific, and that the basal (aerobic) expression from α-$MHC_{1.2}$ and HCA promoters is relatively low. Further, the data indicate that muscle and cardiac cells are fully responsive to hypoxia in terms of the regulation of these promoters.

In vivo experiments conducted with plasmids pGLHRE and pGLHCA$_{118}$HRE (Example 2, Table 2) demonstrate that gene expression in hearts of rats injected with the plasmids and subjected to ischemia was approximately 2-fold higher than expression in hearts from control animals (not subjected to ischemia). These results indicate that the direct injection of therapeutic constructs of the present invention into cardiac tissue in vivo is effective to result in the expression of genes carried on those plasmids. Further, these results indicate that expression vectors carrying chimeric genes of the present invention are effective to result in significantly increased levels of expression in response to hypoxia caused by ischemia in vivo.

Since expression was measured at 20 hours after a brief (20 minute) episode of ischemia, it will be appreciated that (i) hypoxia-induced expression may peak significantly earlier than 20 hours, and (ii) repeat ischemic episodes may upregulate expression more the single experimental episode used herein. Accordingly, the 2-fold induction may be an underestimate of the level of enhancement of transcription/expression caused by ischemia.

While the experiments described above were performed with cardiac tissue, it will be appreciated that one of ordinary skill in the art having the benefit of the present specification may perform similar manipulations with other tissues subject to ischemic and or ischemic/reperfusion injury, and that such procedures are within the scope of the present invention.

In vitro experiments (Example 3) demonstrate that cells transfected with reporter (pGLHRE, pGLHCA$_{118}$HRE, pGLαMHC$_{1.2}$HRE) and therapeutic (pSFFV-Bcl-2 and pNOS-HRE) constructs appear normal and respond to stimuli as expected. Reporter-transfected cells differentiate normally and respond to hypoxia with the predicted induction of reporter, while NOS and bcl-2-transfected cells appear normal both during the hypoxia and during subsequent reoxygenation. These results suggest that inclusion of HRE elements, Bcl-2 over-expression, and hypoxia-induced over-expression of NOS is not toxic or deleterious to muscle cells in vitro.

These results also suggest that expression vectors carrying therapeutic genes of the present invention may be effective to protect tissues from ischemic damage. Such protective effects may be assayed in an animal model by, for example, infecting myocardial tissue with an expression vector containing a chimeric gene of the present invention, such as an adenoviral vector expressing a therapeutic gene (e.g., Bcl-2 or SOD), a cardiac-specific promoter, and an HRE element, as described, for instance, in Example 2.

Following infection, the animals may be subjected to repeat ischemic episodes (e.g., 30 minutes to 1 hour) followed by reperfusion (e.g., 1 to 8 hours). Following the last reperfusion, the animals may be sacrificed and the ischemic regions of the myocardium may be tested for the presence and extent of infarction as described, for example, by Thornton, et al., and for the presence of apoptosis as described, for example, in Gottlieb, et al. Sample biopsies may also be assayed for expression of the therapeutic gene by Northern blots.

Similar experiments may be performed using constructs directed (e.g., via an appropriate promoter) to other tissues, such as brain, kidney and vascular endothelium.

Examples 8 and 9 describe exemplary constructs containing an HRE element from the hMTIIa promoter and a deleterious gene (TNF). The examples describe the testing of such constructs both in vitro (Example 8) and in vivo (Example 9).

VII. Delivery of Constructs to Cells and Tissues

Any of a variety of methods known to those skilled in the art may be used to introduce chimeric genes of the present invention into selected target tissue cells. For example, gene therapy of cardiac tissue has included lipofection, retrovirus and adenovirus-mediated gene transfer, and injection of naked DNA directly into the vascular endothelium or cardiac tissue (Nabel, et al.; Lin, et al.; Leclere, et al.; Flugelman, et al.). These and other methods are discussed more fully in the sections below.

A. Viral-Mediated Gene Transfer

Host cells may be transfected with chimeric genes of the present invention by infection with mature virions containing hybrid vectors (the chimeric genes along with selected viral sequences). The virions used to transfect host cells are preferably replication-defective, such that the virus is not able to replicate in the host cells.

The virions may be produced by co-infection of cultured host cells with a helper virus. Following coinfection, the virions are isolated (e.g., by cesium chloride centrifugation) and any remaining helper virus is inactivated (e.g., by heating). The resulting mature virions contain a chimeric gene of the present invention and may be used to infect host cells in the absence of helper virus. Alternatively, high titers of replication-defective recombinant virus, free of helper virus, may be produced in packaging cell lines containing those components for which the virus is defective (Miller).

Several types of viruses, including retroviruses, adeno-associated virus (AAV), herpes virus, vaccinia virus, and several RNA viruses may be amenable for use as vectors with chimeric gene constructs of the present invention. Each type of virus has specific advantages and disadvantages, which are appreciated by those of skill in the art. Methods for manipulating viral vectors are also known in the art (e.g., Grunhaus and Horowitz; Hertz and Gerard; and Rosenfeld, et al.)

Retroviruses, like adeno-associated viruses, stably integrate their DNA into the chromosomal DNA of the target cell. Unlike adeno-associated viruses, however, retroviruses typically require replication of the target cells in order for proviral integration to occur. Accordingly, successful gene transfer with retroviral vectors depends on the ability to at least transiently induce proliferation of the target cells.

Retroviral vectors are attractive in part due to the efficiency of transfection—some vectors can stably transduce close to 100% of target cells. The use of retroviral vectors for in vivo gene therapy has been limited, in part, by the requirement of appropriate viral receptors on the target cell. Because the identities of most retroviral receptors are unknown, it has not been possible to determine the distribution of receptors in different cell types. Accordingly, the targeting of specific cell types by retroviral vectors has in many cases proven problematic.

This difficulty may be circumvented by modifying the envelope protein of the retrovirus to contain a ligand for a known endogenous (not necessarily viral) receptor expressed on the target cells. An application of this technique is described in detail by Kasahara. Preferably, the virus also contains an unmodified envelope protein to facilitate cell entry. A number of receptors, such as desmin, E-selectin, and A-CAM, are expressed preferentially on cardiac cells and may be amenable to this approach (e.g., Hansen and Stawaski; Lefer, et al.; Youker, et al.).

Adeno-associated viruses are capable of efficiently infecting nondividing cells and expressing large amounts of gene product. Furthermore, the virus particle is relatively stable and amenable to purification and concentration. Replication-defective adenoviruses lacking portions of the E1 region of the viral genome may be propagated by growth in cells engineered to express the E1 genes (Jones and Shenk; Berkner; Graham and Prevea). Most of the currently-used adenovirus vectors carry deletions in the E1A–E1B and E3 regions of the viral genome. A number of preclinical studies using adenoviral vectors have demonstrated that the vectors are efficient at transforming significant fractions of cells in vivo, and that vector-mediated gene expression can persist for significant periods of time (Rosenfeld, et al.; Quantin, et al.; Stratford-Perricaudet, et al., 1992a; Rosenfeld, et al.; L. D. Stratford-Perricaudet, et al., 1992b; Jaffe, et al.). Several studies describe the effectiveness of adenovirus-mediated gene transfer to cardiac myocytes (Kass-Eisler, et al.; Kirshenbaum, et al.).

Herpes virus vectors (Breakefield and DeLuca; Freese, et al.) are particularly well suited for the delivery and expression of foreign DNA in cells of the central nervous system (CNS), since they can efficiently infect mature, postmitotic neurons. Methods for manipulating the vectors and transfecting CNS cells are well known (see, e.g., Kennedy and Steiner; Yung). A number of studies describe methods for transplanting genetically modified cells into different regions of the brain (Malim, et al.; Rossi and Sarver; Sullenger, et al.; Morgan, et al.; Chatterjee, et al.; Malin, et al.; Hope, et al.). Studies utilizing direct injection of vectors into CNS tissue have also been performed (e.g., Zhang, et al.).

B. Naked DNA Injection

Plasmids bearing chimeric genes of the present invention may be purified and injected directly into a target tissue, as exemplified in Example 2 for rat cardiac tissue. The data discussed in Example 2 demonstrate that cardiac injection of plasmid suspended in saline buffer is effective to result in expression of the plasmid in the cardiac cells. Similar approaches have been used successfully by others to express, for example, exogenous genes in rodent cardiac and skeletal muscle (Wolf, et al.; Ascadi, et al., 1991a; Ascadi, et al., 1991b; Lin, et al.; Kitsis, et al.

C. Liposome-Mediated Gene Transfer

Liposomes may be employed to deliver genes to target tissues using methods known in the art. The liposomes may be constructed to contain a targeting moiety or ligand, such as an antigen, an antibody, or a virus on their surface to facilitate delivery to the appropriate tissue. For example, liposomes prepared with ultraviolet (UV) inactivated Hemagglutinating Virus of Japan (HVJ) may be used to deliver DNA to selected tissues (Morishita, et al.).

The liposomes may also be surface-coated, e.g., by incorporation of phospholipid-polyethyleneglycol conjugates, to extend blood circulation time and allow for greater targeting via the bloodstream. Liposomes of this type are well known.

D. Receptor-Mediated Gene Transfer

Receptor-mediated endocytic pathways for the uptake of DNA may permit the targeted delivery of genes to specific cell types in vivo. Receptor-mediated methods of gene transfer involve the generation of complexes between plasmid DNA and specific polypeptide ligands (Wu) that can be recognized by receptors on the cell surface. One of the problems with receptor-mediated uptake for gene delivery is that the endocytic vesicles formed during this process may be transported to the lysosome, where the contents of the endosome are degraded. Methods have been developed to facilitate escape of the DNA from the endosome during the course of its transport. For example, either whole adenovirus (Wagner, et al., 1992a; Christiano, et al.) or fusogenic peptides of the influenza HA gene product (Wagner, et al., 1992b) may be used to induce efficient disruption of DNA-containing endosomes.

E. Administration of Constructs

In cases such as those outlined above, where a vector may be targeted to selectively transfect a specific population of cells, it will be understood that in addition to local administration (such as may be achieved by injection into the target tissue), the vector may be administered systemically (e.g., intravenously) in a biologically-compatible solution or pharmaceutically acceptable delivery vehicle. Vector constructs administered in this way may selectively infect the target tissue. According to the present invention, the presence of a target tissue-specific promoter on the construct provides an independent means of restricting expression of the therapeutic gene.

VIII. Applications

A. Therapeutic Applications

Compositions and methods of the present invention may be useful to prevent tissue damage and/or death, due to ischemia and/or subsequent reperfusion, in a variety of tissues. As stated above, an exemplary application is in the reduction of damage due to recurrent myocardial ischemia following a heart attack. The expression of therapeutic genes in the cardiac tissue of heart attack victims may decrease the risk of injury to the tissue during any subsequent ischemic episodes.

Similarly, subjects who have been diagnosed with transient cerebral ischemia, blood clots or other risk factors for stroke may benefit from the use of hypoxia-inducible brain-specific constructs. Subjects diagnosed with acute or chronic renal failure are at greater risk for further ischemic damage to the kidneys (e.g., Rosenberg and Paller). Such subjects may benefit from a therapeutic gene under the control of a kidney-specific promoter, expression of which is enhanced by hypoxic conditions. A variety of other tissues diagnosed as "at risk" for ischemia may be similarly protected, as will be appreciated by one of skill in the art having the benefit of the present specification.

In addition to the utilities discussed above, compositions (e.g., expression vectors containing chimeric genes of the present invention) and methods of the present invention also have a number of applications in animal medicine. Although animals do not usually develop classical atherosclerosis, cardiomyopathies are very common. A number of species develop ischemia-related syndromes, including arteritis, vasculitis, and related vasculopathies, that result in direct redox damage to cells and tissues, particularly to vascular walls and myocardial tissues. Such conditions may be alleviated by administration of chimeric genes of the present invention.

A common and serious condition in horses and ponies involves ascending colonic ischemia, usually caused by strangulation obstruction (Dabareiner, et al.; Sullivan, et al.; Wilson and Stick). A related disease in dogs is called gastric dilation-volvulus (Lantz, et al.). Treatment of these disorders typically involves surgical removal of the obstruction. Reperfusion following such surgery can result in significant injury to reperfused tissues, and typically triggers an inflammatory response with progressive tissue necrosis. The reperfusion may also results in death of the animal due to cardiogenic shock. Compositions and methods of the present invention may be used therapeutically to treat such conditions, and to provide protection to vulnerable tissues, including heart and vascular endothelium, during the treatment of the above syndromes.

Another utility of the present invention is the treatment of cardiac disease in cats and dogs (Miller, et al.). A variety of forms of cardiovascular disease have been described in both cats and dogs, including dilated cardiomyopathy, left ventricular hypertrophy, and hyperthyroidism (Fox, et al.; Atkins, et al.). Systemic necrotizing vasculitis, a condition that may be analogous to atherosclerosis in humans (with regard to plaque formation and intimal proliferation), has been described in Beagles (Scott-Moncrieff, et al.). Each of these conditions may involve ischemia and reperfusion redox injuries to cardiac and vascular tissue that may be treated using the methods and compositions of the present invention.

B. Reporter Constructs for Diagnostic Applications

The present invention may also be employed in diagnostic applications, where it is desirable to localize the site of hypoxia or anoxia. According to this aspect of the invention, therapeutic genes are replaced by reporter genes, such as those used in experiments performed in support of the present invention (e.g., luciferase). The chimeric genes containing the reporter genes under the control of a selected promoter and a hypoxia response element are introduced into a tissue where it is desirable to localize the site of hypoxia. Hypoxia is localized by increased expression of the reporter gene.

The following examples illustrate but in no way are intended to limit the present invention.

Materials and Methods

Unless indicated otherwise, chemicals and reagents were obtained from Sigma Chemical Company (St. Louis, Mo.) or Mallinckrodt Specialty Chemicals (Chesterfield, Mo.), restriction endonucleases were obtained from New England Biolabs (Beverly, Mass.), and other modifying enzymes and biochemicals were obtained from Pharmacia Biotech (Piscataway, N.J.), Boehringer Mannheim (Indianapolis, Ind.) or Promega Corporation (Madison, Wis.). Materials for media for cell culture were obtained from Gibco/BRL (Gaithersburg, Md.) or DIFCO (Detroit, Mich.). Unless otherwise indicated, manipulations of cells, bacteria and nucleic acids were performed using standard methods and protocols (e.g., Titus; Sambrook, et al.; Ausubel, et al.).

I. Definitions

"Transformation" means introducing DNA into an organism so that the DNA is replicable, either as an extrachromosomal element or by chromosomal integration. Several transformation methods are commonly used in the art, and may be found, for example, in Ausubel, et al., and Sambrook, et al.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of the expression vector occurs within the host cell.

"Plasmids" are designated by a lower case p preceded and/or followed by capital letters and/or numbers. The starting plasmids herein are either commercially available, publicly available on an unrestricted basis, or can be constructed from available plasmids in accord with published procedures.

"Digestion" of DNA refers to catalytic cleavage of the DNA with a restriction enzyme that acts only at certain sequences (restriction sites) in the DNA. The various restriction enzymes used herein are commercially available (e.g., New England Biolabs, Beverly, Mass.) and their reaction conditions are known to the ordinarily skilled artisan. For analytical purposes, typically 1 μg of a plasmid or of a DNA fragment is used with about 2 units of enzyme in about 20 μl of buffer solution. For the purpose of isolating DNA fragments for plasmid construction, typically 5 to 10 μg of DNA are digested with about 20 to 40 units of enzyme in a larger volume. Appropriate buffers and substrate amounts for particular restriction enzymes are specified by the manufacturer. Incubation times of about one hour at 37° C. are ordinarily used, but may vary in accordance with the supplier's instructions. After digestion, the reaction products are run on a gel (e.g., agarose) to isolate desired fragments.

"Ligation" refers to the process of forming phosphodiester bonds between two double stranded nucleic acid fragments (e.g., Sambrook, et al.). Unless otherwise noted, ligation may be accomplished using known buffers and conditions with 10 units of T4 DNA ligase per 0.5 μg of approximately equimolar amounts of the DNA fragments to be ligated.

"Filling" or "blunting" refer to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 μg of the target DNA in a buffer containing 10 mM $MgCl_2$, 1 Mm dithiothreitol, 50 mM NaCl, 10 mM Tris (pH 7.5) at about 37° C. in the presence of 8 units of the Klenow fragment of DNA polymerase I (Boehringer Mannheim, Indianapolis, Ind.) and 250 μm of each of the four deoxynucleoside triphosphates (Boehringer Mannheim). The incubation is generally terminated after about 30 min. The reaction products may be purified using standard phenol and chloroform extraction methods followed by ethanol precipitation.

"Northern" blotting is a method by which the presence of a cellular MRNA is confirmed by hybridization to a known, labelled oligonucleotide, DNA or RNA fragment. For the purposes herein, unless otherwise provided, Northern analysis shall mean electrophoretic separation of RNA, typically MRNA, on agarose (e.g., 1%) in the presence of a denaturant (e.g., 7% formaldehyde), transfer to nitrocellulose or nylon membrane, hybridization to the labelled fragment, washing, and detection of the labeled fragment, as described by Sambrook, et al.

II. Cells and Media

HeLa cells, Hep G2 cells and C2C12 myoblasts were obtained from the American Type Culture Collection (ATCC; Rockville, Md.). Human arterial endothelial cells were obtained from Clonetics Corp. (San Diego, Calif.). Unless otherwise indicated, the cells were grown at 37° C. under 5 or 10% $CO_2$ in MEM or DMEM medium (Gibco/BRL) containing 10% fetal bovine serum (Gibco/BRL).

Cardiac myocytes were isolated and cultured as described previously (Bishopric, et al., Webster and Bisphopric, 1992). Briefly, hearts from about 30 (three litters) were minced and subjected to serial trypsin digestion to release single cells. After the final digestion, the cells were washed and preplated for 0.5 h in minimal essential medium (MEM; Gibco/BRL, Gaithersburg, Md.) with 5% fetal calf serum (FCS; Gibco/BRL). Nonattached cells were re-plated in 60-mm Falcon dishes (Becton Dickinson Labware, Lincoln Park, N.J.) at a density of about $2.5 \times 10^6$ cells per dish in MEM containing 5% fetal calf serum, 2.0 g/l glucose and 10 mM HEPES, and grown at 37° C. under 5 or 10% $CO_2$.

III. DNA

A. Therapeutic Genes

Bcl-2 cDNA was obtained in the expression vector pSFFV-Bcl-2 from Dr. Stanley Korsemeyer (Washington University, St. Louis, Mo.; Hockenbery, et al., 1990). Nitric oxide synthase (bNOS) cDNA was obtained from Dr. Solomon Snyder in the vector pNOS (Johns Hopkins University, Baltimore, Md.; Bredt, et al., 1991).

B. Promoters

1. Cardiac-specific. $p\alpha MHC_{5.5}CAT$, containing 5.5 kilobases (Kb) 5' of the mouse α-myosin heavy chain (αMHC) promoter ligated to the chloramphenicol acetyl transferase (CAT) gene, was obtained from Dr. Jeffrey Robbins (University of Cincinnati, College of Medicine, Cincinnati, Ohio; Subramaniam, et al.).

$p\alpha MHC_{2.0}CAT$, containing 2.0 Kb of the rat αMHC promoter ligated to the CAT gene, was obtained from Dr. Thomas Gustafson (University of Maryland, Baltimore, Md.; Gustafson, et al.).

$p\alpha MHC_{86}CAT$, containing 86 base pairs (bp) of the rat αMHC promoter ligated to the CAT gene, was obtained from Dr. Bruce Markham (Medical College of Wisconsin, Milwaukee, Wis.). The construct was made by 5' truncation of pαMHC2.0CAT and blunt end ligation to the CAT gene. The sequence of the 86 bp promoter fragment is provided herein as SEQ ID NO:24.

$pHCA_{118}CAT$, containing 118 bp of the region 5' of the human cardiac α-actin promoter ligated to the CAT gene, was also obtained from Dr. Larry Kedes (Minty and Kedes).

2. Skeletal muscle-specific. pHSA-150CAT, containing 150 bp of the human skeletal muscle α-actin promoter ligated to the CAT gene, was obtained from Dr. Larry Kedes (University of Southern California, Los Angeles, Calif.; Muscat and Kedes).

3. Hypoxia Response Elements. A construct containing four tandem copies of the erythropoietin gene 3' hypoxia inducible enhancer element cloned into the BamHI site of pGEM-4Z (Promega Corp., Madison, Wis.) was obtained from Dr. Greg Semenza (Johns Hopkins University School of Medicine, Baltimore, Md.; Semenza and Wang, 1992). The enhancer element fragment, termed herein as HREE1 (SEQ ID NO:6), was excised from the pGEM vector by cleavage with SmaI and HincII for blunt end subcloning into constructs of the present invention (below).

A construct containing 691 bp (−628 to +63) of the β-enolase (ENO3) gene was obtained from Dr. Charlotte Peterson (Veterans Administration Medical Center, University of Arkansas, Little Rock, Ark.). A sequence containing this region is presented herein as SEQ ID NO:29.

4. Chimeric Genes and Expression Vectors of the Present Invention. The vector pGL2PV (plasmid-gene-light-promoter-vector; Promega Corp., Madison, Wis.), was used as the base vector for the construction of most of the plasmids described below. pGL2PV is a eukaryotic expression vector containing the SV40 early promoter upstream of the luciferase gene. The vector multiple cloning (MCS) site is just upstream of the SV40 promoter, and is designed for the insertion of DNA fragments containing enhancer sequences. pGL2BV (Promega Corp.) is similar to pGL2PV, but it does not contain an SV40 early promoter.

Figure 1B:
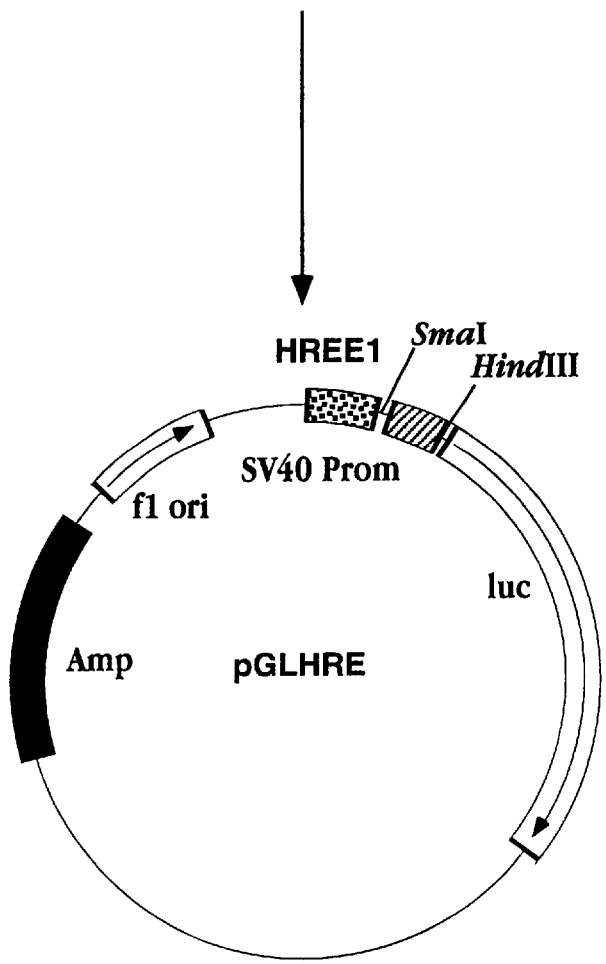
Figure 2A:
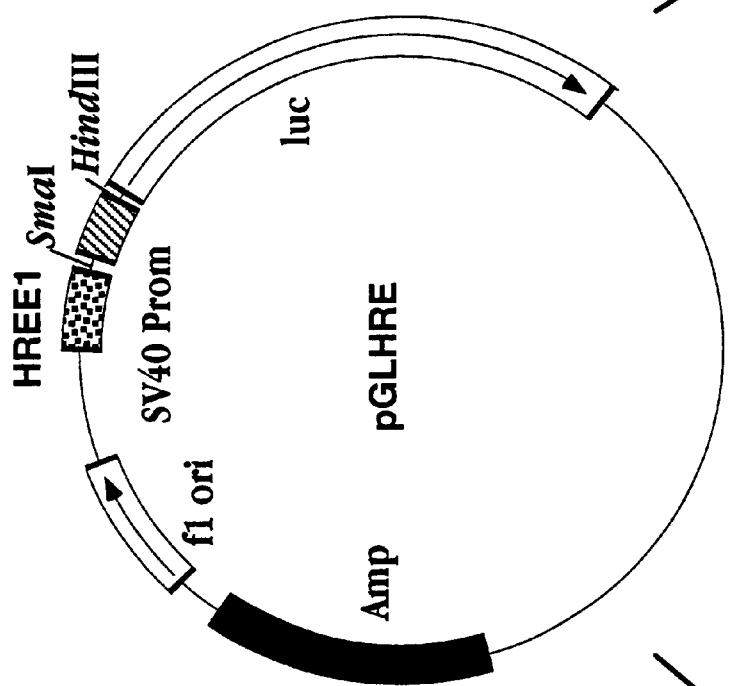
FIGS. 2A, 2B, 2C and 2D show a schematic diagram of the construction of plasmids pGLHSA-150HRE (FIG. 2B), pGLαMHC$_{86}$-HRE (FIG. 2C), and pGLHCA$_{118}$HRE (FIG. 2D), from plasmid pGLHRE (FIG. 2A).
Figure 3A:
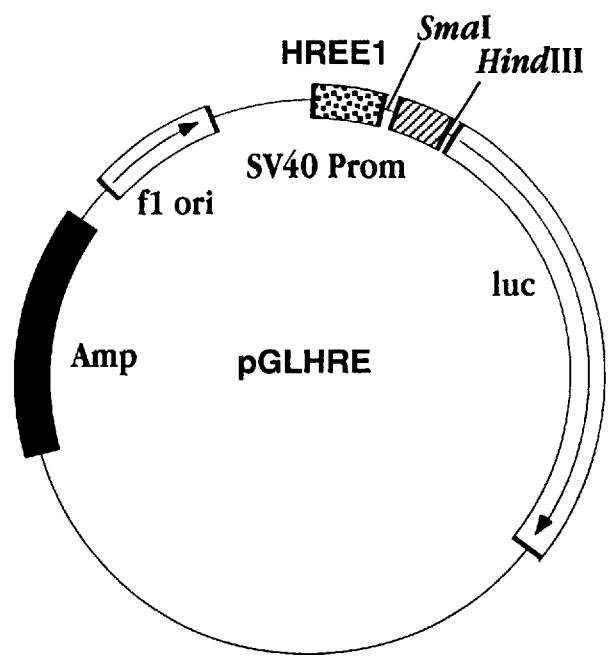
FIGS. 3A and 3B show a schematic diagram of the construction of plasmid pGLαMHC$_{1,2}$HRE (FIG. 3B) from plasmid pGLHRE (FIG. 3A).

(i). HREE1/luc Constructs with Different Tissue-Specific Promoters. Plasmid pGLHRE (FIGS. 1B, 2A, 3A) was made by blunt-ligating the 240 bp HREE1 fragment (SEQ ID NO:6) into the SmaI site of the MCS of pGL2PV (FIG. 1A).

Figure 2D:
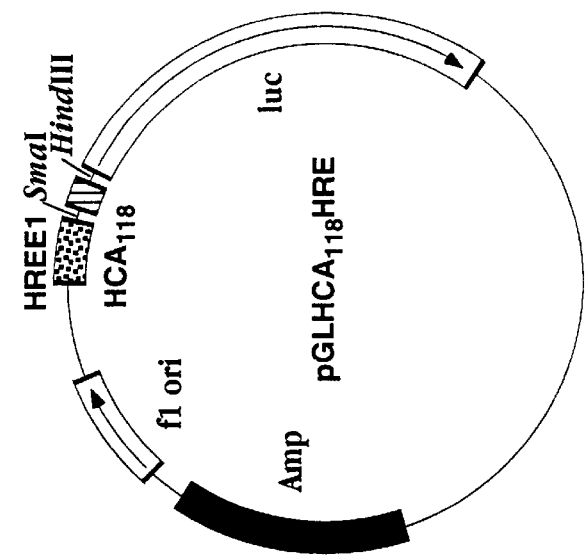
Figure 2C:
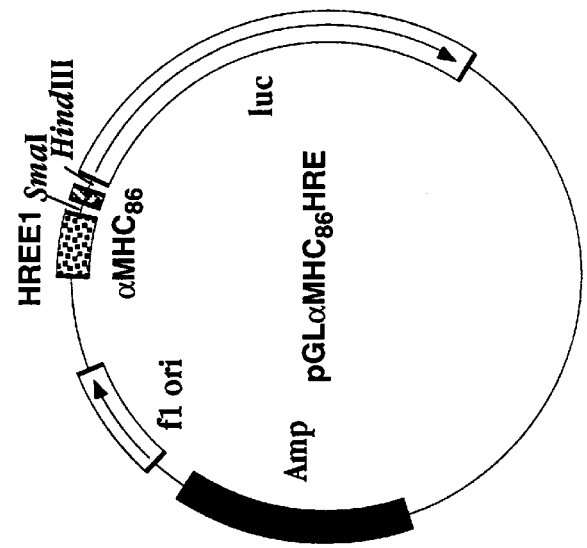
Figure 2B:
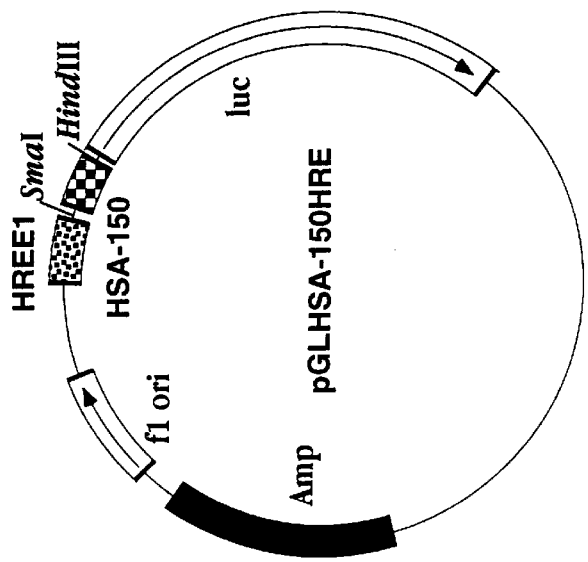

Plasmid pGLHSA-150HRE (FIG. 2B) was made by digesting pGLHRE with HindIII and SmaI to drop out the SV40 promoter and replacing it with a 150 bp HindIII-SmaI fragment from pHSA-150CAT containing a fragment of the human skeletal actin (HSA) promoter.

Plasmid pGLαMHC$_{86}$HRE (FIG. 2C) was made by digesting pGLHRE with HindIII and SmaI to drop out the SV40 promoter and replacing it with a 120 bp HindIII-EcoRI fragment from pαMHC$_{86}$CAT containing 86 bp (SEQ ID NO:24) of the human α-myosin heavy chain (α-MHC) promoter. The EcoRI end of the 120 bp fragment was filled in with DNA polymerase I using standard methods (Sambrook, et al.) before blunt end ligation to the vector SmaI site.

Plasmid pGLαMHC$_{86}$-GATA-HRE was made by cloning a 36 bp oligonucleotide (SEQ ID NO:1; described above), containing a duplicated GATA 4 box into the HindIII site (filled in with polymerase) of plasmid pGLαMHC$_{86}$HRE, upstream of the 86 bp promoter fragment.

Plasmid pGLHCA$_{118}$HRE (FIG. 2D) was made by digesting pGLHRE with HindIII and SmaI to drop out the SV40 promoter and replacing it with a 188 bp HindIII-EcoRI fragment from pHCA$_{118}$CAT, containing 118 bp of the human cardiac actin (HCA) promoter plus 70 bp of actin exon 1. The EcoRI end of the 188 bp fragment was filled in with DNA polymerase I as above before blunt end ligation to the vector SmaI site.

Figure 3B:
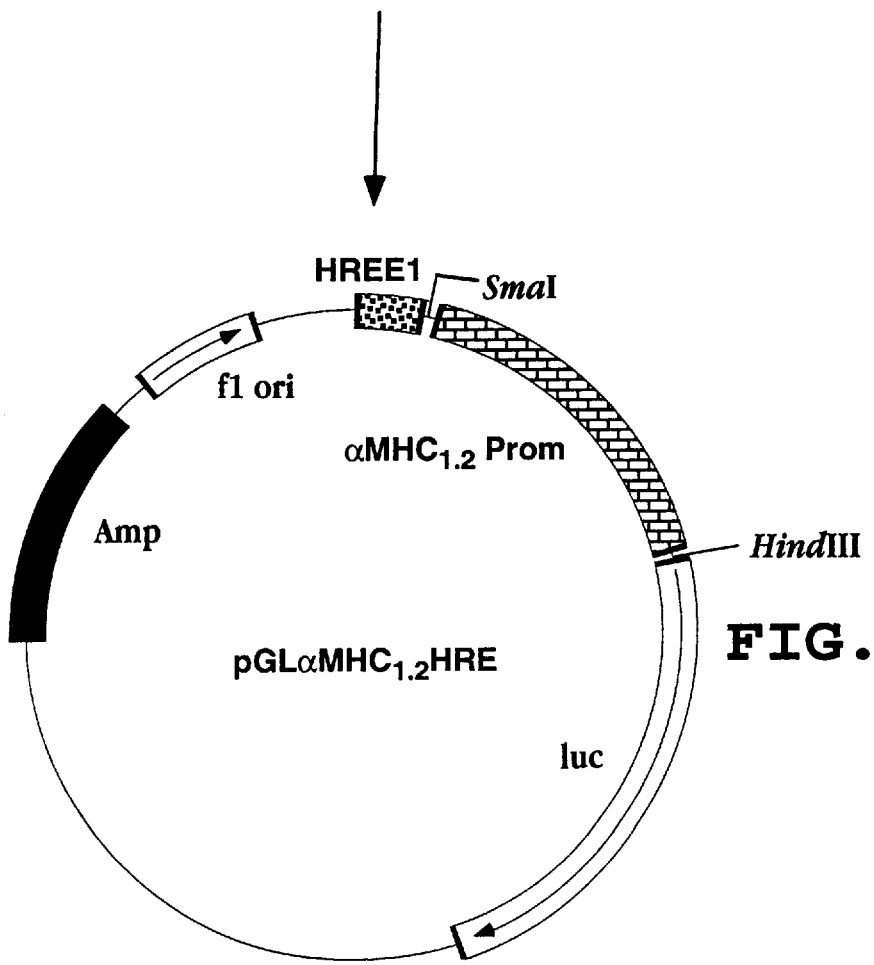

Plasmid pGLαMHC$_{1.2}$HRE (FIG. 3B) was made by digesting pGLHRE with HindIII and SmaI to drop out the SV40 promoter and replacing it with a 1.2 kb HindIII-EcoRI fragment from pαMHC$_{2.0}$CAT containing 1.2 kb of the human α-MHC promoter. The EcoRI end of the 1.2 kb fragment was filled in as above in prior to cloning.

Figure 6A:
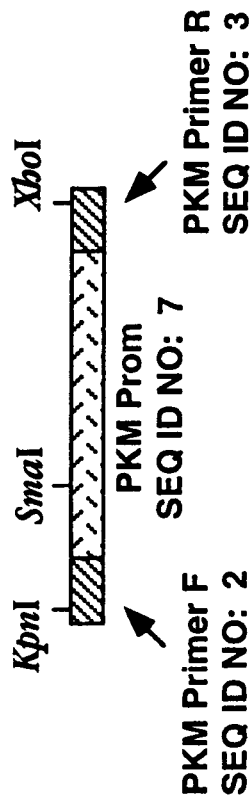
Figure 6B:
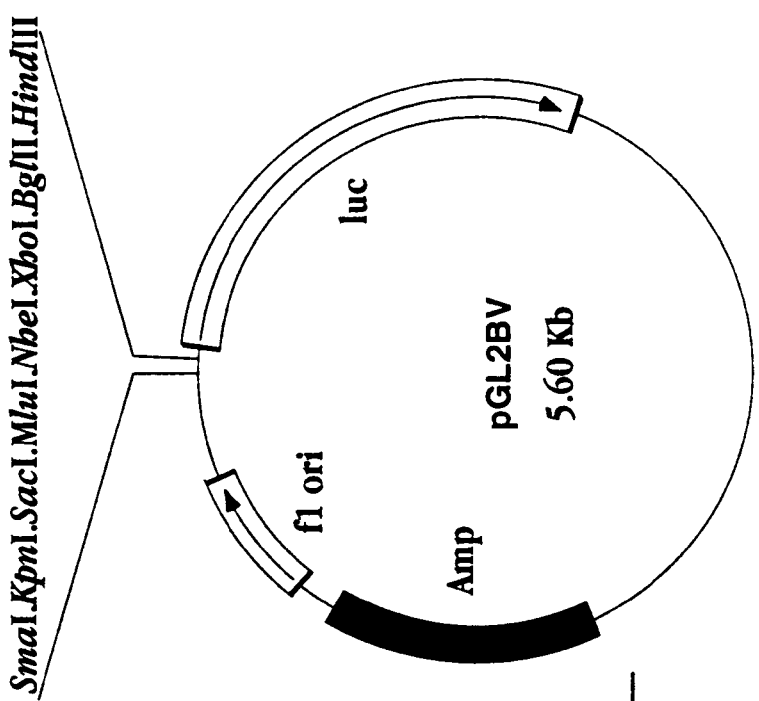

(ii). PKM Promoter/luc Constructs. Plasmid pGLPKM$_{460}$, containing 460 bp of the rat muscle specific pyruvate kinase (PKM) gene promoter and 140 bp of the PKM coding sequence (SEQ ID NO:7), was created using polymerase chain reaction (PCR) as follows. PKM-specific primers containing endonuclease restriction sites near their 5' end were designed based on the nucleotide sequence of the PKM gene (Takenaka, et al., 1989). PKM primer F (SEQ ID NO:2) contained a KpnI site, while PKM primer R (SEQ ID NO:3) contained a XhoI site. PCR was carried out using the above primers and 1 μg of rat heart genomic DNA as a template for 25 cycles using standard procedures and a Perkin-Elmer (Norwalk, Conn.) DNA thermal cycler. The PCR product (FIG. 6A) was purified by agarose gel electrophoresis, cut with KpnI and XhoI, and cloned into KpnI/XhoI cut pGL2BV (FIG. 6B; Promega Corp., Madison, Wis.), generating pGLPKM$_{460}$ (FIG. 6C).

Plasmid pGLPKM$_{285}$ (FIG. 6E) was generated by digesting pGLPKM$_{460}$ with SmaI to drop out the −460 to −285 portion of the promoter, and religating the vector. pGLP-KMD (FIG. 6D) was generated by digesting pGLPKM$_{460}$ with SmaI to isolate the −460 to −285 portion of the promoter, and cloning that fragment into pGL2PV (Promega Corp.) that had been cut with SmaI.

Figure 7C:
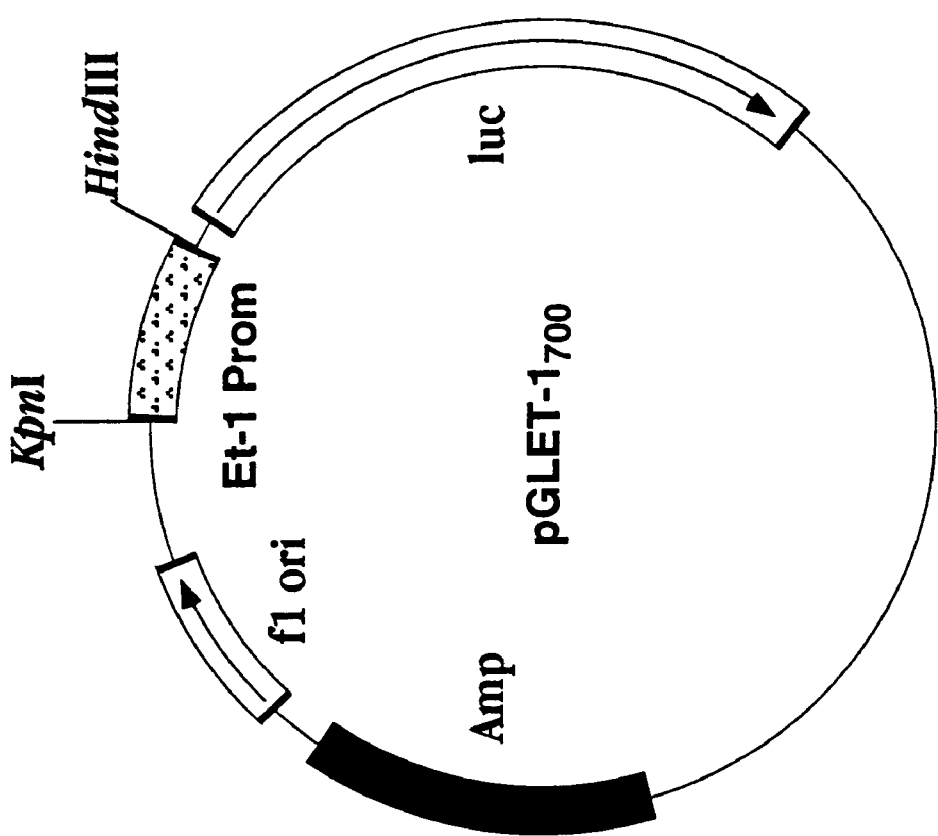

(iii). Et-1 Promoter/luc Constructs. Plasmid pGLET-1$_{700}$ (FIG. 7C), containing 700 bp of the human ET-1 gene promoter (SEQ ID NO:8), was created using PCR to amplify HeLa cell genomic DNA as described above. ET-1 specific primers were designed based on the promoter sequence (Inoue, et al., 1989) of the ET-1 gene. The forward primer (SEQ ID NO:4) contained PstI and KpnI sites, while the reverse primer (SEQ ID NO:5) contained HindIII and XbaI sites. The PCR product (FIG. 7A) was purified by gel electrophoresis, cut with KpnI and HindIII, and cloned into KpnI/HindIII cut pGL2BV (FIG. 7B; Promega Corp.).

(iv). ENO3 Promoter/luc Constructs. Plasmid pGLENO$_{628}$ was constructed by cloning a blunt ended genomic DNA containing an ENO3 promoter fragment (−628 to +63; SEQ ID NO:29), isolated from a lambda gt10 human genomic library, into the SmaI site of pGL2BV.

Figure 4A:
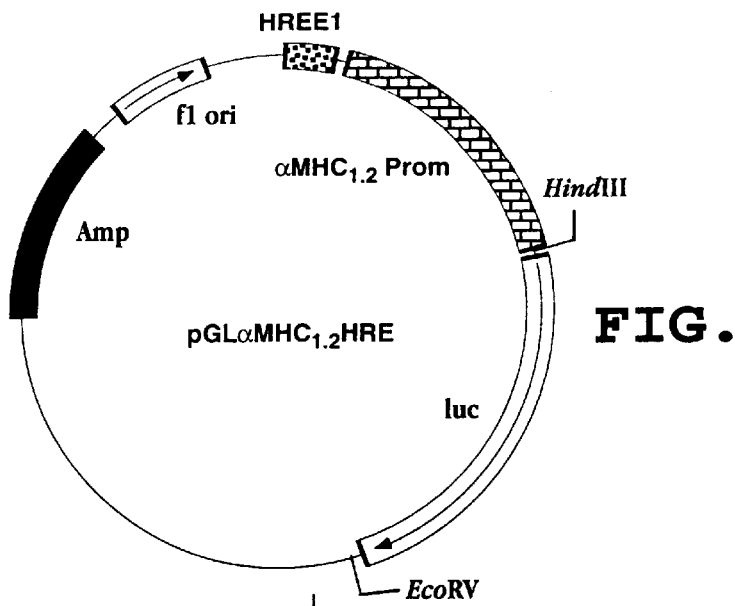
FIGS. 4A and 4B show a schematic diagram of the construction of plasmid pGLαMHC$_{1,2}$HRE-NOS (FIG. 4B) from plasmid pGLαMHC$_{1,2}$HRE (FIG. 4A).
Figure 4B:
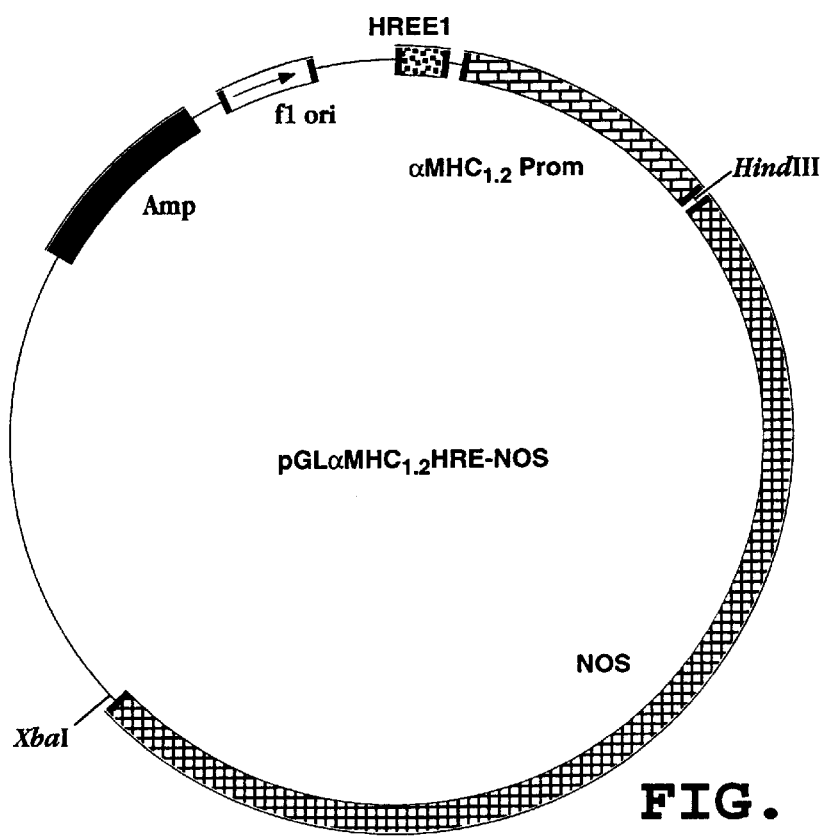

(v). Therapeutic Gene Constructs. Plasmid pαMHC$_{1.2}$HRE-NOS (FIG. 4B) was made by digesting plasmid pGLαMHC$_{1.2}$HRE (FIG. 4A) with HindIII and EcoRV to drop out the luciferase cDNA and replacing it with a HindIII/XbaI fragment from pNOS containing a full length NOS CDNA.

Figure 5A:
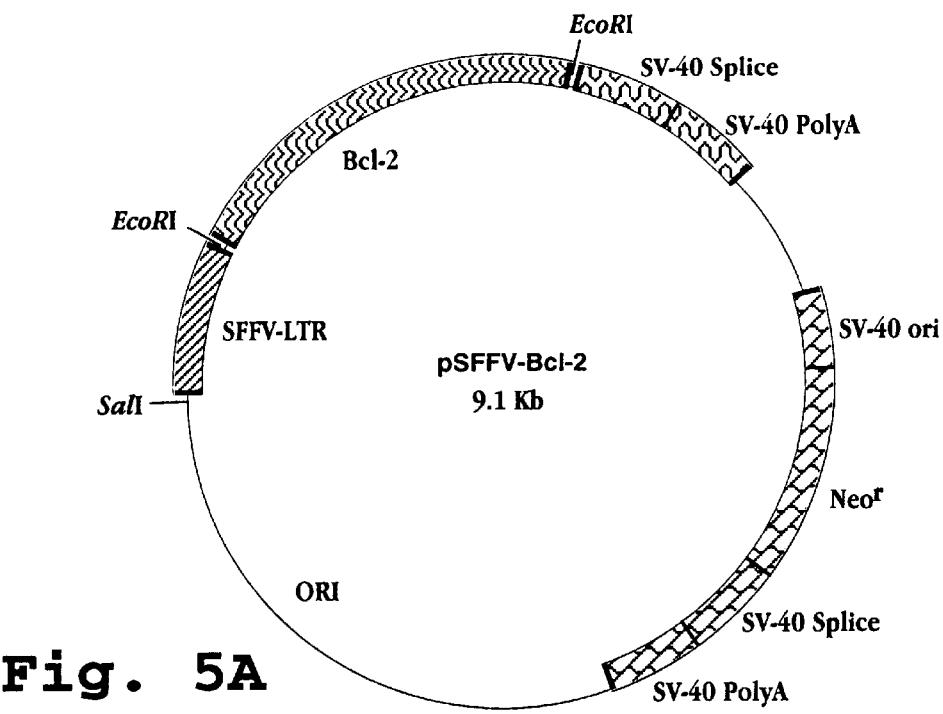
FIGS. 5A and 5B show a schematic diagram of the construction of plasmid pαMHC$_{1,2}$-HRE-Bcl-2 (FIG. 5B) from plasmid pSFFV-Bcl-2 (FIG. 5A).
Figure 5B:
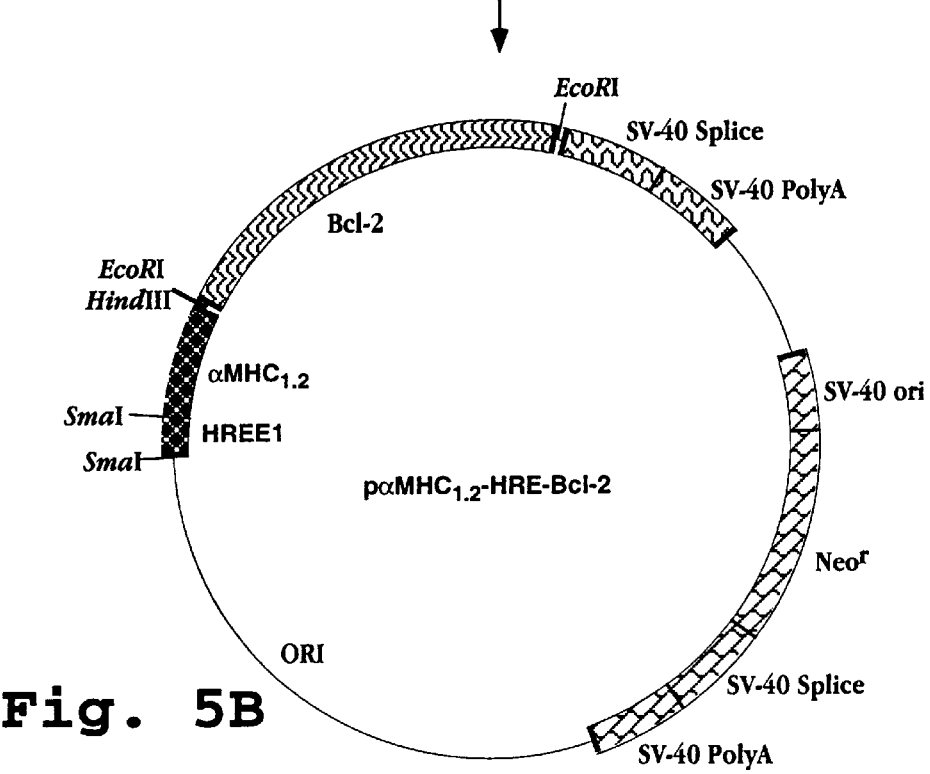

Plasmid pαMHC$_{1.2}$HRE-Bcl-2 (FIG. 5B) was made by digesting pSFFV-Bcl-2 with SalI, blunting the vector as described above, removing the SFFV promoter from the linearized vector with an EcoRI digest, and replacing the SFFV promoter with a SmaI/EcoRI fragment from pgLαMHC$_{1.2}$HREE containing the 1.2 kb αMHC promoter fragment and the 240 bp HREE1.

(vi). Other Plasmid Constructs. Plasmid pαMHC$_{5.5}$HRE-CAT was made by inserting the 240 bp HREE1 immediately 5' of the αMHC promoter of pαMHC$_{5.5}$CAT.

(vii). Adenoviral Constructs. Adenoviral constructs are made using standard methods (e.g., Friedman,, et al., 1986; Hertz and Gerard, 1993), as follows.

Construct AdαMHC1.2Bcl2HREE is made by inserting a 3.34 Kb EcoRI/HindIII fragment from pαMHC1.2-Bcl-2 (containing 1.2 Kb of the α-MHC promoter, 1.9 Kb Bcl-2 cDNA, and 240 bp HREE1) into pAPLCMV digested with EcoRI and HindIII to drop out the CMV promoter and CAT gene. pAPLCMV, which may be obtained from Dr. Larry Kedes (University of Southern California, Los Angeles, Calif.; Kass-Eisler, et al., 1993), is a base replication deficient adenoviral expression vector. The backbone adenoviral vector for recombination, p9M17, may also be obtained from Dr. Larry Kedes.

Recombinant pAPLCMV (pAdαMHC1.2bcl-2HRE) and p9M17 are used to co-transfect 293 cells (ATCC) to propagate the adenovirus.

EXAMPLE 1

Tissue Specific Hypoxia Induced Expression In Vitro

Constructs pGLHRE, pGLHSA-150HRE, pαMHC$_{5.5}$HRE-CAT, pGLαMHC$_{1.2}$HRE, pGLHCA$_{118}$HRE and pGL-Eno$_{628}$ were tested for tissue-specific expression and hypoxia inducibility in HeLa cells, Hep G2 cells, differentiated C2C12 muscle myotubes, and cardiac myocytes.

A. Buffers and Solutions

HEPES buffered saline (HeBS; 2X solution)

16.4 g NaCl
11.9 g HEPES acid
0.21 g Na$_2$HPO$_4$
H$_2$O to 1 liter
Titrate Ph to 7.05 with 5M NaOH.
PBS Buffer

| | |
|---|---|
| 137 mM | NaCl |
| 2.7 mM | KCl |
| 4.3 mM | Na$_2$HPO$_4$ |
| 1.4 mM | KH$_2$PO$_4$ |

Adjust pH to 7.1.
Reconstituted Luciferase Assay Reagent (LAR)

| | |
|---|---|
| 20 mM | Tricine |
| 1.07 mM | (MgCO$_3$)$_4$MG(OH)$_2$ · 5H$_2$O |
| 2.67 mM | MgSO$_4$ |
| 0.1 mM | EDTA |

-continued

| A. Buffers and Solutions | |
|---|---|
| 33.3 mM | DTT |
| 270 μM | coenzyme A |
| 470 μM | luciferin |
| 530 μM | ATP |
| Cell Culture Lysis Reagent (CCLR; 1X Solution) | |
| 25 mM | Tris-phosphate, pH 7.8 |
| 2 mM | DTT |
| 2 mM | 1,2-diaminocyclohexane-N,N,N',N'-tetraacetic acid |
| 10% | glycerol |
| 1% | Triton X-100 |

B. Cell Transfection

HeLa cells, C2C12 myocytes, and cardiac myocytes were transfected with the indicated plasmid DNA by the standard calcium phosphate procedure (Ausubel, et al.).

Briefly, $10^5$ cells were plated on a 10-cm tissue culture dish and grown for 3 days. The cells were split 1:10 into 10 ml of medium one day before application of plasmid DNA. DNA for transfection was prepared by resuspending an ethanol-precipitated pellet containing 20 μg of the plasmid DNA in 450 μl ddH$_2$O and adding 50 μl of 2.5 mM CaCl$_2$.

500 μl of 2× HeBS were added to a 15 ml conical centrifuge tube, and the solution was aerated by bubbling air with a 10 ml pipette attached to an automatic pipettor (Drummond Instruments, Fisher Scientific, Pittsburgh, Pa.). The DNA/CaCl$_2$ solution was added dropwise, and the resultant mixture was vortexed for 5 seconds and then allowed to sit for 20 minutes at room temperature to form precipitate.

The precipitate was added to the dishes containing the cells and the dishes were incubated overnight.

The cells were washed twice with 5 ml PBS and fed with 10 ml of complete medium. The cells were then allowed to recover for 24 hours before incubation under an atmosphere of 1.0% O$_2$, 5% CO$_2$, 94% N$_2$ for an additional 20 hours.

C. Exposure to Hypoxic Conditions

Two to three days after transfection, the cells were exposed to atmospheric oxygen (approximately 21% O$_2$, 5% CO$_2$, balance N$_2$; pO$_2$=~160 mmHg), or to hypoxic conditions (approximately 0.5–2.0% O$_2$, 5% CO$_2$, balance N$_2$; pO$_2$=~4–8 mmHg) in an environmental chamber (Anaerobic Systems, San Jose, Calif., U.S.A.) which was equipped with a Nikon TMS microscope and a continuous readout oxygen electrode (Controls Katharobic, Philadelphia, Pa., U.S.A.). Unless otherwise indicated, the cells were kept in the chambers for one day prior to assaying for luciferase expression.

D. Luciferase Expression

Cells transfected and treated as above were assayed for expression of the luciferase enzyme using a standard reaction protocol (Titus). Briefly, 1 ml of CCLR and 1 ml of LAR were allowed to equilibrate at room temperature. The culture medium in the dish containing the cells to be assayed was removed and the cells were rinsed twice in PBS buffer.

Approximately 300 μl of the room-temperature CCLR was added to the dish containing the cells, and the dish was incubated at room temperature for 10–15 minutes. The cells were then scraped off the bottom of the culture dish, and the solution containing the cells was transferred to a microcentrifuge tube. The tube was centrifuged in a table-top microcentrifuge briefly (about 5 seconds) to pellet large debris.

20 μl of the supernatant (cell extract) were mixed with 100 μl of LAR at room temperature, and the light produced was measured for a period of 5 minutes, starting approximately 5 seconds after mixing, with a model #1250 LKB luminometer (Bioorbit, Gaithersburg, Md.).

E. Results

Data from HeLa, C2C12, and cardiac cells are given in Table 1, below. Values, presented in arbitrary units, represent averages of three or more experiments for each condition.

TABLE 1

REGULATED EXPRESSION OF UBIQUITOUS- MUSCLE-
AND CARDIAC-SPECIFIC PROMOTERS BY HYPOXIA

| | GL2PV | | GLHRE | | GLHSA$_{150}$HRE | | αMHC$_{1.2}$HRE | | GLHCA$_{118}$HRE | | GLENO$_{628}$ | |
|---|---|---|---|---|---|---|---|---|---|---|---|---|
| | A | Hx | A | Hx | A | Hx | A | Hx | A | Hx | A | Hx |
| HeLa | 18 | 27 | 56 | 387 | BG | | BG | | BG | | — | |
| C2C12 | 189 | 204 | 350 | 1680 | 46 | 278 | BG | | 48 | 248 | 320 | 1560 |
| Cardiac | 24 | 27 | 22 | 165 | 18 | 94 | 21 | 85 | 38 | 263 | 210 | 1610 |

BG—Background

Data shown in the table demonstrate that (i) none of the tested constructs carrying tissue-specific promoters are expressed above background in fibroblast-derived HeLa cells under either normal or hypoxic conditions, (ii) cells containing constructs having HREE1 and a compatible promoter (including the SV40 and tissue-specific promoters) express the reporter at levels that are ~5 to ~7 times greater under hypoxic conditions than under aerobic conditions; (iii) the HREE1 element is equally active in different cells and independent of the promoter; (iv) the α-MHC$_{1.2}$ promoter expresses in cardiac, but not in skeletal or fibroblast-derived cells, the HCA$_{118}$ promoter expresses in both cardiac and skeletal muscle cells, but not in fibroblast-derived cells, and the HSA$_{150}$ promoter expresses in both skeletal and cardiac muscle, with stronger expression in skeletal muscle; and (v) basal (aerobic) expression from α-MHC$_{1.2}$ HCA$_{118}$, and HSA$_{150}$ promoters is weak.

These results indicate that the HREE1 element is fully functional when fused to muscle and cardiac specific promoters and that muscle and cardiac cells are fully responsive to hypoxia in terms of the regulation of these promoters, and suggest that the αMHC$_{1.2}$ propoter is an exemplary promoter for moderate levels of cardiac-specific expression.

The data also show that both the HREE present in the ENO3 promoter and HREE1, when present in constructs with the SV40 promoter, result in comparable levels of hypoxia induction in skeletal muscle cells. In cardiac cells, however, constructs containing the ENO3 HREE are expressed at significantly higher levels than those containing HREE1. Further, hypoxia increases the level of expression of the ENO3 HREE containing constructs in cardiac cells by over seven-fold, as compared with less than 5-fold in skeletal muscle cells. Plasmid pGLENO$_{628}$ confers induced expression in C2C12 myotubes and cardiac myocytes that is at least equivalent to four copies of the erythropoietin HRE (HREE1) in these cells. These results suggest that the HRE in the ENO3 promoter fragment may be a particularly effective HREE for hypoxia induction in constructs targeted with a tissue-specific promoter to cardiac or skeletal muscle cells.

EXAMPLE 2

Tissue Specific Hypoxia Induced Expression In Vivo Following Injection of Constructs Into Target Animal Tissue Constructs of the present invention were injected directly into cardiac tissue using techniques described in Buttrick, et al., (1992) and Buttrick, et al., (1993). Briefly, adult female Wistar rats were anesthetized with an intraperitoneal injection of chloral hydrate (0.7 ml/100 g of a 4% solution). Cardiac injections were made directly into the apex of the heart through a lateral thoracotomy, after which the heart was replaced in the chest, the rats were briefly hyperventilated, and the incision closed. Fifty microliters of a DNA solution containing 2 µg/µl of either pGLHRE or pGLHCA$_{118}$HRE in 20% sucrose and 2% Evans blue were injected through a 27-gauge needle. Following injection the rats were subjected to a 20 min ischemia by cannulation of the coronary artery as described by Smith, et al. (1988).

Hypoxia-inducibility of vector expression was assayed as follows. Hearts were excised approximately 20 hours after the induced ischemia and the ventricles were washed with ice-cold phosphate buffered saline (PBS). The tissue was suspended in 1 ml of ice-cold PBS containing 20% sucrose and homogenized with a Polytron (Kinematica, Switzerland) for 45 sec. After centrifugation at 10,000×g for 10 min supernatants were analyzed for luciferase expression by the assay method described above. Protein was measured using a BioRad assay kit (BioRad Laboratories, Hercules, Calif.).

The results of the experiments are shown in Table 2, below. Luciferase expression in hearts from rats injected with pGLHRE or pGLHCA$_{118}$HRE and subjected to ischemia was approximately 2-fold higher than expression in hearts from control animals injected with saline (n=3).

TABLE 2

ISCHEMIA INDUCIBLE EXPRESSION OF pGLHRE AND pGLHCA$_{118}$HRE IN RAT HEART

| | Luciferase Activity Light Units/mg Protein | |
|---|---|---|
| Plasmid | Aerobic | 20 min. Ischemic |
| pGLHRE | 1180 | 2440 |
| pGLHCA$_{118}$HRE | 88 | 127 |
| Control | 15 | 21 |

Rat hearts were injected with plasmids as described above. A 20 min. ischemia was imposed on one group (3 rats) and the other (1 control) was sham operated. Tissue samples were harvested and assayed for luciferase expression 20 hr. later.

These results indicate that the direct injection of plasmid DNA, made in accordance with the teachings of the present specification, into hearts of living mammals is effective to result in the expression of genes carried on those plasmids. Further, these results indicate that expression vectors carrying chimeric genes of the present invention are effective to result in significantly increased levels of expression in response to hypoxia caused by ischemia in vivo.

EXAMPLE 3

Stable Expression of Hypoxia Regulated NOS and Bcl-2 Genes In Vitro $10^6$ C2C12 myoblasts were cotransfected with pSV2Neo (Minty and Kedes) and a test plasmid at a ratio of 1:19 (1 µg pSV2Neo+19 µg test plasmid) using standard methods (Minty and Kedes, 1986). Test plasmids were pGLHRE, pGLHCA$_{118}$HRE, pGLαMHC$_{1.2}$HRE, pSFFV-Bcl-2, and pNOS-HRE. Cultures were selected on day 2 following transfection with 400 µg/ml of the neomycin drug G418 (Gibco/BRL). Colonies of cells resistant to G418 appeared after 10 to 14 days. The resistant cells were pooled. Mass cultures were assayed for the expression of luciferase as described above or by Northern blot assay (Webster, et al., 1993) for the expression of Bcl-2 or NOS RNA. Stable lines were positive for expression of the transfected genes.

Mass cultures were subjected to differentiation conditions by transferring them to low mitogen medium (DMEM with 2% horse serum) and were analyzed visually for differentiation into myotubes. There was no apparent difference between transfected and control cells. Approximately 40% of cells were fused into multinucleate myotubes after 24 h in low mitogen medium. All cultures contained approximately 74% myotubes after 48 h.

Reporter-transfected cells differentiated normally and respond to hypoxia with the predicted induction of reporter. NOS-transfected cells appeared normal both during the hypoxia and during subsequent reoxygenation. A stable line of C2C12 cells that constitutively over-expresses Bcl-2 (without HREE1) was also constructed as described above, and the cells showed normal growth and differentiation characteristics.

Taken together, the data presented above suggest that inclusion of HRE elements, Bcl-2 over-expression, and hypoxia-induced over-expression of NOS is not toxic to muscle cells in vitro. Further, the data indicate that the cells may be protected from the deleterious effects of hypoxia by the expression of therapeutic genes (e.g., NOS).

EXAMPLE 4

Expression of pGLPKM Plasmids Under Hypoxic Conditions

Plasmid pGLPKM$_{460}$ was transfected into C2C12 cells and cardiac myocytes and assayed for luciferase activity as described in Example 1. The expression of pGLPKM in both transfected C2C12 myotubes and neonatal cardiac myocytes was increased by 6±2 fold (n=4) in both cell types by incubation of the cells in an atmosphere containing 0.5 % $O_2$, 5% $CO_2$, balance $N_2$ (hypoxic conditions) relative to normal conditions, as described in Example 1.

A portion of this HRE element, obtained by digesting with SmaI to cut at an internal SmaI site, is also effective as a hypoxia response enhancer element. This fragment, termed HREPKM$_{285}$, confers hypoxia-induced expression in C2C12 myotubes and cardiac myocytes similar to that obtained with pGLPKM$_{460}$. This level of hypoxia induction is at least equivalent to that obtained using HREE1 (SEQ ID NO:6).

These results indicate that the PKM promoter fragment contained in the sequence represented as SEQ ID NO:7 contains an HRE element that is effective at enhacing the expression of chimeric genes containing the element under conditions of hypoxia.

The PKM promoter sequence has no significant homology with the erythropoietin HRE consensus, but does share a consensus sequence (SEQ ID NO:31) with the ENO3 promoter fragment (SEQ ID NO:29). This consensus, located approximately 88 bp upstream of the transcription start site of PKM and approximately 70 bp upstream of the transcription start site of ENO3, may represent an important element for conferring enhancement of expression in response to hypoxia.

EXAMPLE 5

Expression of pGLET-1$_{700}$ Plasmids Under Hypoxic Conditions

Plasmid pGLET-1$_{700}$ was transfected into human arterial endothelial cells as described in Example 1. The expression of pGLET-1$_{700}$ in these cells was increased 5 fold by incubation of the cells in a hypoxic atmosphere as described above. No significant induction of pGLET-1$_{700}$ was observed in any other cell types tested, including HeLa, C2C12, and cardiac myocytes. Elements contained within the 700 bp sequence have no significant homology with the erythropoietin HRE consensus.

These results indicate that the 700 bp fragment of the human ET-1 gene promoter corresponding to the sequence represented herein as SEQ ID NO:8 is effective to (i) restrict expression of genes under its control to the vascular endothelium, and (ii) confer hypoxia-inducibility on the expression of those genes. Accordingly, this fragment, in conjunction with a therapeutic or reporter gene, may be used in the methods of the present invention to both target expression to a selected tissue (vascular endothelium), and confer enhancement of expression by hypoxia.

EXAMPLE 6

Regulation of the Human Metallothionein IIa (hMTIIa) Promoter by Hypoxia

Three DNA fragments derived from the human MTIIa (hMTIIa) promoter, were tested in chloramphenicol acetyl-transferase (CAT) reporter gene assays for hypoxia responsiveness. Fragments containing −760 bp (SEQ ID NO:32) and −345 bp (SEQ ID NO:33) of the promoter (including the first +21 bp downstream of the transcription initiation site) were cloned immediately upstream of the bacterial chloramphenicol acetyl transferase (CAT) gene in the pCAT Basic reporter vector (Promega, Madison, Wis., U.S.A.), generating vectors pCAT-760 and pCAT-345, respectively. These vectors were in turn used to transfect A431 cells (ATCC Accession # CRL-7907) using the standard calcium phosphate method (Ausubel, et al.).

Approximately four days after transfection, the transfected cells were exposed to a selection medium comprised of Dulbecco's modified Eagle's medium (DMEM) supplemented with 10% fetal bovine serum and containing 400 μg/ml G418 to select stable clones (the PCAT Basic vector contains a G417/neomycin resistance gene).

Early passages (1–10) of pooled stable clones were used in hypoxia experiments. Three hours before exposure to hypoxia, the medium bathing the cultures was changed. The dishes were placed inside specially designed aluminum chambers submerged in a 37° C. water bath and attached to a 5% $CO_2/N_2$ manifold on a vacuum line (Laderoute, et al., 1992). Oxygen was extracted at 37° C. over 1.5 hours by 7 cycles of pumping to a fixed pressure followed by filling with 5% $CO_2/N_2$. The final $O_2$ tension in the gas phase was approximately 0.01% of atmospheric $O_2$ ($pO_2$<0.08 torr)

Following incubation at 37° C. for the indicated time (up to 14 hours), the chambers were opened under 5% $CO_2/N_2$ in a humidified anaerobic chamber (Anaerobic Systems, San Jose, Calif.). Aerobic controls were incubated for an equal time period in 5% $CO_2$/air at 37° C.

Total protein for CAT assays was harvested as cell lysates using the Triton X-100 method (Laderoute, et al., 1992) in the humidified anaerobic chamber following 8 or 14 hr of hypoxia. The CAT assays were conducted using standard methods (Ausubel, et al.). Briefly, Acyl CoA and $^{14}$C-labeled chloramphenicol were added to the cell lysates, and modified derivatives of the chloramphenicol were separated from the starting material using thin-layer chromatography. The CAT activity of the extracts was quantitated using the following formula:

$$\% \text{ acetylated} = \frac{\text{counts in acetylated species}}{\text{counts in acetylated species} + \text{counts in nonacetylated chloramphenicol}}$$

Table 3, below, presents CAT activity data for the −345 bp fragment. The numbers represent the amount of CAT activity in extracts from transfected cells exposed to hypoxia divided by the CAT activity in extracts from transfected cells under normoxic conditions. The hypoxia-regulated transcriptional activation is compared with that caused by cadmium chloride (10 μM), a known activator of hMTIIa transcription (Karin and Herrlich 1989).

TABLE 3

Characterization of a Hypoxia-Responsive Element (HRE) in the Promoter of the Human Metallothionein IIa Gene

| Time (hours) | Transcriptional Activation |
|---|---|
| CAT (hypoxia)/CAT air | |
| 8 | 1.8 ± 0.8[a] |
| 14 | 2.7 ± 0.2[b] |
| CAT Cd/CAT (control) | 3.9 ± 1.3[b] |

[a]Sample SD; n = 4
[b]Sample SD; n = 7

These results indicate that hypoxic stress can increase transcription from the hMTIIa proximal promoter. Enhancements in CAT activity relative to the aerobic controls were observed at both 8 and 14 hr of hypoxia. The levels of induction (2–3 fold) were within the same range as those found in the cadmium chloride-treated positive controls. Hypoxia responsiveness of the 760 bp construct was similar to that of the 345 bp construct.

EXAMPLE 7

Deletion Analysis of hMTIIa Promoter

To further characterize the hMTIIa promoter, mouse C2C12 myoblasts were transiently transfected with PCR-generated nested deletion fragments of the −345 bp responsive fragment. Fragments containing −163 bp (SEQ ID NO:34) and −90 bp (SEQ ID NO:35) of the hMTIIa promoter (including the first +21 bp downstream of the transcription initiation site) were inserted immediately upstream of the luciferase reporter gene of the pGL2 plasmid (Promega, Madison, Wis.), generating pGL2-163 and pGL2-90, respectively. The plasmids were used to transiently transfect the C2C12 cells as described above.

The transfected cells were subjected to hypoxia treatment and cell extracts were made as described above. Luciferase activity of cell extracts was measured using a standard assay (Ausubel, et al.). Briefly, ATP and the substrate luciferin were added to the lysate in a luminometer, and total light output was measured. The amount of light was proportional to the amount of luciferase present in the extracts.

Extracts from both pGL2-163- and pGL2-90-transfected cells showed significant upregulation of luciferase activity under hypoxic conditions, with levels of induction (approximately 3.0-fold) similar to those observed in Example 6, above. These results suggest that at least one HRE is contained in the proximal 90 bp fragment (SEQ ID NO:35) of the hMTIIa promoter.

EXAMPLE 8

Induction of Toxic Genes by hMTIIa HRE In Vitro

The luciferase coding sequence in the pGL3-Basic promoter vector (Promega) is excised as a NcoI/XbaI fragment and replaced with a double-stranded PCR-generated DNA fragment encoding human tumor necrosis factor (hTNF) (SEQ ID NO:37; Shirai, et al.). TNF is a growth factor that rapidly and induces programmed cell death or apoptosis (Cleveland and Ihle, 1995), and is not known to be induced by hypoxic stress. The −90 bp hMTIIa fragment (SEQ ID NO:35) is inserted immediately upstream of the TNF gene, resulting in construct hMTIIa-HRE-TNF.

The construct is used to transfect both C2C12 cells (transient transfection) and A431 cells (stable transfection) as described above. Transfected cells are then subjected to either normoxic or hypoxic conditions for periods of time ranging from 8 to 24 hr as described above, and induced cytotoxicity of the TNF protein is evaluated using a standard clonogenic assay (e.g., as described in Kowk and Sutherland, 1989). Briefly, several dilutions, 3 replicates per dilution, are plated for each time point, and the cells are incubated undisturbed in a humidified 37° C. incubator for 10–20 days. Cell colonies are stained with methylene blue and colonies with 30 or more cells are scored. Northern and Western analyses are performed immediately after hypoxic treatment to determine induction of TNF.

EXAMPLE 9

Hypoxia-Mediated TNF Induction and Tumor Control in an Animal Xenograft Model

To determine the stage at which tumors develop a substantial hypoxia portion, nude mice (Taconic, Germantown, N.Y., U.S.A.) ranging in age from 4–5 weeks, are injected by subcutaneous (s.c.) unilateral injections of about $5 \times 10^6$ exponentially growing untransfected A431 cells into the dorsum of the right side. Hypoxic regions are identified using a derivative of 2-nitroimidazole etanidazole, the fluorinated bioreductive compound 2-(2-nitro-1H-imidazol-1-yl)-N-(2,2,3,3,3-pentafluoropropyl)acetamide (EF5; obtained from Dr. Cameron Koch, Department of Radiation and Oncology, School of Medicine, University of Pennsylvania; Lord, et al., 1993). Etanidazole forms covalent bonds to cellular macromolecules after bioreduction at low oxygen tensions (Lord, et al., 1993). Monoclonal antibodies raised against these nonphysiological adducts (Lord, et al., 1993) are employed using standard immunohistochemistry to image hypoxia regions in serial frozen sections (7 μm) from tumors harvested twice per week.

A. Testing Reporter Constructs In Vivo

Reporter gene constructs containing the luciferase gene under the control of an HRE from the hMTIIa promoter are made as described above and used to stably transfect A431 cells.

Experiments are conducted using three groups of mice, each group injected as described above with one of three types of cells: 1) untransfected cells, 2) stable transfectants containing the empty pGL2 vector and 3) stable transfectants containing the hMTIIA-HRE-pGL2 construct. Groups 1 and 2 are used as negative controls.

The tumors are allowed to grow to a stage at which they contain a substantial hypoxia portion, determined as described above. The mice are then sacrificed, tumors are removed and cut on a cryostat, and the resulting frozen sections are analyzed for luciferase activity and EF5 staining. The degree of overlap between the luciferase activity and EF5 staining in group 3 mice relates to the potential effectiveness of such an HRE-containing construct in a tumor in vivo.

B. Testing Toxic Constructs In Vivo

These experiments are conducted as described above, except that they employ A431 cells transfected with the hMTIIa-HRE-TNF construct or the empty vector (missing both the hMTIIa-HRE and the TNF cDNA). Frozen sections are scored for apoptosis using the "APOTAG" kit (Oncor, Gaitherburg, Md.). Effectiveness of the construct is measured by increased apoptosis in the hypoxic regions of tumors containing the transfected hMTIIa-HRE-TNF construct as compared with tumors containing the empty vector.

While the invention has been described with reference to specific methods and embodiments, it is appreciated that various modifications and changes may be made without departing from the invention.

It is claimed:

1. An isolated DNA construct, comprising:
   a human metallothionein II hypoxia response enhancer element consisting esentially of a sequence selected from the group consisting of SEQ ID NOS:32, 33, 34 and 35, a tissue-specific promoter heterologous to the element, and a desired coding sequence encoding a gene product of interest,
   wherein said promoter is operably linked to said desired coding sequence and said element is effective to modulate expression of said coding sequence.

2. The construct of claim 1, wherein said promoter is a cardiac-specific promoter.

3. The construct of claim 2, wherein said promoter is selected from the group consisting of α-MHC$_{5.5}$ promoter, α-MHC$_{86}$ promoter, and human cardiac actin promoter.

4. The construct of claim 1, wherein said promoter is a kidney-specific promoter.

5. The construct of claim 4, wherein said promoter is a renin promoter.

6. The construct of claim 1, wherein said promoter is a brain-specific promoter.

7. The construct of claim 6, wherein said promoter is selected from the group consisting of aldolase C promoter, and tyrosine hydroxylase promoter.

8. The construct of claim 1, wherein said promoter is a vascular endothelium-specific promoter.

9. The construct of claim 8, wherein said promoter is selected from the group consisting of Et-1 promoter and vonWillebrand factor promoter.

10. The construct of claim 1, wherein said HRE element consists essentially of a sequence of SEQ ID NO:35.

11. The construct of claim 1, wherein said coding sequence is selected from the group consisting of nitric oxide synthase (NOS), Bcl-2, superoxide dismutase (SOD), and catalase.

12. An expression vector comprising the construct of claim 1.

13. The expression vector of claim 12, wherein said expressions vector is a plasmid.

14. The expression vector of claim 13, wherein said expression vector is an adenovirus vector.

15. The expression vector of claim 13, wherein said expression vector is a retrovirus vector or an adenovirus vector.

16. An isolated human metallothionein II hypoxia response enhancer (HRE) element consisting essentially of a sequence of SEQ ID NO:35.

17. An isolated polynuceleotide construct comprising a human metallothioncin II hypoxia response enhancer (HRE) element consisting essentially of a sequence selected from the group consisting of SEQ ID NOS:32, 33, 34 and 35 and a heterologous promoter operably linked to the metallothionein II hypoxia response enhancer (HRE) element.

18. The isolated polynucleotide construct of claim 17, wherein the metallothionein II HRE element consists essentially of SEQ ID NO:35.

19. The isolated polynucleotide construct of claim 17, wherein the polynucleotide further comprises a gene product-encoding polynucleotide operably linked to the promoter.

20. An isolated polynucleotide construct comprising: a human metallothioenin II hypoxia response enhancer (HRE) element consisting essentially of a sequence selected from the group consisting of SEQ ID NOS:32, 33, 34 and 35 operably linked to a tissue-specific promoter heterologous to the HRE element.

21. The polynucleotide construct of claim 20, wherein said promoter is a cardiac-specific promoter.

22. The polynucleotide construct of claim 21, wherein said promoter is selected from the group consisting of α-MHC$_{5.5}$ promoter, α-MHC$_{86}$ promoter, and human cardiac actin promoter.

23. The polynucleotide construct of claim 20, wherein said promoter is a kidney-specific promoter.

24. The polynucleotide construct of claim 23, wherein said promoter is a renin promoter.

25. The construct of claim 24, wherein said promoter is a brain-specific promoter.

26. The polynucleotide construct of claim 25, wherein said promoter is selected from the group consisting of aldolase C promoter, and tyrosine hydroxylase promoter.

27. The polynucleotide construct of claim 24, wherein said promoter is a vascular endothelium-specific promoter.

28. The polynucleotide construct of claim 27, wherein said promoter is selected from the group consisting of Et-1 promoter and vonWillebrand factor promoter.

29. The polynucleotide construct of claim 24, wherein the metallothionein II HRE element consists essentially of a sequence of SEQ ID NO:35.

30. The polynucleotide construct of claim 24, wherein the promoter is a muscle-specific promoter.

31. The polynucleotide construct of claim 24, wherein the promoter is a skeletal muscle-specific promoter.

32. The construct of claim 1, wherein the promoter is a muscle-specific promoter.

33. The construct of claim 1, wherein the promoter is a skeletal muscle-specific promoter.

\* \* \* \* \*

UNITED STATES PATENT AND TRADEMARK OFFICE
CERTIFICATE OF CORRECTION

PATENT NO. : 6,218,179 B1
DATED : April 17, 2001
INVENTOR(S) : Webster, Keith A., et al.

It is certified that error appears in the above-identified patent and that said Letters Patent is hereby corrected as shown below:

Column 130,
Line 36, please change "13" to -- 12 --.
Line 38, please change "13" to -- 12 --.
Line 45, please change "metallohioncin" to -- metallothionein --.

Column 131,
Line 5, please change "24" to -- 20 --.

Column 132,
Lines 1, 4 and 6, please change "24" to -- 20 --.

Signed and Sealed this

Twenty-sixth Day of November, 2002

Attest:

JAMES E. ROGAN
Attesting Officer
Director of the United States Patent and Trademark Office

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: GATA4 Enhancer (xi) SEQUENCE DESCRIPTION: SEQ ID NO:1:

CAAAGGGCCG ATGGGCAGAT AGAGGAGAGA CAGGA                       35

(2) INFORMATION FOR SEQ ID NO:2:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PKM primer F (xi) SEQUENCE DESCRIPTION: SEQ ID NO:2:

AATTGGTACC CGGGCGAGCG CCGGGAGGGT GGA                         33

(2) INFORMATION FOR SEQ ID NO:3:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: PKM primer R (xi) SEQUENCE DESCRIPTION: SEQ ID NO:3:

TTAACTCGAG GCACTATGGC ATTGGCTCTG GG                          32

(2) INFORMATION FOR SEQ ID NO:4:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (C) INDIVIDUAL ISOLATE: ET-1 primer F (xi) SEQUENCE DESCRIPTION: SEQ ID NO:4:

TATATCTGCA GGTACCGATA GGGAAAAGAC TGGCATGTGC C                41

(2) INFORMATION FOR SEQ ID NO:5:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: ET-1 primer R (xi) SEQUENCE DESCRIPTION: SEQ ID NO:5:

TATATAAGCT TCTAGAGACC CGTTCGCCTG GCGCGCAGAT GCA                    43

(2) INFORMATION FOR SEQ ID NO:6:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: HREE1 (Hypoxia responsive enhancer
             element 1)

(xi) SEQUENCE DESCRIPTION: SEQ ID NO:6:

CGGGCCCTAC GTGCTGTCTC ACACAGCCTG TCTGACCTCT CGACCTACCG GCCCGGGATC    60

CCGGCCCTAC GTGCTGTCTC ACACAGCCTG TCTGACCTCT CGACCTACCG GCCCGGGATC   120

CCGGCCCTAC GTGCTGTCTC ACACAGCCTG TCTGACCTCT CGACCTACCG GCCCGGGATC   180

CCGGCCCTAC GTGCTGTCTC ACACAGCCTG TCTGACCTCT CGACCTACCG GCCGATCCCG   240

(2) INFORMATION FOR SEQ ID NO:7:

(i) SEQUENCE CHARACTERISTICS:
        (A) LENGTH: 560 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: sequence containing PKM promoter frag.

(xi) SEQUENCE DESCRIPTION: SEQ ID NO:7:

GAGTCACCGG GCGGGCTGG AGGAATGTCC GGGACCTATA AATCTGGGCA ACGCCCTGGT    60

AGGCCAGGGC AGATGGGGCA CCTGGGCAGA ATTCCAAAAT GGGATTATGT AGCCTCTGAG   120

GTCCTAAAGC AACAGGTGGC GGACCACCCG GGGATCTAGG GGTGGTGGCG GCGGTGGACC   180

CGAGGGCGGG TCCTGCCTCC TCACCACTTC CCCATTGGCC ATCAGAATGA CCCATGCGCA   240

ATTTTGGTTT GCAATGTCCT TCCGCCACGG AAGGTAGTCC CCCTCAAAAG GCAACCTGC    300

TTGTCCCGCC TACCCTGCGA CTCTCTCAGA AGGTGCGGGT GCCTGTTGAG AGGCGGGGCT   360

```
CTGCTAGCTC CTGCCCGGAT TGGGCGAGGG GCGGGGCTGC GGAGGGATTG CGGCGGCCCG      420

CAGCAGTGAT AACCTTGAGG CCCAGTCTGC GCAGCCCCGC ACAGCAGCGA CCCGTCCTAA      480

GTCGACAGAC GTCCTCTTTA GGTATTGCAA CAGGATCTGA AGTACGCCCG AGGTGAGCGG      540

GGAGAACCTT TGCCATTCTC                                                 560

(2) INFORMATION FOR SEQ ID NO:8:

(i) SEQUENCE CHARACTERISTICS:
        (A) LENGTH: 713 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: Sequence containing ET-1 promoter (xi) SEQUENCE DESCRIPTION: SEQ ID NO:8:

GATAGGGAAA AGACTGGCAT GTGCCTAAAC GAGCTCTGAT GTTATTTTTA AGCTCCCTTT       60

CTTGCCAATC CCTCACGGAT CTTTCTCCGA TAGATGCAAA GAACTTCAGC AAAAAAGACC      120

CGCAGGAAGG GGCTTGAAGA GAAAAGTACG TTGATCTGCC AAAATAGTCT GACCCCCAGT      180

AGTGGGCAGT GACGAGGGAG AGCATTCCCT TGTTTGACTG AGACTAGAAT CGGAGAGACA      240

TAAAAGGAAA ATGAAGCGAG CAACAATTAA AAAAAATTCC CCGCACACAA CAATACAATC      300

TATTTAAACT GTGGCTCATA CTTTTCATAC CAATGGTATG ACTTTTTTTC TGGAGTCCCC      360

TCTTCTGATT CTTGAACTCC GGGGCTGGCA GCTTGCAAAG GGGAAGCGGA CTCCAGCACT      420

GCACGGGCAG GTTTAGCAAA GGTCTCTAAT GGGTATTTTC TTTTTCTTAG CCCTGCCCCC      480

GAATTGTCAG ACGGCGGGCG TCTGCTTCTG AAGTTAGCAG TGATTTCCTT TCGGGCCTGG      540

CTTATCTCCG GCTGCACGTT GCCTGTTGGT GACTAATAAC ACAATAACAT TGTCTGGGGC      600

TGGAATAAAG TCGGAGCTGT TTACCCCCAC TCTAATAGGG GTTCAATATA AAAAGCCGGC      660

AGAGAGCTGT CCAAGTCAGA CGCGCCTCTG CATCTGCGCC AGGCGAACGG GTC            713

(2) INFORMATION FOR SEQ ID NO:9:

(i) SEQUENCE CHARACTERISTICS:
        (A) LENGTH: 118 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (C) INDIVIDUAL ISOLATE: HCA118 promoter fragment (xi) SEQUENCE DESCRIPTION: SEQ ID NO:9:

CGAAGGGGAC CAAATAAGGC AAGGTGGCAG ACCGGGCCCC CCACCCCTGC CCCCGGCTGC       60

TCCAACTGAC CCTGTCCATC AGCGTTCTAT AAAGCGGCCC TCCTGGAGCC AGCCACCC        118

(2) INFORMATION FOR SEQ ID NO:10:
```

(i) SEQUENCE CHARACTERISTICS:
    (A) LENGTH: 1588 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (C) INDIVIDUAL ISOLATE: Rat alpha MHC promoter fragment (xi) SEQUENCE DESCRIPTION: SEQ ID NO:10:

```
GAATTCTCTT ACTATCAAAG GGAAACTGAG TCATGCACCT GCAAAATGAA TGCCCTCCCT      60
GGACATCATG ACTTTGTCCC TGGGGAGCCA GCACTGTGGA ACTCCAGGTC TGAGAGTAGG     120
AGGCACCCCT CAGCCTGAAG CTGTGCAGAT AGCTAGGGTG TAAAAGAGGG AAGGGGGGAG     180
GCTGGAATGG GAGCTTGTGT GTTCGGAGAC AGGGGACAAA TATTAGGCCC GTAAGAGAAG     240
GTGACCCTTA CCCAGTGTGT TCAACTCAGC CTTTCAGATT AAAAATAACT AAGGTAAGGG     300
CCATGTGGGT AGGGGAGGTG GTGTGAGACG GTCCTGTCTC TCCTCTATCT GCCCATCGGC     360
CCTTTGGGGA GGAGGAAATG TGCCCAAGGA CTAAAAAAGG CCTGGAGCCA GAGGGGCTAG     420
GGCTAAGCAG ACCTTTCATG GGCAAACCTC AGGGCTGCTG TCCTCCTGTC ACCTCCAGAG     480
CCAAGGGATC AAAGGAGGAG GAGCCAGACA GGAGGGATGG GAGGGAGGGT CCCAGCAGAT     540
GACTCCAAAT TTAGGCAGCA GGCACGCGGA ATGAGCTATA AAGGGGCTGG AGCGCTGAGA     600
GCTGTCAGAC CGAGATTTCT CCATCCCAAG TAAGAAGGAG TTTAGCGTGG GGGCTCTCCA     660
ACCGCACCAG ACCTGTCCCA CCTAGAGGGA AAGTGTCTTC CCTGGAAGTG GGCTCCTCCC     720
ACCGGCCTGG GAAGATTCCT CGGTGGGCAG GATGTTCTAC TGGATGCCCC TTCCCTTCCA     780
CTGCCTCCTC CCTCCCTTGT CTTGATTAAT CTTGGCTCTT AGTGTTCAGA AAGATTTGCC     840
CGGTGCTGTC TACTCCATCT GTCTCTACTC TCTCTGCCTT GCCTTCTTGT GTGTTCTCCT     900
TTTCCACGTG TTTCTCACTC CACTGCCTCC CCCCCCCCCT TCATTTTTAT CCTTCCTTTC     960
TTTCTGTGTC AGAATGCTGG GAATCAAACC CAGGGCTTCA TACACGTCAA GTAAGCAATC    1020
TCCCAGTGAG TCAAAGCTTT AATCCTCTGG GTGCTGTCTT ACCGAGCCTC ACTCCCTGTC    1080
TTGTCCTGTT CCGTCCTAGT CAGGATCTCT GGTCCGTCTC TCAGCTTCTG CTACTCCTCT    1140
CCCTGCCTGC TCTTCTCTCC GTCCAGCTGC ACCTCTGTGG CGCTCATTCC AGCCGTGGTC    1200
CAAATTCTCT GTGAAAAGAT TAACCGGGTG AGAATGCCCC CAGTTTCCCC TGTAGACAGC    1260
AGATCATGAT TTTCCCCAGA AGCCAGACTT CCAGCGCCCG CCCTCTGCCC AGCAACTTGA    1320
CACTCTTAGC AAACTTCAGC CACCCTTCCC CCACATAGAC CAAGTCTTGC AGAGAGCCTT    1380
CCTTCAGATG ACTTCGAGTT CTTGCAAAGG AAGGAGAACT CTTTGTGGCG GGGAAGCAGG    1440
CACTTTACAC GGAGTCTGAC GGGAGGTCAT AGGCTATGGC ATAGCAGAGG CAGGGAGGTG    1500
GTGGAATTGG ACTTCGCGCA GAAGCTAAGC ACACACCAGG AATGACATAT CCCTCCTATC    1560
TCCCCCATAA GAGTTTAAGA GTGACAGG                                      1588
```

(2) INFORMATION FOR SEQ ID NO:11:

(i) SEQUENCE CHARACTERISTICS:
    (A) LENGTH: 1679 base pairs
    (B) TYPE: nucleic acid
    (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (C) INDIVIDUAL ISOLATE: Mouse alpha MHC promoter fragment (xi) SEQUENCE DESCRIPTION: SEQ ID NO:11:

```
GAATTCTCTT ACTATCAAAG GGAAACTGAG TCGTGCACCT GCAAAGTGGA TGCTCTCCCT      60

AGACATCATG ACTTTGTCTC TGGGGAGCCA GCACTGTGGA ACTTCAGGTC TGAGAGAGTA     120

GGAGGCTCCC CTCAGCCTGA AGCTATGCAG ATAGCCAGGG TTGAAAGGGG GAAGGGAGAG     180

CCTGGGATGG GAGCTTGTGT GTTGGAGGCA GGGACAGAT ATTAAGCCTG GAAGAGAAGG      240

TGACCCTTAC CCAGTTGTTC AACTCACCCT TCAGATTAAA AATAACTGAG GTAAGGGCCT     300

GGGTAGGGGA GGTGGTGTGA GACGCTCCTG TCTCTCCTCT ATCTGCCCAT CGGCCCTTTG     360

GGGAGGAGGA ATGTGCCCAA GGACTAAAAA AAGGCCATGG AGCCAGAGGG GCGAGGGCAA     420

CAGACCTTTC ATGGGCAAAC CTTGGGGCCC TGCTGTCCTC CTGTCACCTC CAGAGCCAAG     480

GGATCAAAGG AGGAGGAGCC AGGACAGGAG GGAAGTGGGA GGGAGGGTCC CAGCAGAGGA     540

CTCCAAATTT AGGCAGCAGG CATATGGGAT GGGATATAAA GGGGCTGGAG CACTGAGAGC     600

TGTCAGAGAT TTCTCCAACC CAGGTAAGAG GGAGTTTCGG GTGGGGGCTC TTCACCCACA     660

CCAGACCTCT CCCCACCTAG AAGGAAACTG CCTTTCCTGG AAGTGGGGTT CAGGCCGGTC     720

AGAGATCTGA CAGGGTGGCC TTCCACCAGC CTGGGAAGTT CTCAGTGGCA GGAGGTTTCC     780

ACAAGAAACA CTGGATGCCC CTTCCCTTAC GCTGTCTTCT CCATCTTCCT CCTGGGGATG     840

CTCCTCCCCG TCTTGGTTTA TCTTGGCTCT TCGTCTTCAG CAAGATTTGC CCTGTGCTGT     900

CCACTCCATC TTTCTCTACT GTCTCCGTGC CTTGCCTTGC CTTCTTGCGT GTCCTTCCTT     960

TCCACCCATT TCTCACTTCA CCTTTTCTCC CCTTCTCATT TGTATTCATC CTTCCTTCCT    1020

TCCTTCCTTC CTTCCTTCCT TCCTTCCTTC CTTCCTTTCT CCCTTCCTTC CTTCCTTCCT    1080

TCCTTCCTTC CTTCCTTCCT TCCTGTGTCA GAGTGCTGAG AATCACACCT GGGGTTCCCA    1140

CCCTTATGTA AACAATCTTC CAGTGAGCCA CAGCTTCAGT GCTGCTGGGT GCTCTCTTAC    1200

CTTCCTCACC CCCTGGCTTG TCCTGTTCCA TCCTGGTCAG GATCTCTAGA TTGGTCTCCC    1260

AGCCTCTGCT ACTCCTCTTC CTGCCTGTTC CTCTCTCTGT CCAGCTGCGC CACTGTGGTG    1320

CCTCGTTCCA GCTGTGGTCC ACATTCTTCA GGATTCTCTG AAAAGTTAAC CAGGTGAGAA    1380

TGTTTCCCCT GTAGACAGCA GATCACGATT CTCCCGGAAG TCAGGCTTCC AGCCCTCTCT    1440

TTCTCTGCCC AGCTGCCCGG CACTCTTAGC AAACCTCAGG CACCCTTACC CCACATAGAC    1500

CTCTGACAGA GAAGCAGGCA CTTTACATGG AGTCCTGGTG GGAGAGCCAT AGGCTACGGT    1560

GTAAAAGAGG CAGGGAAGTG GTGGTGTAGG AAAGTCAGGA CTTCACATAG AAGCCTAGCC    1620

CACACCAGAA ATGACAGACA GATCCCTCCT ATCTCCCCCA TAAGAGTTTG AGTGACAGA    1679
```

(2) INFORMATION FOR SEQ ID NO:12:

(i) SEQUENCE CHARACTERISTICS:
        (A) LENGTH: 5057 base pairs
        (B) TYPE: nucleic acid
        (C) STRANDEDNESS: double
        (D) TOPOLOGY: linear (ii) MOLECULE TYPE: cDNA to mRNA -continued

```
    (iii) HYPOTHETICAL: NO (iv) ANTI-SENSE: NO (vi) ORIGINAL SOURCE:
         (C) INDIVIDUAL ISOLATE: rat bNOS cDNA (ix) FEATURE:
         (A) NAME/KEY: CDS
         (B) LOCATION: 349..4638

(xi) SEQUENCE DESCRIPTION: SEQ ID NO:12:

ACGTCTGACA AGCTGGTGAC CAAGATGCCC AGAGACTAGA CCCTATGCTT GTGAGTCACA          60

GTCATCAGAC ACGGCAAACC TCCAGTCTTC CTGACCTGTT GCTTAGGGAC ACATCCCGTT         120

GCTGCCCCTG ACGTCTGCCT GGTCAACCTT GACTTCCTTT GAGAGTAAGG AAGGGGCGG          180

GGACACGTTG AAATCATGCC ACCCAAGGCC GAATCGGAAT GAGCAGATGA CGCCAAGTTG         240

ACGTCAAAGA CAGAGGCGAC AGAAACTCTG CAGCCAGCTC TTGCCCCCGA GGAGCTCAGG         300

TTCCTGCAGG AGTCATTTTA GCTTAGTCTT CTGAAGGACA CAGATACC ATG GAA GAG         357
                                                    Met Glu Glu
                                                      1

AAC ACG TTT GGG GTT CAG CAG ATC CAA CCC AAT GTA ATT TCT GTT CGT         405
Asn Thr Phe Gly Val Gln Gln Ile Gln Pro Asn Val Ile Ser Val Arg
      5                  10                  15

CTC TTC AAA CGC AAA GTG GGA GGT CTG GGC TTC CTG GTG AAG GAA CGG         453
Leu Phe Lys Arg Lys Val Gly Gly Leu Gly Phe Leu Val Lys Glu Arg
 20                  25                  30                  35

GTC AGC AAG CCT CCC GTG ATC ATC TCA GAC CTG ATT CGA GGA GGT GCT         501
Val Ser Lys Pro Pro Val Ile Ile Ser Asp Leu Ile Arg Gly Gly Ala
                 40                  45                  50

GCG GAG CAG AGC GGC CTT ATC CAA GCT GGA GAC ATC ATT CTC GCA GTC         549
Ala Glu Gln Ser Gly Leu Ile Gln Ala Gly Asp Ile Ile Leu Ala Val
             55                  60                  65

AAC GAT CGG CCC TTG GTA GAC CTC AGC TAT GAC AGT GCC CTG GAG GTT         597
Asn Asp Arg Pro Leu Val Asp Leu Ser Tyr Asp Ser Ala Leu Glu Val
         70                  75                  80

CTC AGG GGC ATT GCC TCT GAG ACC CAC GTG GTC CTC ATT CTG AGG GGC         645
Leu Arg Gly Ile Ala Ser Glu Thr His Val Val Leu Ile Leu Arg Gly
     85                  90                  95

CCT GAG GGC TTC ACT ACA CAT CTG GAG ACC ACC TTC ACA GGG GAT GGA         693
Pro Glu Gly Phe Thr Thr His Leu Glu Thr Thr Phe Thr Gly Asp Gly
100                 105                 110                 115

ACC CCC AAG ACC ATC CGG GTG ACC CAG CCC CTC GGT CCT CCC ACC AAA         741
Thr Pro Lys Thr Ile Arg Val Thr Gln Pro Leu Gly Pro Pro Thr Lys
                120                 125                 130

GCC GTC GAT CTG TCT CAC CAG CCT TCA GCC AGC AAA GAC CAG TCA TTA         789
Ala Val Asp Leu Ser His Gln Pro Ser Ala Ser Lys Asp Gln Ser Leu
            135                 140                 145

GCA GTA GAC AGA GTC ACA GGT CTG GGT AAT GGC CCT CAG CAT GCC CAA         837
Ala Val Asp Arg Val Thr Gly Leu Gly Asn Gly Pro Gln His Ala Gln
        150                 155                 160

GGC CAT GGG CAG GGA GCT GGC TCA GTC TCC CAA GCT AAT GGT GTG GCC         885
Gly His Gly Gln Gly Ala Gly Ser Val Ser Gln Ala Asn Gly Val Ala
    165                 170                 175

ATT GAC CCC ACG ATG AAA AGC ACC AAG GCC AAC CTC CAG GAC ATC GGG         933
Ile Asp Pro Thr Met Lys Ser Thr Lys Ala Asn Leu Gln Asp Ile Gly
180                 185                 190                 195

GAA CAT GAT GAA CTG CTC AAA GAG ATA GAA CCT GTG CTG AGC ATC CTC         981
Glu His Asp Glu Leu Leu Lys Glu Ile Glu Pro Val Leu Ser Ile Leu
                200                 205                 210
```

```
AAC AGT GGG AGC AAA GCC ACC AAC AGA GGG GGA CCA GCC AAA GCA GAG      1029
Asn Ser Gly Ser Lys Ala Thr Asn Arg Gly Gly Pro Ala Lys Ala Glu
            215                 220                 225

ATG AAA GAC ACA GGA ATC CAG GTG GAC AGA GAC CTC GAT GGC AAA TCG      1077
Met Lys Asp Thr Gly Ile Gln Val Asp Arg Asp Leu Asp Gly Lys Ser
            230                 235                 240

CAC AAA GCT CCG CCC CTG GGC GGG GAC AAT GAC CGC GTC TTC AAT GAC      1125
His Lys Ala Pro Pro Leu Gly Gly Asp Asn Asp Arg Val Phe Asn Asp
            245                 250                 255

CTG TGG GGG AAG GAC AAC GTT CCT GTG ATC CTT AAC AAC CCG TAT TCA      1173
Leu Trp Gly Lys Asp Asn Val Pro Val Ile Leu Asn Asn Pro Tyr Ser
260                 265                 270                 275

GAG AAG GAA CAG TCC CCT ACC TCG GGG AAA CAG TCT CCC ACC AAG AAC      1221
Glu Lys Glu Gln Ser Pro Thr Ser Gly Lys Gln Ser Pro Thr Lys Asn
                280                 285                 290

GGC AGC CCT TCC AGG TGC CCC CGT TTC CTC AAG GTC AAG AAC TGG GAG      1269
Gly Ser Pro Ser Arg Cys Pro Arg Phe Leu Lys Val Lys Asn Trp Glu
                295                 300                 305

ACG GAC GTG GTC CTC ACC GAC ACC CTG CAC CTG AAG AGC ACA CTG GAA      1317
Thr Asp Val Val Leu Thr Asp Thr Leu His Leu Lys Ser Thr Leu Glu
            310                 315                 320

ACG GGG TGC ACA GAG CAC ATT TGC ATG GGC TCG ATC ATG CTG CCT TCC      1365
Thr Gly Cys Thr Glu His Ile Cys Met Gly Ser Ile Met Leu Pro Ser
325                 330                 335

CAG CAC ACG CGG AAG CCA GAA GAT GTC CGC ACA AAG GAC CAG CTC TTC      1413
Gln His Thr Arg Lys Pro Glu Asp Val Arg Thr Lys Asp Gln Leu Phe
340                 345                 350                 355

CCT CTA GCC AAA GAA TTT CTC GAC CAA TAC TAC TCA TCC ATT AAG AGA      1461
Pro Leu Ala Lys Glu Phe Leu Asp Gln Tyr Tyr Ser Ser Ile Lys Arg
                360                 365                 370

TTT GGC TCC AAG GCC CAC ATG GAC AGG CTG GAG GAG GTG AAC AAG GAG      1509
Phe Gly Ser Lys Ala His Met Asp Arg Leu Glu Glu Val Asn Lys Glu
                375                 380                 385

ATT GAA AGC ACC AGC ACC TAC CAG CTC AAG GAC ACC GAG CTC ATC TAT      1557
Ile Glu Ser Thr Ser Thr Tyr Gln Leu Lys Asp Thr Glu Leu Ile Tyr
            390                 395                 400

GGC GCC AAG CAT GCC TGG CGG AAC GCC TCT CGA TGT GTG GGC AGG ATC      1605
Gly Ala Lys His Ala Trp Arg Asn Ala Ser Arg Cys Val Gly Arg Ile
405                 410                 415

CAG TGG TCC AAG CTG CAG GTG TTC GAT GCC CGA GAC TGC ACC ACA GCC      1653
Gln Trp Ser Lys Leu Gln Val Phe Asp Ala Arg Asp Cys Thr Thr Ala
420                 425                 430                 435

CAC GGC ATG TTC AAC TAC ATC TGT AAC CAT GTC AAG TAT GCC ACC AAC      1701
His Gly Met Phe Asn Tyr Ile Cys Asn His Val Lys Tyr Ala Thr Asn
                440                 445                 450

AAA GGG AAT CTC AGG TCG GCC ATC ACG ATA TTC CCT CAG AGG ACT GAC      1749
Lys Gly Asn Leu Arg Ser Ala Ile Thr Ile Phe Pro Gln Arg Thr Asp
                455                 460                 465

GGC AAA CAT GAC TTC CGA GTG TGG AAC TCG CAG CTC ATC CGC TAC GCG      1797
Gly Lys His Asp Phe Arg Val Trp Asn Ser Gln Leu Ile Arg Tyr Ala
                470                 475                 480

GGC TAC AAG CAG CCA GAT GGC TCT ACC TTG GGG GAT CCA GCC AAT GTG      1845
Gly Tyr Lys Gln Pro Asp Gly Ser Thr Leu Gly Asp Pro Ala Asn Val
            485                 490                 495

CAG TTC ACG GAG ATC TGT ATA CAG CAG GGC TGG AAA GCC CCA AGA GGC      1893
Gln Phe Thr Glu Ile Cys Ile Gln Gln Gly Trp Lys Ala Pro Arg Gly
500                 505                 510                 515

CGC TTC GAC GTG CTG CCT CTC CTG CTT CAG GCC AAT GGC AAT GAC CCT      1941
Arg Phe Asp Val Leu Pro Leu Leu Leu Gln Ala Asn Gly Asn Asp Pro
```

```
                    520                 525                 530
GAG CTC TTC CAG ATC CCC CCA GAG CTG GTG CTG GAA GTG CCC ATC AGG    1989
Glu Leu Phe Gln Ile Pro Pro Glu Leu Val Leu Glu Val Pro Ile Arg
            535                 540                 545

CAC CCC AAG TTC GAC TGG TTT AAG GAC CTG GGG CTC AAA TGG TAT GGC    2037
His Pro Lys Phe Asp Trp Phe Lys Asp Leu Gly Leu Lys Trp Tyr Gly
            550                 555                 560

CTC CCC GCT GTG TCC AAC ATG CTG CTG GAG ATC GGG GGC CTG GAG TTC    2085
Leu Pro Ala Val Ser Asn Met Leu Leu Glu Ile Gly Gly Leu Glu Phe
            565                 570                 575

AGC GCC TGT CCC TTC AGC GGC TGG TAC ATG GGC ACA GAG ATC GGC GTC    2133
Ser Ala Cys Pro Phe Ser Gly Trp Tyr Met Gly Thr Glu Ile Gly Val
580                 585                 590                 595

CGT GAC TAC TGT GAC AAC TCT CGA TAC AAC ATC CTG GAG GAA GTA GCC    2181
Arg Asp Tyr Cys Asp Asn Ser Arg Tyr Asn Ile Leu Glu Glu Val Ala
                600                 605                 610

AAG AAG ATG GAT TTG GAC ATG AGG AAG ACC TCG TCC CTC TGG AAG GAC    2229
Lys Lys Met Asp Leu Asp Met Arg Lys Thr Ser Ser Leu Trp Lys Asp
                615                 620                 625

CAA GCA CTG GTG GAG ATC AAC ATT GCT GTT CTA TAT AGC TTC CAG AGT    2277
Gln Ala Leu Val Glu Ile Asn Ile Ala Val Leu Tyr Ser Phe Gln Ser
            630                 635                 640

GAC AAG GTG ACC ATC GTT GAC CAC CAC TCT GCC ACG GAG TCC TTC ATC    2325
Asp Lys Val Thr Ile Val Asp His His Ser Ala Thr Glu Ser Phe Ile
            645                 650                 655

AAA CAC ATG GAG AAT GAA TAC CGC TGC AGA GGG GGC TGC CCC GCC GAC    2373
Lys His Met Glu Asn Glu Tyr Arg Cys Arg Gly Gly Cys Pro Ala Asp
660                 665                 670                 675

TGG GTG TGG ATT GTG CCT CCC ATG TCG GGC AGC ATC ACC CCT GTC TTC    2421
Trp Val Trp Ile Val Pro Pro Met Ser Gly Ser Ile Thr Pro Val Phe
                680                 685                 690

CAC CAG GAG ATG CTC AAC TAT AGA CTC ACC CCG TCC TTT GAA TAC CAG    2469
His Gln Glu Met Leu Asn Tyr Arg Leu Thr Pro Ser Phe Glu Tyr Gln
            695                 700                 705

CCT GAT CCA TGG AAC ACC CAC GTG TGG AAG GGC ACC AAC GGG ACC CCC    2517
Pro Asp Pro Trp Asn Thr His Val Trp Lys Gly Thr Asn Gly Thr Pro
            710                 715                 720

ACG AAG CGG CGA GCT ATC GGC TTT AAG AAA TTG GCA GAG GCC GTC AAG    2565
Thr Lys Arg Arg Ala Ile Gly Phe Lys Lys Leu Ala Glu Ala Val Lys
            725                 730                 735

TTC TCA GCC AAG CTA ATG GGG CAG GCC ATG GCC AAG AGG GTC AAG GCG    2613
Phe Ser Ala Lys Leu Met Gly Gln Ala Met Ala Lys Arg Val Lys Ala
740                 745                 750                 755

ACC ATT CTC TAC GCC ACA GAG ACA GGC AAA TCA CAA GCC TAT GCC AAG    2661
Thr Ile Leu Tyr Ala Thr Glu Thr Gly Lys Ser Gln Ala Tyr Ala Lys
                760                 765                 770

ACC CTG TGT GAG ATC TTC AAG CAC GCC TTC GAT GCC AAG GCA ATG TCC    2709
Thr Leu Cys Glu Ile Phe Lys His Ala Phe Asp Ala Lys Ala Met Ser
            775                 780                 785

ATG GAG GAG TAT GAC ATC GTG CAC CTG GAG CAC GAA GCC CTG GTC TTG    2757
Met Glu Glu Tyr Asp Ile Val His Leu Glu His Glu Ala Leu Val Leu
            790                 795                 800

GTG GTC ACC AGC ACC TTT GGC AAT GGA GAC CCC CCT GAG AAC GGG GAG    2805
Val Val Thr Ser Thr Phe Gly Asn Gly Asp Pro Pro Glu Asn Gly Glu
            805                 810                 815

AAA TTC GGC TGT GCT TTA ATG GAG ATG AGG CAC CCC AAC TCT GTG CAG    2853
Lys Phe Gly Cys Ala Leu Met Glu Met Arg His Pro Asn Ser Val Gln
820                 825                 830                 835

GAG GAG AGA AAG AGC TAC AAG GTC CGA TTC AAC AGC GTC TCC TCC TAT    2901
```

```
                    Glu Glu Arg Lys Ser Tyr Lys Val Arg Phe Asn Ser Val Ser Ser Tyr
                                840             845             850

TCT GAC TCC CGA AAG TCA TCG GGC GAC GGA CCC GAC CTC AGA GAC AAC                        2949
Ser Asp Ser Arg Lys Ser Ser Gly Asp Gly Pro Asp Leu Arg Asp Asn
                855             860             865

TTT GAA AGT ACT GGA CCC CTG GCC AAT GTG AGG TTC TCA GTG TTC GGC                        2997
Phe Glu Ser Thr Gly Pro Leu Ala Asn Val Arg Phe Ser Val Phe Gly
        870             875             880

CTC GGC TCT CGG GCG TAC CCC CAC TTC TGT GCC TTT GGG CAT GCG GTG                        3045
Leu Gly Ser Arg Ala Tyr Pro His Phe Cys Ala Phe Gly His Ala Val
            885             890             895

GAC ACC CTC CTG GAG GAA CTG GGA GGG GAG AGG ATT CTG AAG ATG AGG                        3093
Asp Thr Leu Leu Glu Glu Leu Gly Gly Glu Arg Ile Leu Lys Met Arg
900             905             910             915

GAG GGG GAT GAG CTT TGC GGA CAG GAA GAA GCT TTC AGG ACC TGG GCC                        3141
Glu Gly Asp Glu Leu Cys Gly Gln Glu Glu Ala Phe Arg Thr Trp Ala
                920             925             930

AAG AAA GTC TTC AAG GCA GCC TGT GAT GTG TTC TGC GTG GGG GAT GAC                        3189
Lys Lys Val Phe Lys Ala Ala Cys Asp Val Phe Cys Val Gly Asp Asp
                935             940             945

GTC AAC ATC GAG AAG CCG AAC AAC TCC CTC ATT AGC AAT GAC CGA AGC                        3237
Val Asn Ile Glu Lys Pro Asn Asn Ser Leu Ile Ser Asn Asp Arg Ser
        950             955             960

TGG AAG AGG AAC AAG TTC CGC CTC ACG TAT GTG GCG GAA GCT CCA GAT                        3285
Trp Lys Arg Asn Lys Phe Arg Leu Thr Tyr Val Ala Glu Ala Pro Asp
965             970             975

CTG ACC CAA GGT CTT TCC AAT GTT CAC AAA AAA CGA GTC TCG GCT GCT                        3333
Leu Thr Gln Gly Leu Ser Asn Val His Lys Lys Arg Val Ser Ala Ala
980             985             990             995

CGA CTC CTC AGC CGC CAA AAC CTG CAA AGC CCT AAG TTC AGC CGA TCG                        3381
Arg Leu Leu Ser Arg Gln Asn Leu Gln Ser Pro Lys Phe Ser Arg Ser
            1000            1005            1010

ACC ATC TTC GTG CGT CTC CAC ACC AAC GGG AAT CAG GAG CTG CAG TAC                        3429
Thr Ile Phe Val Arg Leu His Thr Asn Gly Asn Gln Glu Leu Gln Tyr
        1015            1020            1025

CAG CCA GGG GAC CAC CTG GGT GTC TTC CCC GGC AAC CAC GAG GAC CTC                        3477
Gln Pro Gly Asp His Leu Gly Val Phe Pro Gly Asn His Glu Asp Leu
            1030            1035            1040

GTG AAT GCA CTC ATT GAA CGG CTG GAG GAT GCA CCG CCT GCC AAC CAC                        3525
Val Asn Ala Leu Ile Glu Arg Leu Glu Asp Ala Pro Pro Ala Asn His
1045            1050            1055

GTG GTG AAG GTG GAG ATG CTG GAG GAG AGG AAC ACT GCT CTG GGT GTC                        3573
Val Val Lys Val Glu Met Leu Glu Glu Arg Asn Thr Ala Leu Gly Val
1060            1065            1070            1075

ATC AGT AAT TGG AAG GAT GAA TCT CGC CTC CCA CCC TGC ACC ATC TTC                        3621
Ile Ser Asn Trp Lys Asp Glu Ser Arg Leu Pro Pro Cys Thr Ile Phe
            1080            1085            1090

CAG GCC TTC AAG TAC TAC CTG GAC ATC ACC ACG CCG CCC ACG CCC CTG                        3669
Gln Ala Phe Lys Tyr Tyr Leu Asp Ile Thr Thr Pro Pro Thr Pro Leu
                1095            1100            1105

CAG CTG CAG CAG TTC GCC TCT CTG GCC ACT AAT GAG AAA GAG AAG CAG                        3717
Gln Leu Gln Gln Phe Ala Ser Leu Ala Thr Asn Glu Lys Glu Lys Gln
            1110            1115            1120

CGG TTG CTG GTC CTC AGC AAG GGG CTC CAG GAA TAT GAG GAG TGG AAG                        3765
Arg Leu Leu Val Leu Ser Lys Gly Leu Gln Glu Tyr Glu Glu Trp Lys
                1125            1130            1135

TGG GGC AAG AAC CCC ACA ATG GTG GAG GTG CTG GAG GAG TTC CCG TCC                        3813
Trp Gly Lys Asn Pro Thr Met Val Glu Val Leu Glu Glu Phe Pro Ser
1140            1145            1150            1155
```

```
ATC CAG ATG CCG GCT ACA CTT CTC CTC ACT CAG CTG TCG CTG CTG CAG      3861
Ile Gln Met Pro Ala Thr Leu Leu Leu Thr Gln Leu Ser Leu Leu Gln
            1160                1165                1170

CCT CGC TAC TAC TCC ATC AGC TCC TCT CCA GAC ATG TAC CCC GAC GAG      3909
Pro Arg Tyr Tyr Ser Ile Ser Ser Ser Pro Asp Met Tyr Pro Asp Glu
        1175                1180                1185

GTG CAC CTC ACT GTG GCC ATC GTC TCC TAC CAC ACC CGA GAC GGA GAA      3957
Val His Leu Thr Val Ala Ile Val Ser Tyr His Thr Arg Asp Gly Glu
    1190                1195                1200

GGA CCA GTC CAC CAC GGG GTG TGC TCC TCC TGG CTC AAC AGA ATA CAG      4005
Gly Pro Val His His Gly Val Cys Ser Ser Trp Leu Asn Arg Ile Gln
1205                1210                1215

GCT GAC GAT GTA GTC CCC TGC TTC GTG AGA GGT GCC CCT AGC TTC CAC      4053
Ala Asp Asp Val Val Pro Cys Phe Val Arg Gly Ala Pro Ser Phe His
1220                1225                1230                1235

CTG CCT CGA AAC CCC CAG GTG CCT TGC ATC CTG GTT GGC CCA GGC ACT      4101
Leu Pro Arg Asn Pro Gln Val Pro Cys Ile Leu Val Gly Pro Gly Thr
            1240                1245                1250

GGC ATC GCA CCC TTC CGA AGC TTC TGG CAA CAG CGA CAA TTT GAC ATC      4149
Gly Ile Ala Pro Phe Arg Ser Phe Trp Gln Gln Arg Gln Phe Asp Ile
        1255                1260                1265

CAA CAC AAA GGA ATG AAT CCG TGC CCC ATG GTT CTG GTC TTC GGG TGT      4197
Gln His Lys Gly Met Asn Pro Cys Pro Met Val Leu Val Phe Gly Cys
    1270                1275                1280

CGA CAA TCC AAG ATA GAT CAT ATC TAC AGA GAG GAG ACC CTG CAG GCT      4245
Arg Gln Ser Lys Ile Asp His Ile Tyr Arg Glu Glu Thr Leu Gln Ala
1285                1290                1295

AAG AAC AAG GGC GTC TTC AGA GAG CTG TAC ACT GCC TAT TCC CGG GAA      4293
Lys Asn Lys Gly Val Phe Arg Glu Leu Tyr Thr Ala Tyr Ser Arg Glu
1300                1305                1310                1315

CCG GAC AGG CCA AAG AAA TAT GTA CAG GAC GTG CTG CAG GAA CAG CTG      4341
Pro Asp Arg Pro Lys Lys Tyr Val Gln Asp Val Leu Gln Glu Gln Leu
            1320                1325                1330

GCT GAG TCT GTG TAC CGC GCC CTG AAG GAG CAA GGA GGC CAC ATT TAT      4389
Ala Glu Ser Val Tyr Arg Ala Leu Lys Glu Gln Gly Gly His Ile Tyr
        1335                1340                1345

GTC TGT GGG GAC GTT ACC ATG GCC GCC GAT GTC CTC AAA GCC ATC CAG      4437
Val Cys Gly Asp Val Thr Met Ala Ala Asp Val Leu Lys Ala Ile Gln
    1350                1355                1360

CGC ATA ATG ACC CAG CAG GGG AAA CTC TCA GAG GAG GAC GCT GGT GTA      4485
Arg Ile Met Thr Gln Gln Gly Lys Leu Ser Glu Glu Asp Ala Gly Val
1365                1370                1375

TTC ATC AGC AGG CTG AGG GAT GAC AAC CGG TAC CAC GAG GAC ATC TTT      4533
Phe Ile Ser Arg Leu Arg Asp Asp Asn Arg Tyr His Glu Asp Ile Phe
1380                1385                1390                1395

GGA GTC ACC CTC AGA ACG TAT GAA GTG ACC AAC CGC CTT AGA TCT GAG      4581
Gly Val Thr Leu Arg Thr Tyr Glu Val Thr Asn Arg Leu Arg Ser Glu
            1400                1405                1410

TCC ATC GCC TTC ATC GAA GAG AGC AAA AAA GAC GCA GAT GAG GTT TTC      4629
Ser Ile Ala Phe Ile Glu Glu Ser Lys Lys Asp Ala Asp Glu Val Phe
        1415                1420                1425

AGC TCC TAACTGGATC CTCCTGCCCC CGTGCGTGCG ATGTGGCGGC TGCCCCAAGT      4685
Ser Ser
        1430

GCCCAAGTAA GGGCGGCCGC AGGTTGACTA AATTCGGACA CACACGGCTG AACCGAGTGG   4745

CCCTGCTCTG CCTCTTGTCC TGTTGCTGTG TCCTGGTCCT TCTTCCTGCT CTGGGCTCTC   4805

TCAACCCCAC CCCTGGGTTT TCTCCTTGAC TCTTGGGCTA CGATGCATCA CCCTTGTACC   4865

CTGCAGTGGC TCTCACAAAA CCGCATCCTC CCCACCCCCA CCCGATTGCT GCCAAGGGCA   4925
```

```
GGTTGCGGTG CATGGCTGTT GCTCCTGTTG TTGGGGTCTG AAGGTGGCTG GCGCTGGGCC      4985

TCAGGTCACC CTGAACCAGT CCCTTGGCCA CTTAAGCCCC CTTCCACCCT CTTTTTATGA      5045

TGGTGTGTTT GT                                                          5057
```

(2) INFORMATION FOR SEQ ID NO:13:

(i) SEQUENCE CHARACTERISTICS:
        (A) LENGTH: 1429 amino acids
        (B) TYPE: amino acid
        (D) TOPOLOGY: linear (ii) MOLECULE TYPE: protein (xi) SEQUENCE DESCRIPTION: SEQ ID NO:13:

```
Met Glu Glu Asn Thr Phe Gly Val Gln Gln Ile Gln Pro Asn Val Ile
  1               5                  10                  15

Ser Val Arg Leu Phe Lys Arg Lys Val Gly Gly Leu Gly Phe Leu Val
                 20                  25                  30

Lys Glu Arg Val Ser Lys Pro Pro Val Ile Ile Ser Asp Leu Ile Arg
 35                  40                  45

Gly Gly Ala Ala Glu Gln Ser Gly Leu Ile Gln Ala Gly Asp Ile Ile
     50                  55                  60

Leu Ala Val Asn Asp Arg Pro Leu Val Asp Leu Ser Tyr Asp Ser Ala
 65                  70                  75                  80

Leu Glu Val Leu Arg Gly Ile Ala Ser Glu Thr His Val Val Leu Ile
                 85                  90                  95

Leu Arg Gly Pro Glu Gly Phe Thr Thr His Leu Glu Thr Thr Phe Thr
                100                 105                 110

Gly Asp Gly Thr Pro Lys Thr Ile Arg Val Thr Gln Pro Leu Gly Pro
            115                 120                 125

Pro Thr Lys Ala Val Asp Leu Ser His Gln Pro Ser Ala Ser Lys Asp
130                 135                 140

Gln Ser Leu Ala Val Asp Arg Val Thr Gly Leu Gly Asn Gly Pro Gln
145                 150                 155                 160

His Ala Gln Gly His Gly Gln Gly Ala Gly Ser Val Ser Gln Ala Asn
                165                 170                 175

Gly Val Ala Ile Asp Pro Thr Met Lys Ser Thr Lys Ala Asn Leu Gln
            180                 185                 190

Asp Ile Gly Glu His Asp Glu Leu Leu Lys Glu Ile Glu Pro Val Leu
        195                 200                 205

Ser Ile Leu Asn Ser Gly Ser Lys Ala Thr Asn Arg Gly Gly Pro Ala
    210                 215                 220

Lys Ala Glu Met Lys Asp Thr Gly Ile Gln Val Asp Arg Asp Leu Asp
225                 230                 235                 240

Gly Lys Ser His Lys Ala Pro Pro Leu Gly Asp Asn Asp Arg Val
                245                 250                 255

Phe Asn Asp Leu Trp Gly Lys Asn Val Pro Val Ile Leu Asn Asn
            260                 265                 270

Pro Tyr Ser Glu Lys Glu Gln Ser Pro Thr Ser Gly Lys Gln Ser Pro
        275                 280                 285

Thr Lys Asn Gly Ser Pro Ser Arg Cys Pro Arg Phe Leu Lys Val Lys
    290                 295                 300

Asn Trp Glu Thr Asp Val Val Leu Thr Asp Thr Leu His Leu Lys Ser
305                 310                 315                 320
```

```
Thr Leu Glu Thr Gly Cys Thr Glu His Ile Cys Met Gly Ser Ile Met
                325                 330                 335

Leu Pro Ser Gln His Thr Arg Lys Pro Glu Asp Val Arg Thr Lys Asp
            340                 345                 350

Gln Leu Phe Pro Leu Ala Lys Glu Phe Leu Asp Gln Tyr Tyr Ser Ser
        355                 360                 365

Ile Lys Arg Phe Gly Ser Lys Ala His Met Asp Arg Leu Glu Glu Val
    370                 375                 380

Asn Lys Glu Ile Glu Ser Thr Ser Thr Tyr Gln Leu Lys Asp Thr Glu
385                 390                 395                 400

Leu Ile Tyr Gly Ala Lys His Ala Trp Arg Asn Ala Ser Arg Cys Val
            405                 410                 415

Gly Arg Ile Gln Trp Ser Lys Leu Gln Val Phe Asp Ala Arg Asp Cys
        420                 425                 430

Thr Thr Ala His Gly Met Phe Asn Tyr Ile Cys Asn His Val Lys Tyr
    435                 440                 445

Ala Thr Asn Lys Gly Asn Leu Arg Ser Ala Ile Thr Ile Phe Pro Gln
450                 455                 460

Arg Thr Asp Gly Lys His Asp Phe Arg Val Trp Asn Ser Gln Leu Ile
465                 470                 475                 480

Arg Tyr Ala Gly Tyr Lys Gln Pro Asp Gly Ser Thr Leu Gly Asp Pro
            485                 490                 495

Ala Asn Val Gln Phe Thr Glu Ile Cys Ile Gln Gln Gly Trp Lys Ala
        500                 505                 510

Pro Arg Gly Arg Phe Asp Val Leu Pro Leu Leu Leu Gln Ala Asn Gly
    515                 520                 525

Asn Asp Pro Glu Leu Phe Gln Ile Pro Pro Glu Leu Val Leu Glu Val
530                 535                 540

Pro Ile Arg His Pro Lys Phe Asp Trp Phe Lys Asp Leu Gly Leu Lys
545                 550                 555                 560

Trp Tyr Gly Leu Pro Ala Val Ser Asn Met Leu Leu Glu Ile Gly Gly
            565                 570                 575

Leu Glu Phe Ser Ala Cys Pro Phe Ser Gly Trp Tyr Met Gly Thr Glu
        580                 585                 590

Ile Gly Val Arg Asp Tyr Cys Asp Asn Ser Arg Tyr Asn Ile Leu Glu
    595                 600                 605

Glu Val Ala Lys Lys Met Asp Leu Asp Met Arg Lys Thr Ser Ser Leu
610                 615                 620

Trp Lys Asp Gln Ala Leu Val Glu Ile Asn Ile Ala Val Leu Tyr Ser
625                 630                 635                 640

Phe Gln Ser Asp Lys Val Thr Ile Val Asp His His Ser Ala Thr Glu
            645                 650                 655

Ser Phe Ile Lys His Met Glu Asn Glu Tyr Arg Cys Arg Gly Gly Cys
        660                 665                 670

Pro Ala Asp Trp Val Trp Ile Val Pro Pro Met Ser Gly Ser Ile Thr
    675                 680                 685

Pro Val Phe His Gln Glu Met Leu Asn Tyr Arg Leu Thr Pro Ser Phe
690                 695                 700

Glu Tyr Gln Pro Asp Pro Trp Asn Thr His Val Trp Lys Gly Thr Asn
705                 710                 715                 720

Gly Thr Pro Thr Lys Arg Arg Ala Ile Gly Phe Lys Lys Leu Ala Glu
            725                 730                 735

Ala Val Lys Phe Ser Ala Lys Leu Met Gly Gln Ala Met Ala Lys Arg
```

-continued

```
                    740                 745                 750
Val Lys Ala Thr Ile Leu Tyr Ala Thr Glu Thr Gly Lys Ser Gln Ala
            755                 760                 765
Tyr Ala Lys Thr Leu Cys Glu Ile Phe Lys His Ala Phe Asp Ala Lys
770                 775                 780
Ala Met Ser Met Glu Glu Tyr Asp Ile Val His Leu Glu His Glu Ala
785                 790                 795                 800
Leu Val Leu Val Val Thr Ser Thr Phe Gly Asn Gly Asp Pro Pro Glu
                805                 810                 815
Asn Gly Glu Lys Phe Gly Cys Ala Leu Met Glu Met Arg His Pro Asn
            820                 825                 830
Ser Val Gln Glu Glu Arg Lys Ser Tyr Lys Val Arg Phe Asn Ser Val
            835                 840                 845
Ser Ser Tyr Ser Asp Ser Arg Lys Ser Ser Gly Asp Gly Pro Asp Leu
850                 855                 860
Arg Asp Asn Phe Glu Ser Thr Gly Pro Leu Ala Asn Val Arg Phe Ser
865                 870                 875                 880
Val Phe Gly Leu Gly Ser Arg Ala Tyr Pro His Phe Cys Ala Phe Gly
                885                 890                 895
His Ala Val Asp Thr Leu Leu Glu Glu Leu Gly Gly Glu Arg Ile Leu
            900                 905                 910
Lys Met Arg Glu Gly Asp Glu Leu Cys Gly Gln Glu Glu Ala Phe Arg
            915                 920                 925
Thr Trp Ala Lys Lys Val Phe Lys Ala Ala Cys Asp Val Phe Cys Val
        930                 935                 940
Gly Asp Asp Val Asn Ile Glu Lys Pro Asn Asn Ser Leu Ile Ser Asn
945                 950                 955                 960
Asp Arg Ser Trp Lys Arg Asn Lys Phe Arg Leu Thr Tyr Val Ala Glu
                965                 970                 975
Ala Pro Asp Leu Thr Gln Gly Leu Ser Asn Val His Lys Lys Arg Val
            980                 985                 990
Ser Ala Ala Arg Leu Leu Ser Arg Gln Asn Leu Gln Ser Pro Lys Phe
            995                 1000                1005
Ser Arg Ser Thr Ile Phe Val Arg Leu His Thr Asn Gly Asn Gln Glu
        1010                1015                1020
Leu Gln Tyr Gln Pro Gly Asp His Leu Gly Val Phe Pro Gly Asn His
1025                1030                1035                1040
Glu Asp Leu Val Asn Ala Leu Ile Glu Arg Leu Glu Asp Ala Pro Pro
                1045                1050                1055
Ala Asn His Val Val Lys Val Glu Met Leu Glu Glu Arg Asn Thr Ala
            1060                1065                1070
Leu Gly Val Ile Ser Asn Trp Lys Asp Glu Ser Arg Leu Pro Pro Cys
        1075                1080                1085
Thr Ile Phe Gln Ala Phe Lys Tyr Tyr Leu Asp Ile Thr Thr Pro Pro
        1090                1095                1100
Thr Pro Leu Gln Leu Gln Gln Phe Ala Ser Leu Ala Thr Asn Glu Lys
1105                1110                1115                1120
Glu Lys Gln Arg Leu Leu Val Leu Ser Lys Gly Leu Gln Glu Tyr Glu
                1125                1130                1135
Glu Trp Lys Trp Gly Lys Asn Pro Thr Met Val Glu Val Leu Glu Glu
            1140                1145                1150
Phe Pro Ser Ile Gln Met Pro Ala Thr Leu Leu Leu Thr Gln Leu Ser
        1155                1160                1165
```

-continued

```
Leu Leu Gln Pro Arg Tyr Tyr Ser Ile Ser Ser Pro Asp Met Tyr
    1170                1175                1180
Pro Asp Glu Val His Leu Thr Val Ala Ile Val Ser Tyr His Thr Arg
1185                1190                1195                1200
Asp Gly Glu Gly Pro Val His His Gly Val Cys Ser Ser Trp Leu Asn
            1205                1210                1215
Arg Ile Gln Ala Asp Asp Val Val Pro Cys Phe Val Arg Gly Ala Pro
            1220                1225                1230
Ser Phe His Leu Pro Arg Asn Pro Gln Val Pro Cys Ile Leu Val Gly
            1235                1240                1245
Pro Gly Thr Gly Ile Ala Pro Phe Arg Ser Phe Trp Gln Gln Arg Gln
            1250                1255                1260
Phe Asp Ile Gln His Lys Gly Met Asn Pro Cys Pro Met Val Leu Val
1265                1270                1275                1280
Phe Gly Cys Arg Gln Ser Lys Ile Asp His Ile Tyr Arg Glu Glu Thr
                1285                1290                1295
Leu Gln Ala Lys Asn Lys Gly Val Phe Arg Glu Leu Tyr Thr Ala Tyr
                1300                1305                1310
Ser Arg Glu Pro Asp Arg Pro Lys Lys Tyr Val Gln Asp Val Leu Gln
            1315                1320                1325
Glu Gln Leu Ala Glu Ser Val Tyr Arg Ala Leu Lys Glu Gln Gly Gly
            1330                1335                1340
His Ile Tyr Val Cys Gly Asp Val Thr Met Ala Ala Asp Val Leu Lys
1345                1350                1355                1360
Ala Ile Gln Arg Ile Met Thr Gln Gln Gly Lys Leu Ser Glu Glu Asp
                1365                1370                1375
Ala Gly Val Phe Ile Ser Arg Leu Arg Asp Asp Asn Arg Tyr His Glu
            1380                1385                1390
Asp Ile Phe Gly Val Thr Leu Arg Thr Tyr Glu Val Thr Asn Arg Leu
            1395                1400                1405
Arg Ser Glu Ser Ile Ala Phe Ile Glu Glu Ser Lys Lys Asp Ala Asp
        1410                1415                1420
Glu Val Phe Ser Ser
1425

(2) INFORMATION FOR SEQ ID NO:14:

(i) SEQUENCE CHARACTERISTICS:
        (A) LENGTH: 5086 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: human bcl-2 cDNA (ix) FEATURE:
        (A) NAME/KEY: CDS
        (B) LOCATION: 1459..2178

(xi) SEQUENCE DESCRIPTION: SEQ ID NO:14:

GCGCCCGCCC CTCCGCGCCG CCTGCCCGCC CGCCCGCCGC GCTCCCGCCC GCCGCTCTCC      60

GTGGCCCCGC CGCGCTGCCG CCGCCGCCGC TGCCAGCGAA GGTGCCGGGG CTCCGGGCCC     120
```

-continued

```
TCCCTGCCGG CGGCCGTCAG CGCTCGGAGC GAACTGCGCG ACGGGAGGTC CGGGAGGCGA    180

CCGTAGTCGC GCCGCCGCGC AGGACCAGGA GGAGGAGAAA GGGTGCGCAG CCCGGAGGCG    240

GGGTGCGCCG GTGGGGTGCA GCGGAAGAGG GGGTCCAGGG GGGAGAACTT CGTAGCAGTC    300

ATCCTTTTTA GGAAAAGAGG GAAAAAATAA AACCCTCCCC CACCACCTCC TTCTCCCCAC    360

CCCTCGCCGC ACCACACACA GCGCGGGCTT CTAGCGCTCG GCACCGGCGG GCCAGGCGCG    420

TCCTGCCTTC ATTTATCCAG CAGCTTTTCG GAAAATGCAT TTGCTGTTCG GAGTTTAATC    480

AGAAGACGAT TCCTGCCTCC GTCCCCGGCT CCTTCATCGT CCCATCTCCC CTGTCTCTCT    540

CCTGGGGAGG CGTGAAGCGG TCCCGTGGAT AGAGATTCAT GCCTGTGTCC GCGCGTGTGT    600

GCGCGCGTAT AAATTGCCGA GAAGGGGAAA ACATCACAGG ACTTCTGCGA ATACCGGACT    660

GAAAATTGTA ATTCATCTGC CGCCGCCGCT GCCAAAAAAA AACTCGAGCT CTTGAGATCT    720

CCGGTTGGGA TTCCTGCGGA TTGACATTTC TGTGAAGCAG AAGTCTGGGA ATCGATCTGG    780

AAATCCTCCT AATTTTTACT CCCTCTCCCC CCGACTCCTG ATTCATTGGG AAGTTTCAAA    840

TCAGCTATAA CTGGAGAGTG CTGAAGATTG ATGGGATCGT TGCCTTATGC ATTTGTTTTG    900

GTTTTACAAA AAGGAAACTT GACAGAGGAT CATGCTGTAC TTAAAAAATA CAAGTAAGTC    960

TCGCACAGGA AATTGGTTTA ATGTAACTTT CAATGGAAAC CTTTGAGATT TTTTACTTAA   1020

AGTGCATTCG AGTAAATTTA ATTTCCAGGC AGCTTAATAC ATTGTTTTTA GCCGTGTTAC   1080

TTGTAGTGTG TATGCCCTGC TTTCACTCAG TGTGTACAGG GAAACGCACC TGATTTTTTA   1140

CTTATTAGTT TGTTTTTTCT TTAACCTTTC AGCATCACAG AGGAAGTAGA CTGATATTAA   1200

CAATACTTAC TAATAATAAC GTGCCTCATG AAATAAAGAT CCGAAAGGAA TTGGAATAAA   1260

AATTTCCTGC GTCTCATGCC AAGAGGGAAA CACCAGAATC AAGTGTTCCG CGTGATTGAA   1320

GACACCCCCT CGTCCAAGAA TGCAAAGCAC ATCCAATAAA ATAGCTGGAT TATAACTCCT   1380

CTTCTTTCTC TGGGGGCCGT GGGGTGGGAG CTGGGGCGAG AGGTGCCGTT GGCCCCCGTT   1440

GCTTTTCCTC TGGGAAGG ATG GCG CAC GCT GGG AGA ACG GGG TAC GAC AAC     1491
                    Met Ala His Ala Gly Arg Thr Gly Tyr Asp Asn
                      1               5                  10

CGG GAG ATA GTG ATG AAG TAC ATC CAT TAT AAG CTG TCG CAG AGG GGC     1539
Arg Glu Ile Val Met Lys Tyr Ile His Tyr Lys Leu Ser Gln Arg Gly
             15                  20                  25

TAC GAG TGG GAT GCG GGA GAT GTG GGC GCC GCG CCC CCG GGG GCC GCC     1587
Tyr Glu Trp Asp Ala Gly Asp Val Gly Ala Ala Pro Pro Gly Ala Ala
         30                  35                  40

CCC GCA CCG GGC ATC TTC TCC TCC CAG CCC GGG CAC ACG CCC CAT CCA     1635
Pro Ala Pro Gly Ile Phe Ser Ser Gln Pro Gly His Thr Pro His Pro
     45                  50                  55

GCC GCA TCC CGC GAC CCG GTC GCC AGG ACC TCG CCG CTG CAG ACC CCG     1683
Ala Ala Ser Arg Asp Pro Val Ala Arg Thr Ser Pro Leu Gln Thr Pro
 60                  65                  70                  75

GCT GCC CCC GGC GCC GCC GCG GGG CCT GCG CTC AGC CCG GTG CCA CCT     1731
Ala Ala Pro Gly Ala Ala Ala Gly Pro Ala Leu Ser Pro Val Pro Pro
                 80                  85                  90

GTG GTC CAC CTG GCC CTC CGC CAA GCC GGC GAC GAC TTC TCC CGC CGC     1779
Val Val His Leu Ala Leu Arg Gln Ala Gly Asp Asp Phe Ser Arg Arg
             95                 100                 105

TAC CGC GGC GAC TTC GCC GAG ATG TCC AGC CAG CTG CAC CTG ACG CCC     1827
Tyr Arg Gly Asp Phe Ala Glu Met Ser Ser Gln Leu His Leu Thr Pro
        110                 115                 120

TTC ACC GCG CGG GGA CGC TTT GCC ACG GTG GTG GAG GAG CTC TTC AGG     1875
Phe Thr Ala Arg Gly Arg Phe Ala Thr Val Val Glu Glu Leu Phe Arg
```

```
            125                 130                 135
GAC GGG GTG AAC TGG GGG AGG ATT GTG GCC TTC TTT GAG TTC GGT GGG    1923
Asp Gly Val Asn Trp Gly Arg Ile Val Ala Phe Phe Glu Phe Gly Gly
140                 145                 150                 155

GTC ATG TGT GTG GAG AGC GTC AAC CGG GAG ATG TCG CCC CTG GTG GAC    1971
Val Met Cys Val Glu Ser Val Asn Arg Glu Met Ser Pro Leu Val Asp
                160                 165                 170

AAC ATC GCC CTG TGG ATG ACT GAG TAC CTG AAC CGG CAC CTG CAC ACC    2019
Asn Ile Ala Leu Trp Met Thr Glu Tyr Leu Asn Arg His Leu His Thr
            175                 180                 185

TGG ATC CAG GAT AAC GGA GGC TGG GAT GCC TTT GTG GAA CTG TAC GGC    2067
Trp Ile Gln Asp Asn Gly Gly Trp Asp Ala Phe Val Glu Leu Tyr Gly
            190                 195                 200

CCC AGC ATG CGG CCT CTG TTT GAT TTC TCC TGG CTG TCT CTG AAG ACT    2115
Pro Ser Met Arg Pro Leu Phe Asp Phe Ser Trp Leu Ser Leu Lys Thr
    205                 210                 215

CTG CTC AGT TTG GCC CTG GTG GGA GCT TGC ATC ACC CTG GGT GCC TAT    2163
Leu Leu Ser Leu Ala Leu Val Gly Ala Cys Ile Thr Leu Gly Ala Tyr
220                 225                 230                 235

CTG AGC CAC AAG TGAAGTCAAC ATGCCTGCCC CAAACAAATA TGCAAAAGGT        2215
Leu Ser His Lys
                240

TCACTAAAGC AGTAGAAATA ATATGCATTG TCAGTGATGT ACCATGAAAC AAAGCTGCAG  2275

GCTGTTTAAG AAAAAATAAC ACACATATAA ACATCACACA CACAGACAGA CACACACACA  2335

CACAACAATT AACAGTCTTC AGGCAAAACG TCGAATCAGC TATTTACTGC CAAAGGGAAA  2395

TATCATTTAT TTTTTACATT ATTAAGAAAA AAGATTTATT TATTTAAGAC AGTCCCATCA  2455

AAACTCCGTC TTTGGAAATC CGACCACTAA TTGCCAAACA CCGCTTCGTG TGGCTCCACC  2515

TGGATGTTCT GTGCCTGTAA ACATAGATTC GCTTTCCATG TTGTTGGCCG GATCACCATC  2575

TGAAGAGCAG ACGGATGGAA AAAGGACCTG ATCATTGGGG AAGCTGGCTT TCTGGCTGCT  2635

GGAGGCTGGG GAGAAGGTGT TCATTCACTT GCATTTCTTT GCCCTGGGGG CGTGATATTA  2695

ACAGAGGGAG GGTTCCCGTG GGGGGAAGTC CATGCCTCCC TGGCCTGAAG AAGAGACTCT  2755

TTGCATATGA CTCACATGAT GCATACCTGG TGGGAGGAAA AGAGTTGGGA ACTTCAGATG  2815

GACCTAGTAC CCACTGAGAT TTCCACGCCG AAGGACAGCG ATGGGAAAAA TGCCCTTAAA  2875

TCATAGGAAA GTATTTTTTT AAGCTACCAA TTGTGCCGAG AAAAGCATTT TAGCAATTTA  2935

TACAATATCA TCCAGTACCT TAAACCCTGA TTGTGTATAT TCATATATTT TGGATACGCA  2995

CCCCCCAACT CCCAATACTG GCTCTGTCTG AGTAAGAAAC AGAATCCTCT GGAACTTGAG  3055

GAAGTGAACA TTTCGGTGAC TTCCGATCAG GAAGGCTAGA GTTACCCAGA GCATCAGGCC  3115

GCCACAAGTG CCTGCTTTTA GGAGACCGAA GTCCGCAGAA CCTACCTGTG TCCCAGCTTG  3175

GAGGCCTGGT CCTGGAACTG AGCCGGGCCC TCACTGGCCT CCTCCAGGGA TGATCAACAG  3235

GGTAGTGTGG TCTCCGAATG TCTGGAAGCT GATGGATGGA GCTCAGAATT CCACTGTCAA  3295

GAAAGAGCAG TAGAGGGGTG TGGCTGGGCC TGTCACCCTG GGGCCCTCCA GGTAGGCCCG  3355

TTTTCACGTG GAGCATAGGA GCCACGACCC TTCTTAAGAC ATGTATCACT GTAGAGGGAA  3415

GGAACAGAGG CCCTGGGCCT TCCTATCAGA AGGACATGGT GAAGGCTGGG AACGTGAGGA  3475

GAGGCAATGG CCACGGCCCA TTTTGGCTGT AGCACATGGC ACGTTGGCTG TGTGGCCTTG  3535

GCCACCTGTG AGTTTAAAGC AAGGCTTTAA ATGACTTTGG AGAGGGTCAC AAATCCTAAA  3595

AGAAGCATTG AAGTGAGGTG TCATGGATTA ATTGACCCCT GTCTATGGAA TTACATGTAA  3655

AACATTATCT TGTCACTGTA GTTTGGTTTT ATTTGAAAAC CTGACAAAAA AAAGTTCCA   3715
```

```
GGTGTGGAAT ATGGGGGTTA TCTGTACATC CTGGGGCATT AAAAAAAAAT CAATGGTGGG      3775

GAACTATAAA GAAGTAACAA AAGAAGTGAC ATCTTCAGCA AATAAACTAG GAAATTTTTT      3835

TTTCTTCCAG TTTAGAATCA GCCTTGAAAC ATTGATGGAA TAACTCTGTG GCATTATTGC      3895

ATTATATACC ATTTATCTGT ATTAACTTTG GAATGTACTC TGTTCAATGT TTAATGCTGT      3955

GGTTGATATT TCGAAAGCTG CTTTAAAAAA ATACATGCAT CTCAGCGTTT TTTTGTTTTT      4015

AATTGTATTT AGTTATGGCC TATACACTAT TTGTGAGCAA AGGTGATCGT TTTCTGTTTG      4075

AGATTTTTAT CTCTTGATTC TTCAAAAGCA TTCTGAGAAG GTGAGATAAG CCCTGAGTCT      4135

CAGCTACCTA AGAAAAACCT GGATGTCACT GGCCACTGAG GAGCTTTGTT TCAACCAAGT      4195

CATGTGCATT TCCACGTCAA CAGAATTGTT TATTGTGACA GTTATATCTG TTGTCCCTTT      4255

GACCTTGTTT CTTGAAGGTT TCCTCGTCCC TGGGCAATTC CGCATTTAAT TCATGGTATT      4315

CAGGATTACA TGCATGTTTG GTTAAACCCA TGAGATTCAT TCAGTTAAAA ATCCAGATGG      4375

CGAATGACCA GCAGATTCAA ATCTATGGTG GTTTGACCTT TAGAGAGTTG CTTTACGTGG      4435

CCTGTTTCAA CACAGACCCA CCCAGAGCCC TCCTGCCCTC CTTCCGCGGG GGCTTTCTCA      4495

TGGCTGTCCT TCAGGGTCTT CCTGAAATGC AGTGGTCGTT ACGCTCCACC AAGAAAGCAG      4555

GAAACCTGTG GTATGAAGCC AGACCTCCCC GGCGGGCCTC AGGGAACAGA ATGATCAGAC      4615

CTTTGAATGA TTCTAATTTT TAAGCAAAAT ATTATTTTAT GAAAGGTTTA CATTGTCAAA      4675

GTGATGAATA TGGAATATCC AATCCTGTGC TGCTATCCTG CCAAAATCAT TTTAATGGAG      4735

TCAGTTTGCA GTATGCTCCA CGTGGTAAGA TCCTCCAAGC TGCTTTAGAA GTAACAATGA      4795

AGAACGTGGA CGTTTTTAAT ATAAAGCCTG TTTTGTCTTT TGTTGTTGTT CAAACGGGAT      4855

TCACAGAGTA TTTGAAAAAT GTATATATAT TAAGAGGTCA CGGGGGCTAA TTGCTAGCTG      4915

GCTGCCTTTT GCTGTGGGGT TTTGTTACCT GGTTTTAATA ACAGTAAATG TGCCCAGCCT      4975

CTTGGCCCCA GAACTGTACA GTATTGTGGC TGCACTTGCT CTAAGAGTAG TTGATGTTGC      5035

ATTTTCCTTA TTGTTAAAAA CATGTTAGAA GCAATGAATG TATATAAAAG C             5086
```

(2) INFORMATION FOR SEQ ID NO:15:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:15:

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
                100                 105                 110
```

```
Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235
```

(2) INFORMATION FOR SEQ ID NO:16:

(i) SEQUENCE CHARACTERISTICS:
        (A) LENGTH: 1846 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: bcl-2 fusion gene; Seto, et al.,
            EMBO J 7:123 (1988)

(ix) FEATURE:
        (A) NAME/KEY: CDS
        (B) LOCATION: 887..1606

(xi) SEQUENCE DESCRIPTION: SEQ ID NO:16:

```
ACCACCTCCT TCTCCCCACC CCTCGCCGCA CCACACACAG CGCGGGCTTC TGGCGCTCGG        60

CACCGGCGGG CCAGGCGCGT CCTGTCTTCA TTTATCCAGC AGCTTTTCGG AAAATCCATT       120

TGGTGTTCGG AGTTTAATCA GAAGAGGATT CCTGCCTCCG TCCCCGGCTC CTTCATCGTC       180

CCCTCTCCCC TGTCTCTCTC CTGGGGAGGC GTGAAGAGAG ATTCATGCCT GTGCCCGCGC       240

GTGTGTGCGC GCGTATAAAT TGCCGAGAAG GGGAAAACAT CACAGGACTT CTGCGAATAC       300

CGGACTGAAA ATTGTAGCTC ATCTGCCGCC GCCGCTGCCT TTTTTTTTTC TCGAGCTCTT       360

GAGATCTCCG GTTGGGACTC CTGCGGATTG ACATTTCTGT GAAGCAGAAG TCTGGGAATC       420

GATCTGGAAA TCCTCCTAAT TTTTACTCCC TCTCCCCCCG ACTCCTGATT CATTGGGAAG       480

TTTCAAATCA GCTATAACTG AGAGAGCTG AAGATTGATG GATCGTTGC CTTATGCCTT        540

TGTTTTGGTT TTACAAAAAG GAAACTTGAC AGAGGATCAT GCTATACTTA AAAATACAA        600

CATCGCAGAG GAAGTAGACT CATATTAAAA ATACTTACTA ATAATAACGT GCCTCATGAA       660

GTAAAGATCC GAAAGGAATT GGAATAAAAC TTTCCTGCAT CTCAAGCCAA GGGGAAACA        720

CCAGAATCAA GTGTTCCGCG TGATTGAAGA CACCCCCTCG TCCAAGAATG CAAAGCACAT       780

CCAATAAAAG AGCTGGATTA TAACTCCTCT TCTTTCTCTG GGGCCGTGG GGTAGGGCT        840

GGGGCGAGAG GTGCCGTTGG CCCCCGTTGC TTTTCCTCTG GGAGGG ATG GCG CAC         895
```

```
                                    Met Ala His
                                      1
GCT GGG AGA AGT GGT TAC GAT AAC CGG GAG ATA GTG ATG AAG TAC ATC       943
Ala Gly Arg Ser Gly Tyr Asp Asn Arg Glu Ile Val Met Lys Tyr Ile
         5                  10                  15

CAT TAT AAG CTG TCG CAG AGG GGC TAC GAG TGG GAT GCG GGA GAT GTG       991
His Tyr Lys Leu Ser Gln Arg Gly Tyr Glu Trp Asp Ala Gly Asp Val
 20                  25                  30                  35

GGC GCC GCG CCC CCG GGG GCC GCC CCC GCA CCG GGC TTC TTC TCC TCC      1039
Gly Ala Ala Pro Pro Gly Ala Ala Pro Ala Pro Gly Phe Phe Ser Ser
                 40                  45                  50

CAG CCC GGG CAC ACG CCC CAT CCA GCC GCA TCC CGG GAC CCG GTC GCC      1087
Gln Pro Gly His Thr Pro His Pro Ala Ala Ser Arg Asp Pro Val Ala
                 55                  60                  65

AGG ACC TCG CCA CTA CAG ACC CCG GCT GCC CCC GGC GCC GCC GCG GGG      1135
Arg Thr Ser Pro Leu Gln Thr Pro Ala Ala Pro Gly Ala Ala Ala Gly
         70                  75                  80

CCT GCG CTC AGC CCG GTG CCA CCT GTG GTC CAC CTG ACC CTC CGC CAG      1183
Pro Ala Leu Ser Pro Val Pro Pro Val Val His Leu Thr Leu Arg Gln
 85                  90                  95

GCC GGC GAC GAC TTC TCC CGC CGC TAC CGC CGC GAC TTC GCC GAG ATG      1231
Ala Gly Asp Asp Phe Ser Arg Arg Tyr Arg Arg Asp Phe Ala Glu Met
100                 105                 110                 115

TCC AGC CAG CTG CAC CTG ACG CCC TTC ACC GCG CGG GGA TGC TTT GCC      1279
Ser Ser Gln Leu His Leu Thr Pro Phe Thr Ala Arg Gly Cys Phe Ala
                 120                 125                 130

ACG GTG GTG GAG GAG CTC TTC AGG GAC GGG GTG AAC TGG GGG AGG ATT      1327
Thr Val Val Glu Glu Leu Phe Arg Asp Gly Val Asn Trp Gly Arg Ile
                 135                 140                 145

GTG GCC TTC TTT GAG TTC GGT GGG GTC ATG TGT GTG GAG AGC GTC AAC      1375
Val Ala Phe Phe Glu Phe Gly Gly Val Met Cys Val Glu Ser Val Asn
                 150                 155                 160

CGG GAG ATG TCG CCC CTG GTG GAC AAC ATC GCC CTG TGG ATG ACT GAG      1423
Arg Glu Met Ser Pro Leu Val Asp Asn Ile Ala Leu Trp Met Thr Glu
165                 170                 175

TAC CTG AAC CGG CAC CTG CAC ACC TGG ATC CAG GAT AAC GGA GGC TGG      1471
Tyr Leu Asn Arg His Leu His Thr Trp Ile Gln Asp Asn Gly Gly Trp
180                 185                 190                 195

GAT GCC TTT GTG GAA CTG TAC GGC CCC AGC ATG CGG CCT CTG TTT GAT      1519
Asp Ala Phe Val Glu Leu Tyr Gly Pro Ser Met Arg Pro Leu Phe Asp
                 200                 205                 210

TTC TCC TGG CTG TCT CTG AAG ACT CTG CTC AGT TTG GCC CTG GTG GGA      1567
Phe Ser Trp Leu Ser Leu Lys Thr Leu Leu Ser Leu Ala Leu Val Gly
                 215                 220                 225

GCT TGC ATC ACC CTG GGT GCC TAT CTG GGC CAC AAG TGAAGTCAAC           1613
Ala Cys Ile Thr Leu Gly Ala Tyr Leu Gly His Lys
                 230                 235         240

ATGCCTGCCC CAAACAAATA TGCAAAAGGT TCACTAAAGC AGTAGAAATA ATATGCATTG    1673

TCAGTGATGT ACCATGAAAC AAAGCTGCAG GCTGTTTAAG AAAAAATAAC ACACATATAA    1733

ACATCACACA CACAGACAGA CACACACACA CACAACAATT AACAGTCTTC AGGCAAAACG    1793

TCGAATCAGC TATTTACTGC CAAAGGGAAA TATCATTTAT TTTTTACATT ATT           1846
```

(2) INFORMATION FOR SEQ ID NO:17:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:17:

Met Ala His Ala Gly Arg Ser Gly Tyr Asp Asn Arg Glu Ile Val Met
 1               5                  10                  15

Lys Tyr Ile His Tyr Lys Leu Ser Gln Arg Gly Tyr Glu Trp Asp Ala
                 20                  25                  30

Gly Asp Val Gly Ala Ala Pro Pro Gly Ala Ala Pro Ala Pro Gly Phe
             35                  40                  45

Phe Ser Ser Gln Pro Gly His Thr Pro His Pro Ala Ala Ser Arg Asp
         50                  55                  60

Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
                 85                  90                  95

Leu Arg Gln Ala Gly Asp Asp Phe Ser Arg Arg Tyr Arg Arg Asp Phe
                100                 105                 110

Ala Glu Met Ser Ser Gln Leu His Leu Thr Pro Phe Thr Ala Arg Gly
            115                 120                 125

Cys Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

(2) INFORMATION FOR SEQ ID NO:18:

(i) SEQUENCE CHARACTERISTICS:
        (A) LENGTH: 4353 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Human NOS-1 gene, Fujisawa, et al,
            J. Neurochem 63:140 1994

(ix) FEATURE:
        (A) NAME/KEY: CDS
        (B) LOCATION: 1..4305

(xi) SEQUENCE DESCRIPTION: SEQ ID NO:18:

ATG GAG GAT CAC ATG TTC GGT GTT CAG CAA ATC CAG CCC AAT GTC ATT      48
Met Glu Asp His Met Phe Gly Val Gln Gln Ile Gln Pro Asn Val Ile
 1               5                  10                  15

TCT GTT CGT CTC TTC AAG CGC AAA GTT GGG GGC TGG GGA TTT CTG GTG      96

```
Ser Val Arg Leu Phe Lys Arg Lys Val Gly Gly Leu Gly Phe Leu Val
         20                  25                  30

AAG GAG CGG GTC AGT AAG CCG CCC GTG ATC ATC TCT GAC CTG ATT CGT      144
Lys Glu Arg Val Ser Lys Pro Pro Val Ile Ile Ser Asp Leu Ile Arg
             35                  40                  45

GGG GGC GCC GCA GAG CAG AGT GGC CTC ATC CAG GCC GGA GAC ATC ATT      192
Gly Gly Ala Ala Glu Gln Ser Gly Leu Ile Gln Ala Gly Asp Ile Ile
     50                  55                  60

CTT GCG GTC AAC GGC CGG CCC TTG GTG GAC CTG AGC TAT GAC AGC GCC      240
Leu Ala Val Asn Gly Arg Pro Leu Val Asp Leu Ser Tyr Asp Ser Ala
 65                  70                  75                  80

CTG GAG GTA CTC AGA GGC ATT GCC TCT GAG ACC CAC GTG GTC CTC ATT      288
Leu Glu Val Leu Arg Gly Ile Ala Ser Glu Thr His Val Val Leu Ile
                 85                  90                  95

CTG AGG GGC CCT GAA GGT TTC ACC ACG CAC CTG GAG ACC ACC TTT ACA      336
Leu Arg Gly Pro Glu Gly Phe Thr Thr His Leu Glu Thr Thr Phe Thr
            100                 105                 110

GGT GAT GGG ACC CCC AAG ACC ATC CGG GTG ACA CAG CCC CTG GGT CCC      384
Gly Asp Gly Thr Pro Lys Thr Ile Arg Val Thr Gln Pro Leu Gly Pro
        115                 120                 125

CCC ACC AAA GCC GTG GAT CTG TCC CAC CAG CCA CCG GCC GGC AAA GAA      432
Pro Thr Lys Ala Val Asp Leu Ser His Gln Pro Pro Ala Gly Lys Glu
    130                 135                 140

CAG CCC CTG GCA GTG GAT GGG GCC TCG GGT CCC GGG AAT GGG CCT CAG      480
Gln Pro Leu Ala Val Asp Gly Ala Ser Gly Pro Gly Asn Gly Pro Gln
145                 150                 155                 160

CAT GCC TAC GAT GAT GGG CAG GAG GCT GGC TCA CTC CCC CAT GCC AAC      528
His Ala Tyr Asp Asp Gly Gln Glu Ala Gly Ser Leu Pro His Ala Asn
                165                 170                 175

GGC CTG GCC CCC AGG CCC CCA GGC CAG GAC CCC GCG AAG AAA GCA ACC      576
Gly Leu Ala Pro Arg Pro Pro Gly Gln Asp Pro Ala Lys Lys Ala Thr
            180                 185                 190

AGA GTC AGC CTC CAA GGC AGA GGG GAG AAC AAT GAA CTG CTC AAG GAG      624
Arg Val Ser Leu Gln Gly Arg Gly Glu Asn Asn Glu Leu Leu Lys Glu
        195                 200                 205

ATA GAG CCT GTG CTG AGC CTT CTC ACC AGT GGG AGC AGA GGG GTC AAG      672
Ile Glu Pro Val Leu Ser Leu Leu Thr Ser Gly Ser Arg Gly Val Lys
    210                 215                 220

GGA GGG GCA CCT GCC AAG GCA GAG ATG AAA GAT ATG GGA ATC CAG GTG      720
Gly Gly Ala Pro Ala Lys Ala Glu Met Lys Asp Met Gly Ile Gln Val
225                 230                 235                 240

GAC AGA GAT TTG GAC GGC AAG TCA CAC AAA CCT CTG CCC CTC GGC GTG      768
Asp Arg Asp Leu Asp Gly Lys Ser His Lys Pro Leu Pro Leu Gly Val
                245                 250                 255

GAG AAC GAC CGA GTC TTC AAT GAC CTA TGG GGG AAG GGC AAT GTG CCT      816
Glu Asn Asp Arg Val Phe Asn Asp Leu Trp Gly Lys Gly Asn Val Pro
            260                 265                 270

GTC GTC CTC AAC AAC CCA TAT TCA GAG AAG GAG CAG CCC CCC ACC TCA      864
Val Val Leu Asn Asn Pro Tyr Ser Glu Lys Glu Gln Pro Pro Thr Ser
        275                 280                 285

GGA AAA CAG TCC CCC ACA AAG AAT GGA AGC CCC TCC AAG TGT CCA CGC      912
Gly Lys Gln Ser Pro Thr Lys Asn Gly Ser Pro Ser Lys Cys Pro Arg
    290                 295                 300

TTC CTC AAG GTC AAG AAC TGG GAG ACT GAG GTG GTT CTC ACT GAC ACC      960
Phe Leu Lys Val Lys Asn Trp Glu Thr Glu Val Val Leu Thr Asp Thr
305                 310                 315                 320

CTC CAC CTT AAG AGC ACA TTG GAA ACG GGA TGC ACT GAG TAC ATC TGC     1008
Leu His Leu Lys Ser Thr Leu Glu Thr Gly Cys Thr Glu Tyr Ile Cys
                325                 330                 335
```

```
ATG GGC TCC ATC ATG CAT CCT TCT CAG CAT GCA AGG AGG CCT GAA GAC        1056
Met Gly Ser Ile Met His Pro Ser Gln His Ala Arg Arg Pro Glu Asp
            340                 345                 350

GTC CGC ACA AAA GGA CAG CTC TTC CCT CTC GCC AAA GAG TTT ATT GAT        1104
Val Arg Thr Lys Gly Gln Leu Phe Pro Leu Ala Lys Glu Phe Ile Asp
        355                 360                 365

CAA TAC TAT TCA TCA ATT AAA AGA TTT GGC TCC AAA GCC CAC ATG GAA        1152
Gln Tyr Tyr Ser Ser Ile Lys Arg Phe Gly Ser Lys Ala His Met Glu
370                 375                 380

AGG CTG GAA GAG GTG AAC AAA GAG ATC GAC ACC ACT AGC ACT TAC CAG        1200
Arg Leu Glu Glu Val Asn Lys Glu Ile Asp Thr Thr Ser Thr Tyr Gln
385                 390                 395                 400

CTC AAG GAC ACA GAG CTC ATC TAT GGG GCC AAG CAC GCC TGG CGG AAT        1248
Leu Lys Asp Thr Glu Leu Ile Tyr Gly Ala Lys His Ala Trp Arg Asn
            405                 410                 415

GCC TCG CGC TGT GTG GGC AGG ATC CAG TGG TCC AAG CTG CAG GTA TTC        1296
Ala Ser Arg Cys Val Gly Arg Ile Gln Trp Ser Lys Leu Gln Val Phe
        420                 425                 430

GAT GCC CGT GAC TGC ACC ACG GCC CAC GGG ATG TTC AAC TAC ATC TGT        1344
Asp Ala Arg Asp Cys Thr Thr Ala His Gly Met Phe Asn Tyr Ile Cys
                435                 440                 445

AAC CAT GTC AAG TAT GCC ACC AAC AAA GGG AAC CTC AGG TCT GCC ATC        1392
Asn His Val Lys Tyr Ala Thr Asn Lys Gly Asn Leu Arg Ser Ala Ile
450                 455                 460

ACC ATA TTC CCC CAG AGG ACA GAC GGC AAG CAC GAC TTC CGA GTC TGG        1440
Thr Ile Phe Pro Gln Arg Thr Asp Gly Lys His Asp Phe Arg Val Trp
465                 470                 475                 480

AAC TCC CAG CTC ATC CGC TAC GCT GGC TAC AAG CAG CCT GAC GGC TCC        1488
Asn Ser Gln Leu Ile Arg Tyr Ala Gly Tyr Lys Gln Pro Asp Gly Ser
            485                 490                 495

ACC CTG GGG GAC CCA GCC AAT GTG CAG TTC ACA GAG ATA TGC ATA CAG        1536
Thr Leu Gly Asp Pro Ala Asn Val Gln Phe Thr Glu Ile Cys Ile Gln
        500                 505                 510

CAG GGC TGG AAA CCG CCT AGA GGC CGC TTC GAT GTC CTG CCG CTC CTG        1584
Gln Gly Trp Lys Pro Pro Arg Gly Arg Phe Asp Val Leu Pro Leu Leu
                515                 520                 525

CTT CAG GCC AAC GGC AAT GAC CCT GAG CTC TTC CAG ATT CCT CCA GAG        1632
Leu Gln Ala Asn Gly Asn Asp Pro Glu Leu Phe Gln Ile Pro Pro Glu
530                 535                 540

CTG GTG TTG GAA GTT CCC ATC AGG CAC CCC AAG TTT GAG TGG TTC AAG        1680
Leu Val Leu Glu Val Pro Ile Arg His Pro Lys Phe Glu Trp Phe Lys
545                 550                 555                 560

GAC CTG GGG CTG AAG TGG TAC GGC CTC CCC GCC GTG TCC AAC ATG CTC        1728
Asp Leu Gly Leu Lys Trp Tyr Gly Leu Pro Ala Val Ser Asn Met Leu
            565                 570                 575

CTA GAG ATT GGC GGC CTG GAG TTC AGC GCC TGT CCC TTC AGT GGC TGG        1776
Leu Glu Ile Gly Gly Leu Glu Phe Ser Ala Cys Pro Phe Ser Gly Trp
        580                 585                 590

TAC ATG GGC ACA GAG ATT GGT GTC CGC GAC TAC TGT GAC AAC TCC CGC        1824
Tyr Met Gly Thr Glu Ile Gly Val Arg Asp Tyr Cys Asp Asn Ser Arg
                595                 600                 605

TAC AAT ATC CTG GAG GAA GTG GCC AAG AAG ATG AAC TTA GAC ATG AGG        1872
Tyr Asn Ile Leu Glu Glu Val Ala Lys Lys Met Asn Leu Asp Met Arg
610                 615                 620

AAG ACG TCC TCC CTG TGG AAG GAC CAG GCG CTG GTG GAG ATC AAT ATC        1920
Lys Thr Ser Ser Leu Trp Lys Asp Gln Ala Leu Val Glu Ile Asn Ile
625                 630                 635                 640

GCG GTT CTC TAT AGC TTC CAG AGT GAC AAA GTG ACC ATT GTT GAC CAT        1968
Ala Val Leu Tyr Ser Phe Gln Ser Asp Lys Val Thr Ile Val Asp His
            645                 650                 655
```

```
CAC TCC GCC ACC GAG TCC TTC ATT AAG CAC ATG GAG AAT GAG TAC CGC    2016
His Ser Ala Thr Glu Ser Phe Ile Lys His Met Glu Asn Glu Tyr Arg
            660                 665                 670

TGC CGG GGG GGC TGC CCT GCC GAC TGG GTG TGG ATC GTG CCC CCC ATG    2064
Cys Arg Gly Gly Cys Pro Ala Asp Trp Val Trp Ile Val Pro Pro Met
            675                 680                 685

TCC GGA AGC ATC ACC CCT GTG TTC CAC CAG GAG ATG CTC AAC TAC CGG    2112
Ser Gly Ser Ile Thr Pro Val Phe His Gln Glu Met Leu Asn Tyr Arg
            690                 695                 700

CTC ACC CCC TCC TTC GAA TAC CAG CCT GAT CCC TGG AAC ACG CAT GTC    2160
Leu Thr Pro Ser Phe Glu Tyr Gln Pro Asp Pro Trp Asn Thr His Val
705                 710                 715                 720

TGG AAA GGC ACC AAC GGG ACC CCC ACA AAG CGG CGA GCC ATC GGC TTC    2208
Trp Lys Gly Thr Asn Gly Thr Pro Thr Lys Arg Arg Ala Ile Gly Phe
            725                 730                 735

AAG AAG CTA GCA GAA GCT GTC AAG TTC TCG GCC AAG CTG ATG GGG CAG    2256
Lys Lys Leu Ala Glu Ala Val Lys Phe Ser Ala Lys Leu Met Gly Gln
            740                 745                 750

GCT ATG GCC AAG AGG GTG AAA GCG ACC ATC CTC TAT GCC ACA GAG ACA    2304
Ala Met Ala Lys Arg Val Lys Ala Thr Ile Leu Tyr Ala Thr Glu Thr
            755                 760                 765

GGC AAA TCG CAA GCT TAT GCC AAG ACC TTG TGT GAG ATC TTC AAA CAC    2352
Gly Lys Ser Gln Ala Tyr Ala Lys Thr Leu Cys Glu Ile Phe Lys His
            770                 775                 780

GCC TTT GAT GCC AAG GTG ATG TCC ATG GAA GAA TAT GAC ATT GTG CAC    2400
Ala Phe Asp Ala Lys Val Met Ser Met Glu Glu Tyr Asp Ile Val His
785                 790                 795                 800

CTG GAA CAT GAA ACT CTG GTC CTT GTG GTC ACC AGC ACC TTT GGC AAT    2448
Leu Glu His Glu Thr Leu Val Leu Val Val Thr Ser Thr Phe Gly Asn
            805                 810                 815

GGA GAT CCC CCT GAG AAT GGG GAG AAA TTC GGC TGT GCT TTG ATG GAA    2496
Gly Asp Pro Pro Glu Asn Gly Glu Lys Phe Gly Cys Ala Leu Met Glu
            820                 825                 830

ATG AGG CAC CCC AAC TCT GTG CAG GAA GAA AGG AAG AGC TAC AAG GTC    2544
Met Arg His Pro Asn Ser Val Gln Glu Glu Arg Lys Ser Tyr Lys Val
            835                 840                 845

CGA TTC AAC AGC GTC TCC TCC TAC TCT GAC TCC CAA AAA TCA TCA GGC    2592
Arg Phe Asn Ser Val Ser Ser Tyr Ser Asp Ser Gln Lys Ser Ser Gly
850                 855                 860

GAT GGG CCC GAC CTC AGA GAC AAC TTT GAG AGT GCT GGA CCC CTG GCC    2640
Asp Gly Pro Asp Leu Arg Asp Asn Phe Glu Ser Ala Gly Pro Leu Ala
865                 870                 875                 880

AAT GTG AGG TTC TCA GTT TTT GGC CTC GGC TCA CGA GCA TAC CCT CAC    2688
Asn Val Arg Phe Ser Val Phe Gly Leu Gly Ser Arg Ala Tyr Pro His
            885                 890                 895

TTT TGC GCC TTC GGA CAC GCT GTG GAC ACC CTC CTG GAA GAA CTG GGA    2736
Phe Cys Ala Phe Gly His Ala Val Asp Thr Leu Leu Glu Glu Leu Gly
            900                 905                 910

GGG GAG AGG ATC CTG AAG ATG AGG GAA GGG GAT GAG CTC TGT GGG CAG    2784
Gly Glu Arg Ile Leu Lys Met Arg Glu Gly Asp Glu Leu Cys Gly Gln
            915                 920                 925

GAA GAG GCT TTC AGG ACC TGG GCC AAG AAG GTC TTC AAG GCA GCC TGT    2832
Glu Glu Ala Phe Arg Thr Trp Ala Lys Lys Val Phe Lys Ala Ala Cys
            930                 935                 940

GAT GTC TTC TGT GTG GGA GAT GAT GTC AAC ATT GAA AAG GCC AAC AAT    2880
Asp Val Phe Cys Val Gly Asp Asp Val Asn Ile Glu Lys Ala Asn Asn
945                 950                 955                 960

TCC CTC ATC AGC AAT GAT CGC AGC TGG AAG AGA AAC AAG TTC CGC CTC    2928
Ser Leu Ile Ser Asn Asp Arg Ser Trp Lys Arg Asn Lys Phe Arg Leu
```

|  |  |
|---|---|
| ACC TTT GTG GCC GAA GCT CCA GAA CTC ACA CAA GGT CTA TCC AAT GTC<br>Thr Phe Val Ala Glu Ala Pro Glu Leu Thr Gln Gly Leu Ser Asn Val<br>           980                   985               990 | 2976 |
| CAC AAA AAG CGA GTC TCA GCT GCC CGG CTC CTT AGC CGT CAA AAC CTC<br>His Lys Lys Arg Val Ser Ala Ala Arg Leu Leu Ser Arg Gln Asn Leu<br>           995                  1000             1005 | 3024 |
| CAG AGC CCT AAA TCC AGT CGG TCA ACT ATC TTC GTG CGT CTC CAC ACC<br>Gln Ser Pro Lys Ser Ser Arg Ser Thr Ile Phe Val Arg Leu His Thr<br>       1010                1015               1020 | 3072 |
| AAC GGG AGC CAG GAG CTG CAG TAC CAG CCT GGG GAC CAC CTG GGT GTC<br>Asn Gly Ser Gln Glu Leu Gln Tyr Gln Pro Gly Asp His Leu Gly Val<br>1025              1030               1035               1040 | 3120 |
| TTC CCT GGC AAC CAC GAG GAC CTC GTG AAT GCC CTG ATC GAG CGG CTG<br>Phe Pro Gly Asn His Glu Asp Leu Val Asn Ala Leu Ile Glu Arg Leu<br>               1045              1050             1055 | 3168 |
| GAG GAC GCG CCG CCT GTC AAC CAG ATG GTG AAA GTG GAA CTG CTG GAG<br>Glu Asp Ala Pro Pro Val Asn Gln Met Val Lys Val Glu Leu Leu Glu<br>           1060               1065               1070 | 3216 |
| GAG CGG AAC ACG GCT TTA GGT GTC ATC AGT AAC TGG ACA GAC GAG CTC<br>Glu Arg Asn Thr Ala Leu Gly Val Ile Ser Asn Trp Thr Asp Glu Leu<br>       1075                1080               1085 | 3264 |
| CGC CTC CCA CCC TGC ACC ATC TTC CAG GCC TTC AAG TAC TAC CTG GAC<br>Arg Leu Pro Pro Cys Thr Ile Phe Gln Ala Phe Lys Tyr Tyr Leu Asp<br>       1090                1095               1100 | 3312 |
| ATC ACC ACG CCA CCA ACG CCC CTG CAG CTG CAG CAG TTT GCC TCC CTA<br>Ile Thr Thr Pro Pro Thr Pro Leu Gln Leu Gln Gln Phe Ala Ser Leu<br>1105              1110               1115               1120 | 3360 |
| GCT ACC AGC GAG AAG GAG AAG CAG CGT CTG CTG GTC CTC AGC AAG GGT<br>Ala Thr Ser Glu Lys Glu Lys Gln Arg Leu Leu Val Leu Ser Lys Gly<br>           1125               1130               1135 | 3408 |
| TTG CAG GAG TAC GAG GAA TGG AAA TGG GGC AAG AAC CCC ACC ATC GTG<br>Leu Gln Glu Tyr Glu Glu Trp Lys Trp Gly Lys Asn Pro Thr Ile Val<br>               1140              1145               1150 | 3456 |
| GAG GTG CTG GAG GAG TTC CCA TCT ATC CAG ATG CCG GCC ACC CTG CTC<br>Glu Val Leu Glu Glu Phe Pro Ser Ile Gln Met Pro Ala Thr Leu Leu<br>           1155               1160               1165 | 3504 |
| CTG ACC CAG CTG TCC CTG CTG CAG CCC CGC TAC TAT TCC ATC AGC TCC<br>Leu Thr Gln Leu Ser Leu Leu Gln Pro Arg Tyr Tyr Ser Ile Ser Ser<br>       1170                1175               1180 | 3552 |
| TCC CCA GAC ATG TAC CCT GAT GAA GTG CAC CTC ACT GTG GCC ATC GTT<br>Ser Pro Asp Met Tyr Pro Asp Glu Val His Leu Thr Val Ala Ile Val<br>1185              1190               1195               1200 | 3600 |
| TCC TAC CGC ACT CGA GAT GGA GAA GGA CCA ATT CAC CAC GGC GTA TGC<br>Ser Tyr Arg Thr Arg Asp Gly Glu Gly Pro Ile His His Gly Val Cys<br>               1205              1210             1215 | 3648 |
| TCC TCC TGG CTC AAC CGG ATA CAG GCT GAC GAA CTG GTC CCC TGT TTC<br>Ser Ser Trp Leu Asn Arg Ile Gln Ala Asp Glu Leu Val Pro Cys Phe<br>           1220               1225               1230 | 3696 |
| GTG AGA GGA GCA CCC AGC TTC CAC CTG CCC CGG AAC CCC CAA GTC CCC<br>Val Arg Gly Ala Pro Ser Phe His Leu Pro Arg Asn Pro Gln Val Pro<br>               1235              1240             1245 | 3744 |
| TGC ATC CTC GTT GGA CCA GGC ACC GGC ATT GCC CCT TTC CGA AGC TTC<br>Cys Ile Leu Val Gly Pro Gly Thr Gly Ile Ala Pro Phe Arg Ser Phe<br>       1250                1255               1260 | 3792 |
| TGG CAA CAG CGG CAA TTT GAT ATC CAA CAC AAA GGA ATG AAC CCC TGC<br>Trp Gln Gln Arg Gln Phe Asp Ile Gln His Lys Gly Met Asn Pro Cys<br>1265              1270               1275               1280 | 3840 |
| CCC ATG GTC CTG GTC TTC GGG TGC CGG CAA TCC AAG ATA GAT CAT ATC | 3888 |

```
Pro Met Val Leu Val Phe Gly Cys Arg Gln Ser Lys Ile Asp His Ile
            1285                1290                1295

TAC AGG GAA GAG ACC CTG CAG GCC AAG AAC AAG GGG GTC TTC AGA GAG      3936
Tyr Arg Glu Glu Thr Leu Gln Ala Lys Asn Lys Gly Val Phe Arg Glu
            1300                1305                1310

CTG TAC ACG GCT TAC TCC CGG GAG CCA GAC AAA CCA AAG AAG TAC GTG      3984
Leu Tyr Thr Ala Tyr Ser Arg Glu Pro Asp Lys Pro Lys Lys Tyr Val
            1315                1320                1325

CAG GAC ATC CTG CAG GAG CAG CTG GCG GAG TCT GTG TAC CGA GCC CTG      4032
Gln Asp Ile Leu Gln Glu Gln Leu Ala Glu Ser Val Tyr Arg Ala Leu
            1330                1335                1340

AAG GAG CAA GGG GGC CAC ATA TAC GTC TGT GGG GAC GTC ACC ATG GCT      4080
Lys Glu Gln Gly Gly His Ile Tyr Val Cys Gly Asp Val Thr Met Ala
1345                1350                1355                1360

GCT GAT GTC CTC AAA GCC ATC CAG CGC ATC ATG ACC CAG CAG GGG AAG      4128
Ala Asp Val Leu Lys Ala Ile Gln Arg Ile Met Thr Gln Gln Gly Lys
            1365                1370                1375

CTC TCG GCA GAG GAC GCC GGC GTA TTC ATC AGC CGG ATG AGG GAT GAC      4176
Leu Ser Ala Glu Asp Ala Gly Val Phe Ile Ser Arg Met Arg Asp Asp
            1380                1385                1390

AAC CGA TAC CAT GAG GAT ATT TTT GGA GTC ACC CTG CGA ACG TAC GAA      4224
Asn Arg Tyr His Glu Asp Ile Phe Gly Val Thr Leu Arg Thr Tyr Glu
            1395                1400                1405

GTG ACC AAC CGC CTT AGA TCT GAG TCC ATT GCC TTC ATT GAA GAG AGC      4272
Val Thr Asn Arg Leu Arg Ser Glu Ser Ile Ala Phe Ile Glu Glu Ser
            1410                1415                1420

AAA AAA GAC ACC GAT GAG GTT TTC AGC TCC TAACTGGACC CTCTTGCCCA        4322
Lys Lys Asp Thr Asp Glu Val Phe Ser Ser
1425                1430                1435

GCCGGCTGCA AGTTTGTAAG CGCGGGACAG A                                   4353

(2) INFORMATION FOR SEQ ID NO:19:

(i) SEQUENCE CHARACTERISTICS:
        (A) LENGTH: 1434 amino acids
        (B) TYPE: amino acid
        (D) TOPOLOGY: linear (ii) MOLECULE TYPE: protein (xi) SEQUENCE DESCRIPTION: SEQ ID NO:19:

Met Glu Asp His Met Phe Gly Val Gln Gln Ile Gln Pro Asn Val Ile
1               5                   10                  15

Ser Val Arg Leu Phe Lys Arg Lys Val Gly Gly Leu Gly Phe Leu Val
            20                  25                  30

Lys Glu Arg Val Ser Lys Pro Pro Val Ile Ile Ser Asp Leu Ile Arg
        35                  40                  45

Gly Gly Ala Ala Glu Gln Ser Gly Leu Ile Gln Ala Gly Asp Ile Ile
    50                  55                  60

Leu Ala Val Asn Gly Arg Pro Leu Val Asp Leu Ser Tyr Asp Ser Ala
65                  70                  75                  80

Leu Glu Val Leu Arg Gly Ile Ala Ser Glu Thr His Val Val Leu Ile
                85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
        115                 120                 125

Pro Thr Lys Ala Val Asp Leu Ser His Gln Pro Pro Ala Gly Lys Glu
    130                 135                 140
```

-continued

```
Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
            165                 170                 175

Gly Leu Ala Pro Arg Pro Gly Gln Asp Pro Ala Lys Lys Ala Thr
                180                 185                 190

Arg Val Ser Leu Gln Gly Arg Gly Glu Asn Asn Glu Leu Leu Lys Glu
            195                 200                 205

Ile Glu Pro Val Leu Ser Leu Leu Thr Ser Gly Ser Arg Gly Val Lys
        210                 215                 220

Gly Gly Ala Pro Ala Lys Ala Glu Met Lys Asp Met Gly Ile Gln Val
225                 230                 235                 240

Asp Arg Asp Leu Asp Gly Lys Ser His Lys Pro Leu Pro Leu Gly Val
                245                 250                 255

Glu Asn Asp Arg Val Phe Asn Asp Leu Trp Gly Lys Gly Asn Val Pro
            260                 265                 270

Val Val Leu Asn Asn Pro Tyr Ser Glu Lys Glu Gln Pro Pro Thr Ser
        275                 280                 285

Gly Lys Gln Ser Pro Thr Lys Asn Gly Ser Pro Ser Lys Cys Pro Arg
290                 295                 300

Phe Leu Lys Val Lys Asn Trp Glu Thr Glu Val Val Leu Thr Asp Thr
305                 310                 315                 320

Leu His Leu Lys Ser Thr Leu Glu Thr Gly Cys Thr Glu Tyr Ile Cys
            325                 330                 335

Met Gly Ser Ile Met His Pro Ser Gln His Ala Arg Arg Pro Glu Asp
                340                 345                 350

Val Arg Thr Lys Gly Gln Leu Phe Pro Leu Ala Lys Glu Phe Ile Asp
            355                 360                 365

Gln Tyr Tyr Ser Ser Ile Lys Arg Phe Gly Ser Lys Ala His Met Glu
        370                 375                 380

Arg Leu Glu Glu Val Asn Lys Glu Ile Asp Thr Thr Ser Thr Tyr Gln
385                 390                 395                 400

Leu Lys Asp Thr Glu Leu Ile Tyr Gly Ala Lys His Ala Trp Arg Asn
                405                 410                 415

Ala Ser Arg Cys Val Gly Arg Ile Gln Trp Ser Lys Leu Gln Val Phe
            420                 425                 430

Asp Ala Arg Asp Cys Thr Thr Ala His Gly Met Phe Asn Tyr Ile Cys
        435                 440                 445

Asn His Val Lys Tyr Ala Thr Asn Lys Gly Asn Leu Arg Ser Ala Ile
    450                 455                 460

Thr Ile Phe Pro Gln Arg Thr Asp Gly Lys His Asp Phe Arg Val Trp
465                 470                 475                 480

Asn Ser Gln Leu Ile Arg Tyr Ala Gly Tyr Lys Gln Pro Asp Gly Ser
                485                 490                 495

Thr Leu Gly Asp Pro Ala Asn Val Gln Phe Thr Glu Ile Cys Ile Gln
            500                 505                 510

Gln Gly Trp Lys Pro Pro Arg Gly Arg Phe Asp Val Leu Pro Leu Leu
        515                 520                 525

Leu Gln Ala Asn Gly Asn Asp Pro Glu Leu Phe Gln Ile Pro Pro Glu
    530                 535                 540

Leu Val Leu Glu Val Pro Ile Arg His Pro Lys Phe Glu Trp Phe Lys
545                 550                 555                 560
```

-continued

```
Asp Leu Gly Leu Lys Trp Tyr Gly Leu Pro Ala Val Ser Asn Met Leu
            565                 570                 575

Leu Glu Ile Gly Gly Leu Glu Phe Ser Ala Cys Pro Phe Ser Gly Trp
        580                 585                 590

Tyr Met Gly Thr Glu Ile Gly Val Arg Asp Tyr Cys Asp Asn Ser Arg
        595                 600                 605

Tyr Asn Ile Leu Glu Glu Val Ala Lys Lys Met Asn Leu Asp Met Arg
    610                 615                 620

Lys Thr Ser Ser Leu Trp Lys Asp Gln Ala Leu Val Glu Ile Asn Ile
625                 630                 635                 640

Ala Val Leu Tyr Ser Phe Gln Ser Asp Lys Val Thr Ile Val Asp His
                645                 650                 655

His Ser Ala Thr Glu Ser Phe Ile Lys His Met Glu Asn Glu Tyr Arg
                660                 665                 670

Cys Arg Gly Gly Cys Pro Ala Asp Trp Val Trp Ile Val Pro Pro Met
            675                 680                 685

Ser Gly Ser Ile Thr Pro Val Phe His Gln Glu Met Leu Asn Tyr Arg
        690                 695                 700

Leu Thr Pro Ser Phe Glu Tyr Gln Pro Asp Pro Trp Asn Thr His Val
705                 710                 715                 720

Trp Lys Gly Thr Asn Gly Thr Pro Thr Lys Arg Arg Ala Ile Gly Phe
                725                 730                 735

Lys Lys Leu Ala Glu Ala Val Lys Phe Ser Ala Lys Leu Met Gly Gln
            740                 745                 750

Ala Met Ala Lys Arg Val Lys Ala Thr Ile Leu Tyr Ala Thr Glu Thr
        755                 760                 765

Gly Lys Ser Gln Ala Tyr Ala Lys Thr Leu Cys Glu Ile Phe Lys His
        770                 775                 780

Ala Phe Asp Ala Lys Val Met Ser Met Glu Glu Tyr Asp Ile Val His
785                 790                 795                 800

Leu Glu His Glu Thr Leu Val Leu Val Val Thr Ser Thr Phe Gly Asn
                805                 810                 815

Gly Asp Pro Pro Glu Asn Gly Glu Lys Phe Gly Cys Ala Leu Met Glu
            820                 825                 830

Met Arg His Pro Asn Ser Val Gln Glu Glu Arg Lys Ser Tyr Lys Val
        835                 840                 845

Arg Phe Asn Ser Val Ser Ser Tyr Ser Asp Ser Gln Lys Ser Ser Gly
    850                 855                 860

Asp Gly Pro Asp Leu Arg Asp Asn Phe Glu Ser Ala Gly Pro Leu Ala
865                 870                 875                 880

Asn Val Arg Phe Ser Val Phe Gly Leu Gly Ser Arg Ala Tyr Pro His
                885                 890                 895

Phe Cys Ala Phe Gly His Ala Val Asp Thr Leu Leu Glu Glu Leu Gly
                900                 905                 910

Gly Glu Arg Ile Leu Lys Met Arg Glu Gly Asp Glu Leu Cys Gly Gln
            915                 920                 925

Glu Glu Ala Phe Arg Thr Trp Ala Lys Lys Val Phe Lys Ala Ala Cys
        930                 935                 940

Asp Val Phe Cys Val Gly Asp Asp Val Asn Ile Glu Lys Ala Asn Asn
945                 950                 955                 960

Ser Leu Ile Ser Asn Asp Arg Ser Trp Lys Arg Asn Lys Phe Arg Leu
                965                 970                 975

Thr Phe Val Ala Glu Ala Pro Glu Leu Thr Gln Gly Leu Ser Asn Val
```

-continued

```
                     980                 985                 990
His Lys Lys Arg Val Ser Ala Ala Arg Leu Leu Ser Arg Gln Asn Leu
                995                1000                1005

Gln Ser Pro Lys Ser Ser Arg Ser Thr Ile Phe Val Arg Leu His Thr
    1010                1015                1020

Asn Gly Ser Gln Glu Leu Gln Tyr Gln Pro Gly Asp His Leu Gly Val
1025                1030                1035                1040

Phe Pro Gly Asn His Glu Asp Leu Val Asn Ala Leu Ile Glu Arg Leu
                1045                1050                1055

Glu Asp Ala Pro Pro Val Asn Gln Met Val Lys Val Glu Leu Leu Glu
                1060                1065                1070

Glu Arg Asn Thr Ala Leu Gly Val Ile Ser Asn Trp Thr Asp Glu Leu
                1075                1080                1085

Arg Leu Pro Pro Cys Thr Ile Phe Gln Ala Phe Lys Tyr Tyr Leu Asp
                1090                1095                1100

Ile Thr Thr Pro Pro Thr Pro Leu Gln Leu Gln Gln Phe Ala Ser Leu
1105                1110                1115                1120

Ala Thr Ser Glu Lys Glu Lys Gln Arg Leu Leu Val Leu Ser Lys Gly
                1125                1130                1135

Leu Gln Glu Tyr Glu Glu Trp Lys Trp Gly Lys Asn Pro Thr Ile Val
                1140                1145                1150

Glu Val Leu Glu Glu Phe Pro Ser Ile Gln Met Pro Ala Thr Leu Leu
                1155                1160                1165

Leu Thr Gln Leu Ser Leu Leu Gln Pro Arg Tyr Tyr Ser Ile Ser Ser
    1170                1175                1180

Ser Pro Asp Met Tyr Pro Asp Glu Val His Leu Thr Val Ala Ile Val
1185                1190                1195                1200

Ser Tyr Arg Thr Arg Asp Gly Glu Gly Pro Ile His His Gly Val Cys
                1205                1210                1215

Ser Ser Trp Leu Asn Arg Ile Gln Ala Asp Glu Leu Val Pro Cys Phe
                1220                1225                1230

Val Arg Gly Ala Pro Ser Phe His Leu Pro Arg Asn Pro Gln Val Pro
                1235                1240                1245

Cys Ile Leu Val Gly Pro Gly Thr Gly Ile Ala Pro Phe Arg Ser Phe
    1250                1255                1260

Trp Gln Gln Arg Gln Phe Asp Ile Gln His Lys Gly Met Asn Pro Cys
1265                1270                1275                1280

Pro Met Val Leu Val Phe Gly Cys Arg Gln Ser Lys Ile Asp His Ile
                1285                1290                1295

Tyr Arg Glu Glu Thr Leu Gln Ala Lys Asn Lys Gly Val Phe Arg Glu
                1300                1305                1310

Leu Tyr Thr Ala Tyr Ser Arg Glu Pro Asp Lys Pro Lys Lys Tyr Val
                1315                1320                1325

Gln Asp Ile Leu Gln Glu Gln Leu Ala Glu Ser Val Tyr Arg Ala Leu
    1330                1335                1340

Lys Glu Gln Gly Gly His Ile Tyr Val Cys Gly Asp Val Thr Met Ala
1345                1350                1355                1360

Ala Asp Val Leu Lys Ala Ile Gln Arg Ile Met Thr Gln Gln Gly Lys
                1365                1370                1375

Leu Ser Ala Glu Asp Ala Gly Val Phe Ile Ser Arg Met Arg Asp Asp
                1380                1385                1390

Asn Arg Tyr His Glu Asp Ile Phe Gly Val Thr Leu Arg Thr Tyr Glu
                1395                1400                1405
```

```
Val Thr Asn Arg Leu Arg Ser Glu Ser Ile Ala Phe Ile Glu Glu Ser
    1410                1415                1420

Lys Lys Asp Thr Asp Glu Val Phe Ser Ser
1425                1430

(2) INFORMATION FOR SEQ ID NO:20:

(i) SEQUENCE CHARACTERISTICS:
        (A) LENGTH: 4780 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: Human NOS-SN gene, Nakane, et al,
            FEBS Lett 316:175 (1993)

(ix) FEATURE:
        (A) NAME/KEY: CDS
        (B) LOCATION: 431..4732

(xi) SEQUENCE DESCRIPTION: SEQ ID NO:20:
```

| | |
|---|---:|
| GAGCGGACGG GCTCATGATG CCTCAGATCT GATCCGCATC TAACAGGCTG GCAATGAAGA | 60 |
| TACCCAGAGA ATAGTTCACA TCTATCATGC GTCACTTCTA GACACAGCCA TCAGACGCAT | 120 |
| CTCCTCCCCT TTCTGCCTGA CCTTAGGACA CGTCCCACCG CCTCTCTTGA CGTCTGCCTG | 180 |
| GTCAACCATC ACTTCCTTAG AGAATAAGGA GAGAGGCGGA TGCAGGAAAT CATGCCACCG | 240 |
| ACGGGCCACC AGCCATGAGT GGGTGACGCT GAGCTGACGT CAAAGACAGA GAGGGCTGAA | 300 |
| GCCTTGTCAG CACCTGTCAC CCCGGCTCCT GCTCTCCGTG TAGCCTGAAG CCTGGATCCT | 360 |
| CCTGGTGAAA TCATCTTGGC CTGATAGCAT TGTGAGGTCT TCAGACAGGA CCCCTCGGAA | 420 |

```
GCTAGTTACC ATG GAG GAT CAC ATG TTC GGT GTT CAG CAA ATC CAG CCC        469
           Met Glu Asp His Met Phe Gly Val Gln Gln Ile Gln Pro
             1               5                  10

AAT GTC ATT TCT GTT CGT CTC TTC AAG CGC AAA GTT GGG GGC CTG GGA       517
Asn Val Ile Ser Val Arg Leu Phe Lys Arg Lys Val Gly Gly Leu Gly
 15                  20                  25

TTT CTG GTG AAG GAG CGG GTC AGT AAG CCG CCC GTG ATC ATC TCT GAC       565
Phe Leu Val Lys Glu Arg Val Ser Lys Pro Pro Val Ile Ile Ser Asp
 30                  35                  40                  45

CTG ATT CGT GGG GGC GCC GCA GAG CAG AGT GGC CTC ATC CAG GCC GGA       613
Leu Ile Arg Gly Gly Ala Ala Glu Gln Ser Gly Leu Ile Gln Ala Gly
                 50                  55                  60

GAC ATC ATT CTT GCG GTC AAC GGC CGG CCC TTG GTG GAC CTG AGC TAT       661
Asp Ile Ile Leu Ala Val Asn Gly Arg Pro Leu Val Asp Leu Ser Tyr
                 65                  70                  75

GAC AGC GCC CTG GAG GTA CTC AGA GGC ATT GCC TCT GAG ACC CAC GTG       709
Asp Ser Ala Leu Glu Val Leu Arg Gly Ile Ala Ser Glu Thr His Val
                 80                  85                  90

GTC CTC ATT CTG AGG GGC CCT GAA GGT TTC ACC ACG CAC CTG GAG ACC       757
Val Leu Ile Leu Arg Gly Pro Glu Gly Phe Thr Thr His Leu Glu Thr
                 95                 100                 105

ACC TTT ACA GGT GAT GGG ACC CCC AAG ACC ATC GGT GTG ACA CAG CCC       805
Thr Phe Thr Gly Asp Gly Thr Pro Lys Thr Ile Arg Val Thr Gln Pro
110                 115                 120                 125

CTG GGT CCC CCC ACC AAA GCC GTG GAT CTG TCC CAC CAG CCA CCG GCC       853
```

```
Leu Gly Pro Pro Thr Lys Ala Val Asp Leu Ser His Gln Pro Pro Ala
            130                 135                 140

GGC AAA GAA CAG CCC CTG GCA GTG GAT GGG GCC TCG GGT CCC GGG AAT        901
Gly Lys Glu Gln Pro Leu Ala Val Asp Gly Ala Ser Gly Pro Gly Asn
        145                 150                 155

GGG CCT CAG CAT GCC TAC GAT GAT GGG CAG GAG GCT GGC TCA CTC CCC        949
Gly Pro Gln His Ala Tyr Asp Asp Gly Gln Glu Ala Gly Ser Leu Pro
            160                 165                 170

CAT GCC AAC GGC TGG CCC CAG GCC CCC AGG CAG GAC CCC GCG AAG AAA        997
His Ala Asn Gly Trp Pro Gln Ala Pro Arg Gln Asp Pro Ala Lys Lys
        175                 180                 185

GCA ACC AGA GTC AGC CTC CAA GGC AGA GGG GAG AAC AAT GAA CTG CTC       1045
Ala Thr Arg Val Ser Leu Gln Gly Arg Gly Glu Asn Asn Glu Leu Leu
190                 195                 200                 205

AAG GAG ATA GAG CCT GTG CTG AGC CTT CTC ACC AGT GGG AGC AGA GGG       1093
Lys Glu Ile Glu Pro Val Leu Ser Leu Leu Thr Ser Gly Ser Arg Gly
                210                 215                 220

GTC AAG GGA GGG GCA CCT GCC AAG GCA GAG ATG AAA GAT ATG GGA ATC       1141
Val Lys Gly Gly Ala Pro Ala Lys Ala Glu Met Lys Asp Met Gly Ile
            225                 230                 235

CAG GTG GAC AGA GAT TTG GAC GGC AAG TCA CAC AAA CCT CTG CCC CTC       1189
Gln Val Asp Arg Asp Leu Asp Gly Lys Ser His Lys Pro Leu Pro Leu
        240                 245                 250

GGC GTG GAG AAC GAC CGA GTC TTC AAT GAC CTA TGG GGG AAG GGC AAT       1237
Gly Val Glu Asn Asp Arg Val Phe Asn Asp Leu Trp Gly Lys Gly Asn
255                 260                 265

GTG CCT GTC GTC CTC AAC AAC CCA TAT TCA GAG AAG GAG CAG CCC CCC       1285
Val Pro Val Val Leu Asn Asn Pro Tyr Ser Glu Lys Glu Gln Pro Pro
270                 275                 280                 285

ACC TCA GGA AAA CAG TCC CCC ACA AAG AAT GGC AGC CCC TCC AAG TGT       1333
Thr Ser Gly Lys Gln Ser Pro Thr Lys Asn Gly Ser Pro Ser Lys Cys
                290                 295                 300

CCA CGC TTC CTC AAG GTC AAG AAC TGG GAG ACT GAG GTG GTT CTC ACT       1381
Pro Arg Phe Leu Lys Val Lys Asn Trp Glu Thr Glu Val Val Leu Thr
            305                 310                 315

GAC ACC CTC CAC CTT AAG AGC ACA TTG GAA ACG GGA TGC ACT GAG TAC       1429
Asp Thr Leu His Leu Lys Ser Thr Leu Glu Thr Gly Cys Thr Glu Tyr
        320                 325                 330

ATC TGC ATG GGC TCC ATC ATG CAT CCT TCT CAG CAT GCA AGG AGG CCT       1477
Ile Cys Met Gly Ser Ile Met His Pro Ser Gln His Ala Arg Arg Pro
    335                 340                 345

GAA GAC GTC CGC ACA AAA GGA CAG CTC TTC CCT CTC GCC AAA GAG TTT       1525
Glu Asp Val Arg Thr Lys Gly Gln Leu Phe Pro Leu Ala Lys Glu Phe
350                 355                 360                 365

ATT GAT CAA TAC TAT TCA TCA ATT AAA AGA TTT GGC TCC AAA GCC CAC       1573
Ile Asp Gln Tyr Tyr Ser Ser Ile Lys Arg Phe Gly Ser Lys Ala His
                370                 375                 380

ATG GAA AGG CTG GAA GAG GTG AAC AAA GAG ATC GAC ACC ACT AGC ACT       1621
Met Glu Arg Leu Glu Glu Val Asn Lys Glu Ile Asp Thr Thr Ser Thr
            385                 390                 395

TAC CAG CTC AAG GAC ACA GAG CTC ATC TAT GGG GCC AAG CAC GCC TGG       1669
Tyr Gln Leu Lys Asp Thr Glu Leu Ile Tyr Gly Ala Lys His Ala Trp
        400                 405                 410

CGG AAT GCC TCG CGC TGT GTG GGC AGG ATC CAG TGG TCC AAG CTG CAG       1717
Arg Asn Ala Ser Arg Cys Val Gly Arg Ile Gln Trp Ser Lys Leu Gln
    415                 420                 425

GTA TTC GAT GCC CGT GAC TGC ACC ACG GCC CAC GGG ATG TTC AAC TAC       1765
Val Phe Asp Ala Arg Asp Cys Thr Thr Ala His Gly Met Phe Asn Tyr
430                 435                 440                 445
```

```
ATC TGT AAC CAT GTC AAG TAT GCC ACC AAC AAA GGG AAC CTC AGG TCT       1813
Ile Cys Asn His Val Lys Tyr Ala Thr Asn Lys Gly Asn Leu Arg Ser
            450                 455                 460

GCC ATC ACC ATA TTC CCC CAG AGG ACA GAC GGC AAG CAC GAC TTC CGA       1861
Ala Ile Thr Ile Phe Pro Gln Arg Thr Asp Gly Lys His Asp Phe Arg
        465                 470                 475

GTC TGG AAC TCC CAG CTC ATC CGC TAC GCT GGC TAC AAG CAC CGT GAC       1909
Val Trp Asn Ser Gln Leu Ile Arg Tyr Ala Gly Tyr Lys His Arg Asp
        480                 485                 490

GGC TCC ACC CTG GGG GAC CCA GCC AAT GTG CAG TTC ACA GAG ATA TGC       1957
Gly Ser Thr Leu Gly Asp Pro Ala Asn Val Gln Phe Thr Glu Ile Cys
    495                 500                 505

ATA CAG CAG GGC TGG AAA CCG CCT AGA GGC CGC TTC GAT GTC CTG CCG       2005
Ile Gln Gln Gly Trp Lys Pro Pro Arg Gly Arg Phe Asp Val Leu Pro
510                 515                 520                 525

CTC CTG CTT CAG GCC AAC GGC AAT GAC CCT GAG CTC TTC CAG ATT CCT       2053
Leu Leu Leu Gln Ala Asn Gly Asn Asp Pro Glu Leu Phe Gln Ile Pro
                530                 535                 540

CCA GAG CTG GTG TTG GAA CTT CCC ATC AGG CAC CCC AAG TTT GAG TGG       2101
Pro Glu Leu Val Leu Glu Leu Pro Ile Arg His Pro Lys Phe Glu Trp
            545                 550                 555

TTC AAG GAC CTG GCG CTG AAG TGG TAC GGC CTC CCC GCC GTG TCC AAC       2149
Phe Lys Asp Leu Ala Leu Lys Trp Tyr Gly Leu Pro Ala Val Ser Asn
        560                 565                 570

ATG CTC CTA GAG ATT GGC GGC CTG GAG TTC AGC GCC TGT CCC TTC AGT       2197
Met Leu Leu Glu Ile Gly Gly Leu Glu Phe Ser Ala Cys Pro Phe Ser
    575                 580                 585

GGC TGG TAC ATG GGC ACA GAG ATT GGT GTC CGC GAC TAC TGT GAC AAC       2245
Gly Trp Tyr Met Gly Thr Glu Ile Gly Val Arg Asp Tyr Cys Asp Asn
590                 595                 600                 605

TCC CGC TAC AAT ATC CTG GAG GAA GTG GCC AAG AAG ATG AAC TTA GAC       2293
Ser Arg Tyr Asn Ile Leu Glu Glu Val Ala Lys Lys Met Asn Leu Asp
                610                 615                 620

ATG AGG AAG ACG TCC TCC CTG TGG AAG GAC CAG GCG CTG GTG GAG ATC       2341
Met Arg Lys Thr Ser Ser Leu Trp Lys Asp Gln Ala Leu Val Glu Ile
            625                 630                 635

AAT ATC GCG GTT CTC TAT AGC TTC CAG AGT GAC AAA GTG ACC ATT GTT       2389
Asn Ile Ala Val Leu Tyr Ser Phe Gln Ser Asp Lys Val Thr Ile Val
        640                 645                 650

GAC CAT CAC TCC GCC ACC GAG TCC TTC ATT AAG CAC ATG GAG AAT GAG       2437
Asp His His Ser Ala Thr Glu Ser Phe Ile Lys His Met Glu Asn Glu
    655                 660                 665

TAC CGC TGC CGG GGG GGC TGC CCT GCC GAC TGG GTG TGG ATC GTG CCC       2485
Tyr Arg Cys Arg Gly Gly Cys Pro Ala Asp Trp Val Trp Ile Val Pro
670                 675                 680                 685

CCC ATG TCC GGA AGC ATC ACC CCT GTG TTC CAC CAG GAG ATG CTC AAC       2533
Pro Met Ser Gly Ser Ile Thr Pro Val Phe His Gln Glu Met Leu Asn
                690                 695                 700

TAC CGG CTC ACC CCC TCC TTC GAA TAC CAG CCT GAT CCC TGG AAC ACG       2581
Tyr Arg Leu Thr Pro Ser Phe Glu Tyr Gln Pro Asp Pro Trp Asn Thr
            705                 710                 715

CAT GTC TGG AAA GGC ACC AAC GGG ACC CCC ACA AAG CGG CGA GCC ATC       2629
His Val Trp Lys Gly Thr Asn Gly Thr Pro Thr Lys Arg Arg Ala Ile
        720                 725                 730

GGC TTC AAG AAG CTA GCA GAA GCT GTC AAG TTC TCG GCC AAG CTG ATG       2677
Gly Phe Lys Lys Leu Ala Glu Ala Val Lys Phe Ser Ala Lys Leu Met
    735                 740                 745

GGG CAG GCT ATG GCC AAG AGG GTG AAA GCG ACC ATC CTC TAT GCC ACA       2725
Gly Gln Ala Met Ala Lys Arg Val Lys Ala Thr Ile Leu Tyr Ala Thr
750                 755                 760                 765
```

```
GAG ACA GGC AAA TCG CAA GCT TAT GCC AAG ACC TTG TGT GAG ATC TTC     2773
Glu Thr Gly Lys Ser Gln Ala Tyr Ala Lys Thr Leu Cys Glu Ile Phe
            770                 775                 780

AAA CAC GCC TTT GAT GCC AAG GTG ATG TCC ATG GAA GAA TAT GAC ATT     2821
Lys His Ala Phe Asp Ala Lys Val Met Ser Met Glu Glu Tyr Asp Ile
                785                 790                 795

GTG CAC CTG GAA CAT GAA ACT CTG GTC CTT GTG GTC ACC AGC ACC TTT     2869
Val His Leu Glu His Glu Thr Leu Val Leu Val Val Thr Ser Thr Phe
        800                 805                 810

GGC AAT GGA GAT CCC CCT GAG AAT GGG GAG AAA TTC GGC TGT GCT TTG     2917
Gly Asn Gly Asp Pro Pro Glu Asn Gly Glu Lys Phe Gly Cys Ala Leu
    815                 820                 825

ATG GAA ATG AGG CAC CCC AAC TCT GTG CAG GAA GAA AGG AAG AGC TAC     2965
Met Glu Met Arg His Pro Asn Ser Val Gln Glu Glu Arg Lys Ser Tyr
830                 835                 840                 845

AAG GTC CGA TTC AAC AGC GTC TCC TCC TAC TCT GAC TCC CAA AAA TCA     3013
Lys Val Arg Phe Asn Ser Val Ser Ser Tyr Ser Asp Ser Gln Lys Ser
                850                 855                 860

TCA GGC GAT GGG CCC GAC CTC AGA GAC AAC TTT GAG AGT GCT GGA CCC     3061
Ser Gly Asp Gly Pro Asp Leu Arg Asp Asn Phe Glu Ser Ala Gly Pro
            865                 870                 875

CTG GCC AAT GTG AGG TTC TCA GTT TTT GGC CTC GGC TCA CGA GCA TAC     3109
Leu Ala Asn Val Arg Phe Ser Val Phe Gly Leu Gly Ser Arg Ala Tyr
        880                 885                 890

CCT CAC TTT TGC GCC TTC GGA CAC GCT GTG GAC ACC CTC CTG GAA GAA     3157
Pro His Phe Cys Ala Phe Gly His Ala Val Asp Thr Leu Leu Glu Glu
    895                 900                 905

CTG GGA GGG GAG AGG ATC CTG AAG ATG AGG GAA GGG GAT GAG CTC TGT     3205
Leu Gly Gly Glu Arg Ile Leu Lys Met Arg Glu Gly Asp Glu Leu Cys
910                 915                 920                 925

GGG CAG GAA GAG GCT TTC AGG ACC TGG GCC AAG AAG GTC TTC AAG GCA     3253
Gly Gln Glu Glu Ala Phe Arg Thr Trp Ala Lys Lys Val Phe Lys Ala
                930                 935                 940

GCC TGT GAT GTC TTC TGT GTG GGA GAT GAT GTC AAC ATT GAA AAG GCC     3301
Ala Cys Asp Val Phe Cys Val Gly Asp Asp Val Asn Ile Glu Lys Ala
            945                 950                 955

AAC AAT TCC CTC ATC AGC AAT GAT CGC AGC TGG AAG AGA AAC AAG TTC     3349
Asn Asn Ser Leu Ile Ser Asn Asp Arg Ser Trp Lys Arg Asn Lys Phe
        960                 965                 970

CGC CTC ACC TTT GTG GCC GAA GCT CCA GAA CTC ACA CAA GGT CTA TCC     3397
Arg Leu Thr Phe Val Ala Glu Ala Pro Glu Leu Thr Gln Gly Leu Ser
    975                 980                 985

AAT GTC CAC AAA AAG CGA GTC TCA GCT GCC CGG CTC CTT AGC CGT CAA     3445
Asn Val His Lys Lys Arg Val Ser Ala Ala Arg Leu Leu Ser Arg Gln
990                 995                 1000                1005

AAC CTC CAG AGC CCT AAA TCC AGT CGG TCA ACT ATC TTC GTG CGT CTC     3493
Asn Leu Gln Ser Pro Lys Ser Ser Arg Ser Thr Ile Phe Val Arg Leu
                1010                1015                1020

CAC ACC AAC GGG AGC CAG GAG CTG CAG TAC CAG CCT GGG GAC CAC CTG     3541
His Thr Asn Gly Ser Gln Glu Leu Gln Tyr Gln Pro Gly Asp His Leu
            1025                1030                1035

GGT GTC TTC CCT GGC AAC CAC GAG GAC CTC GTG AAT GCC CTG ATC GAG     3589
Gly Val Phe Pro Gly Asn His Glu Asp Leu Val Asn Ala Leu Ile Glu
        1040                1045                1050

CGG CTG GAG GAC GCG CCG CCT GTC AAC CAG ATG GTG AAA GTG GAA CTG     3637
Arg Leu Glu Asp Ala Pro Pro Val Asn Gln Met Val Lys Val Glu Leu
    1055                1060                1065

CTG GAG GAG CGG AAC ACG GCT TTA GGT GTC ATC AGT AAC TGG ACA GAC     3685
Leu Glu Glu Arg Asn Thr Ala Leu Gly Val Ile Ser Asn Trp Thr Asp
```

```
1070                1075                1080                1085

GAG CTC CGC CTC CCG CCC TGC ACC ATC TTC CAG GCC TTC AAG TAC TAC    3733
Glu Leu Arg Leu Pro Pro Cys Thr Ile Phe Gln Ala Phe Lys Tyr Tyr
                1090                1095                1100

CTG GAC ATC ACC ACG CCA CCA ACG CCT CTG CAG CTG CAG CAG TTT GCC    3781
Leu Asp Ile Thr Thr Pro Pro Thr Pro Leu Gln Leu Gln Gln Phe Ala
                1105                1110                1115

TCC CTA GCT ACC AGC GAG AAG GAG AAG CAG CGT CTG CTG GTC CTC AGC    3829
Ser Leu Ala Thr Ser Glu Lys Glu Lys Gln Arg Leu Leu Val Leu Ser
                1120                1125                1130

AAG GGT TTG CAG GAG TAC GAG GAA TGG AAA TGG GGC AAG AAC CCC ACC    3877
Lys Gly Leu Gln Glu Tyr Glu Glu Trp Lys Trp Gly Lys Asn Pro Thr
        1135                1140                1145

ATC GTG GAG GTG CTG GAG GAG TTC CCA TCT ATC CAG ATG CCG GCC ACC    3925
Ile Val Glu Val Leu Glu Glu Phe Pro Ser Ile Gln Met Pro Ala Thr
1150                1155                1160                1165

CTG CTC CTG ACC CAG CTG TCC CTG CTG CAG CCC CGC TAC TAT TCC ATC    3973
Leu Leu Leu Thr Gln Leu Ser Leu Leu Gln Pro Arg Tyr Tyr Ser Ile
                1170                1175                1180

AGC TCC TCC CCA GAC ATG TAC CCT GAT GAA GTG CAC CTC ACT GTG GCC    4021
Ser Ser Ser Pro Asp Met Tyr Pro Asp Glu Val His Leu Thr Val Ala
                1185                1190                1195

ATC GTT TCC TAC CGC ACT CGA GAT GGA GAA GGA CCA ATT CAC CAC GGC    4069
Ile Val Ser Tyr Arg Thr Arg Asp Gly Glu Gly Pro Ile His His Gly
                1200                1205                1210

GTA TGC TCC TCC TGG CTC AAC CGG ATA CAG GCT GAC GAA CTG GTC CCC    4117
Val Cys Ser Ser Trp Leu Asn Arg Ile Gln Ala Asp Glu Leu Val Pro
        1215                1220                1225

TGT TTC GTG AGA GGA GCA CCC AGC TTC CAC CTG CCC CGG AAC CCC CAA    4165
Cys Phe Val Arg Gly Ala Pro Ser Phe His Leu Pro Arg Asn Pro Gln
1230                1235                1240                1245

GTC CCC TGC ATC CTC GTT GGA CCA GGC ACC GGC ATT GCC CCT TTC CGA    4213
Val Pro Cys Ile Leu Val Gly Pro Gly Thr Gly Ile Ala Pro Phe Arg
                1250                1255                1260

AGC TTC TGG CAA CAG CGG CAA TTT GAT ATC CAA CAC AAA GGA ATG AAC    4261
Ser Phe Trp Gln Gln Arg Gln Phe Asp Ile Gln His Lys Gly Met Asn
                1265                1270                1275

CCC TGC CCC ATG GTC CTG GTC TTC GGG TGC CGG CAA TCC AAG ATA GAT    4309
Pro Cys Pro Met Val Leu Val Phe Gly Cys Arg Gln Ser Lys Ile Asp
                1280                1285                1290

CAT ATC TAC AGG GAA GAG ACC CTG CAG GCC AAG AAC AAG GGG GTC TTC    4357
His Ile Tyr Arg Glu Glu Thr Leu Gln Ala Lys Asn Lys Gly Val Phe
                1295                1300                1305

AGA GAG CTG TAC ACG GCT TAC TCC CGG GAG CCA GAC AAA CCA AAG AAG    4405
Arg Glu Leu Tyr Thr Ala Tyr Ser Arg Glu Pro Asp Lys Pro Lys Lys
1310                1315                1320                1325

TAC GTG CAG GAC ATC CTG CAG GAG CAG CTG GCG GAG TCT GTG TAC CGA    4453
Tyr Val Gln Asp Ile Leu Gln Glu Gln Leu Ala Glu Ser Val Tyr Arg
                1330                1335                1340

GCC CTG AAG GAG CAA GGG GGC CAC ATA TAC GTC TGT GGG GAC GTC ACC    4501
Ala Leu Lys Glu Gln Gly Gly His Ile Tyr Val Cys Gly Asp Val Thr
        1345                1350                1355

ATG GCT GCT GAT GTC CTC AAA GCC ATC CAG CGC ATC ATG ACC CAG CAG    4549
Met Ala Ala Asp Val Leu Lys Ala Ile Gln Arg Ile Met Thr Gln Gln
                1360                1365                1370

GGG AAG CTC TCG GCA GAG GAC GCC GGC GTA TTC ATC AGC CGG ATG AGG    4597
Gly Lys Leu Ser Ala Glu Asp Ala Gly Val Phe Ile Ser Arg Met Arg
                1375                1380                1385

GAT GAC AAC CGA TAC CAT GAG GAT ATT TTT GGA GTC ACC CTG CGA ACG    4645
```

```
Asp Asp Asn Arg Tyr His Glu Asp Ile Phe Gly Val Thr Leu Arg Thr
1390                1395                1400                1405

ATC GAA GTG ACC AAC CGC CTT AGA TCT GAG TCC ATT GCC TTC ATT GAA    4693
Ile Glu Val Thr Asn Arg Leu Arg Ser Glu Ser Ile Ala Phe Ile Glu
            1410                1415                1420

GAG AGC AAA AAA GAC ACC GAT GAG GTT TTC AGC TCC TAACTGGACC         4739
Glu Ser Lys Lys Asp Thr Asp Glu Val Phe Ser Ser
            1425                1430

CTCTTGCCCA GCCGGCTGCA AGTTTGTAAG CGCGGGACAG A                      4780
```

(2) INFORMATION FOR SEQ ID NO:21:

(i) SEQUENCE CHARACTERISTICS:
        (A) LENGTH: 1433 amino acids
        (B) TYPE: amino acid
        (D) TOPOLOGY: linear (ii) MOLECULE TYPE: protein (xi) SEQUENCE DESCRIPTION: SEQ ID NO:21:

```
Met Glu Asp His Met Phe Gly Val Gln Gln Ile Gln Pro Asn Val Ile
 1               5                  10                  15

Ser Val Arg Leu Phe Lys Arg Lys Val Gly Gly Leu Gly Phe Leu Val
             20                  25                  30

Lys Glu Arg Val Ser Lys Pro Pro Val Ile Ile Ser Asp Leu Ile Arg
         35                  40                  45

Gly Gly Ala Ala Glu Gln Ser Gly Leu Ile Gln Ala Gly Asp Ile Ile
     50                  55                  60

Leu Ala Val Asn Gly Arg Pro Leu Val Asp Leu Ser Tyr Asp Ser Ala
 65                  70                  75                  80

Leu Glu Val Leu Arg Gly Ile Ala Ser Glu Thr His Val Val Leu Ile
                 85                  90                  95

Leu Arg Gly Pro Glu Gly Phe Thr Thr His Leu Glu Thr Thr Phe Thr
            100                 105                 110

Gly Asp Gly Thr Pro Lys Thr Ile Arg Val Thr Gln Pro Leu Gly Pro
        115                 120                 125

Pro Thr Lys Ala Val Asp Leu Ser His Gln Pro Pro Ala Gly Lys Glu
130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
                165                 170                 175

Gly Trp Pro Gln Ala Pro Arg Gln Asp Pro Ala Lys Lys Ala Thr Arg
            180                 185                 190

Val Ser Leu Gln Gly Arg Gly Glu Asn Asn Glu Leu Leu Lys Glu Ile
        195                 200                 205

Glu Pro Val Leu Ser Leu Leu Thr Ser Gly Ser Arg Gly Val Lys Gly
210                 215                 220

Gly Ala Pro Ala Lys Ala Glu Met Lys Asp Met Gly Ile Gln Val Asp
225                 230                 235                 240

Arg Asp Leu Asp Gly Lys Ser His Lys Pro Leu Pro Leu Gly Val Glu
                245                 250                 255

Asn Asp Arg Val Phe Asn Asp Leu Trp Gly Lys Gly Asn Val Pro Val
            260                 265                 270

Val Leu Asn Asn Pro Tyr Ser Glu Lys Glu Gln Pro Pro Thr Ser Gly
        275                 280                 285
```

-continued

```
Lys Gln Ser Pro Thr Lys Asn Gly Ser Pro Ser Lys Cys Pro Arg Phe
    290                 295                 300

Leu Lys Val Lys Asn Trp Glu Thr Glu Val Val Leu Thr Asp Thr Leu
305                 310                 315                 320

His Leu Lys Ser Thr Leu Glu Thr Gly Cys Thr Glu Tyr Ile Cys Met
                325                 330                 335

Gly Ser Ile Met His Pro Ser Gln His Ala Arg Arg Pro Glu Asp Val
            340                 345                 350

Arg Thr Lys Gly Gln Leu Phe Pro Leu Ala Lys Glu Phe Ile Asp Gln
        355                 360                 365

Tyr Tyr Ser Ser Ile Lys Arg Phe Gly Ser Lys Ala His Met Glu Arg
    370                 375                 380

Leu Glu Glu Val Asn Lys Glu Ile Asp Thr Thr Ser Thr Tyr Gln Leu
385                 390                 395                 400

Lys Asp Thr Glu Leu Ile Tyr Gly Ala Lys His Ala Trp Arg Asn Ala
                405                 410                 415

Ser Arg Cys Val Gly Arg Ile Gln Trp Ser Lys Leu Gln Val Phe Asp
            420                 425                 430

Ala Arg Asp Cys Thr Thr Ala His Gly Met Phe Asn Tyr Ile Cys Asn
        435                 440                 445

His Val Lys Tyr Ala Thr Asn Lys Gly Asn Leu Arg Ser Ala Ile Thr
    450                 455                 460

Ile Phe Pro Gln Arg Thr Asp Gly Lys His Asp Phe Arg Val Trp Asn
465                 470                 475                 480

Ser Gln Leu Ile Arg Tyr Ala Gly Tyr Lys His Arg Asp Gly Ser Thr
                485                 490                 495

Leu Gly Asp Pro Ala Asn Val Gln Phe Thr Glu Ile Cys Ile Gln Gln
            500                 505                 510

Gly Trp Lys Pro Pro Arg Gly Arg Phe Asp Val Leu Pro Leu Leu Leu
        515                 520                 525

Gln Ala Asn Gly Asn Asp Pro Glu Leu Phe Gln Ile Pro Pro Glu Leu
    530                 535                 540

Val Leu Glu Leu Pro Ile Arg His Pro Lys Phe Glu Trp Phe Lys Asp
545                 550                 555                 560

Leu Ala Leu Lys Trp Tyr Gly Leu Pro Ala Val Ser Asn Met Leu Leu
                565                 570                 575

Glu Ile Gly Gly Leu Glu Phe Ser Ala Cys Pro Phe Ser Gly Trp Tyr
            580                 585                 590

Met Gly Thr Glu Ile Gly Val Arg Asp Tyr Cys Asp Asn Ser Arg Tyr
        595                 600                 605

Asn Ile Leu Glu Glu Val Ala Lys Lys Met Asn Leu Asp Met Arg Lys
    610                 615                 620

Thr Ser Ser Leu Trp Lys Asp Gln Ala Leu Val Glu Ile Asn Ile Ala
625                 630                 635                 640

Val Leu Tyr Ser Phe Gln Ser Asp Lys Val Thr Ile Val Asp His His
                645                 650                 655

Ser Ala Thr Glu Ser Phe Ile Lys His Met Glu Asn Glu Tyr Arg Cys
            660                 665                 670

Arg Gly Gly Cys Pro Ala Asp Trp Val Trp Ile Val Pro Pro Met Ser
        675                 680                 685

Gly Ser Ile Thr Pro Val Phe His Gln Glu Met Leu Asn Tyr Arg Leu
    690                 695                 700

Thr Pro Ser Phe Glu Tyr Gln Pro Asp Pro Trp Asn Thr His Val Trp
```

-continued

```
                705                 710                 715                 720

Lys Gly Thr Asn Gly Thr Pro Thr Lys Arg Arg Ala Ile Gly Phe Lys
                725                 730                 735

Lys Leu Ala Glu Ala Val Lys Phe Ser Ala Lys Leu Met Gly Gln Ala
                740                 745                 750

Met Ala Lys Arg Val Lys Ala Thr Ile Leu Tyr Ala Thr Glu Thr Gly
                755                 760                 765

Lys Ser Gln Ala Tyr Ala Lys Thr Leu Cys Glu Ile Phe Lys His Ala
                770                 775                 780

Phe Asp Ala Lys Val Met Ser Met Glu Glu Tyr Asp Ile Val His Leu
785                 790                 795                 800

Glu His Glu Thr Leu Val Leu Val Val Thr Ser Thr Phe Gly Asn Gly
                805                 810                 815

Asp Pro Pro Glu Asn Gly Glu Lys Phe Gly Cys Ala Leu Met Glu Met
                820                 825                 830

Arg His Pro Asn Ser Val Gln Glu Glu Arg Lys Ser Tyr Lys Val Arg
                835                 840                 845

Phe Asn Ser Val Ser Ser Tyr Ser Asp Ser Gln Lys Ser Ser Gly Asp
                850                 855                 860

Gly Pro Asp Leu Arg Asp Asn Phe Glu Ser Ala Gly Pro Leu Ala Asn
865                 870                 875                 880

Val Arg Phe Ser Val Phe Gly Leu Gly Ser Arg Ala Tyr Pro His Phe
                885                 890                 895

Cys Ala Phe Gly His Ala Val Asp Thr Leu Leu Glu Glu Leu Gly Gly
                900                 905                 910

Glu Arg Ile Leu Lys Met Arg Glu Gly Asp Glu Leu Cys Gly Gln Glu
                915                 920                 925

Glu Ala Phe Arg Thr Trp Ala Lys Lys Val Phe Lys Ala Ala Cys Asp
                930                 935                 940

Val Phe Cys Val Gly Asp Asp Val Asn Ile Glu Lys Ala Asn Asn Ser
945                 950                 955                 960

Leu Ile Ser Asn Asp Arg Ser Trp Lys Arg Asn Lys Phe Arg Leu Thr
                965                 970                 975

Phe Val Ala Glu Ala Pro Glu Leu Thr Gln Gly Leu Ser Asn Val His
                980                 985                 990

Lys Lys Arg Val Ser Ala Ala Arg Leu Leu Ser Arg Gln Asn Leu Gln
                995                 1000                1005

Ser Pro Lys Ser Ser Arg Ser Thr Ile Phe Val Arg Leu His Thr Asn
                1010                1015                1020

Gly Ser Gln Glu Leu Gln Tyr Gln Pro Gly Asp His Leu Gly Val Phe
1025                1030                1035                1040

Pro Gly Asn His Glu Asp Leu Val Asn Ala Leu Ile Glu Arg Leu Glu
                1045                1050                1055

Asp Ala Pro Pro Val Asn Gln Met Val Lys Val Glu Leu Leu Glu Glu
                1060                1065                1070

Arg Asn Thr Ala Leu Gly Val Ile Ser Asn Trp Thr Asp Glu Leu Arg
                1075                1080                1085

Leu Pro Pro Cys Thr Ile Phe Gln Ala Phe Lys Tyr Tyr Leu Asp Ile
                1090                1095                1100

Thr Thr Pro Pro Thr Pro Leu Gln Leu Gln Gln Phe Ala Ser Leu Ala
1105                1110                1115                1120

Thr Ser Glu Lys Glu Lys Gln Arg Leu Leu Val Leu Ser Lys Gly Leu
                1125                1130                1135
```

-continued

```
Gln Glu Tyr Glu Glu Trp Lys Trp Gly Lys Asn Pro Thr Ile Val Glu
            1140                1145                1150

Val Leu Glu Glu Phe Pro Ser Ile Gln Met Pro Ala Thr Leu Leu Leu
            1155                1160                1165

Thr Gln Leu Ser Leu Leu Gln Pro Arg Tyr Tyr Ser Ile Ser Ser Ser
        1170                1175                1180

Pro Asp Met Tyr Pro Asp Glu Val His Leu Thr Val Ala Ile Val Ser
1185                1190                1195                1200

Tyr Arg Thr Arg Asp Gly Glu Gly Pro Ile His His Gly Val Cys Ser
            1205                1210                1215

Ser Trp Leu Asn Arg Ile Gln Ala Asp Glu Leu Val Pro Cys Phe Val
            1220                1225                1230

Arg Gly Ala Pro Ser Phe His Leu Pro Arg Asn Pro Gln Val Pro Cys
            1235                1240                1245

Ile Leu Val Gly Pro Gly Thr Gly Ile Ala Pro Phe Arg Ser Phe Trp
            1250                1255                1260

Gln Gln Arg Gln Phe Asp Ile Gln His Lys Gly Met Asn Pro Cys Pro
1265                1270                1275                1280

Met Val Leu Val Phe Gly Cys Arg Gln Ser Lys Ile Asp His Ile Tyr
            1285                1290                1295

Arg Glu Glu Thr Leu Gln Ala Lys Asn Lys Gly Val Phe Arg Glu Leu
            1300                1305                1310

Tyr Thr Ala Tyr Ser Arg Glu Pro Asp Lys Pro Lys Lys Tyr Val Gln
            1315                1320                1325

Asp Ile Leu Gln Glu Gln Leu Ala Glu Ser Val Tyr Arg Ala Leu Lys
    1330                1335                1340

Glu Gln Gly Gly His Ile Tyr Val Cys Gly Asp Val Thr Met Ala Ala
1345                1350                1355                1360

Asp Val Leu Lys Ala Ile Gln Arg Ile Met Thr Gln Gln Gly Lys Leu
            1365                1370                1375

Ser Ala Glu Asp Ala Gly Val Phe Ile Ser Arg Met Arg Asp Asp Asn
            1380                1385                1390

Arg Tyr His Glu Asp Ile Phe Gly Val Thr Leu Arg Thr Ile Glu Val
            1395                1400                1405

Thr Asn Arg Leu Arg Ser Glu Ser Ile Ala Phe Ile Glu Glu Ser Lys
    1410                1415                1420

Lys Asp Thr Asp Glu Val Phe Ser Ser
1425                1430
```

(2) INFORMATION FOR SEQ ID NO:22:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: EPO-1 HRE element (xi) SEQUENCE DESCRIPTION: SEQ ID NO:22:

```
GAACTGAAAC CACCAATATG ACTCTTGGCT TTTCTGTTTT CTGGGAACCT CCAAATCCCC      60
```

```
TGGCTCTGTC CCACTCCTGG CAGCAGTGCA GCAGGTCCAG GTCCGGGAAA TGAGGGGTGG         120

AGGGGGCTGG GCCCTACGTG CTGTCTCACA CAGCCTGTCT GACCTCTCGA CCTACCGGCC         180

TAGGCCACAA GCTCTGCCTA CGCTGGTCAA TAAGGTGTCT CCATTCAAGG CCTCACCGCA         240

GTAAGGCAGC TGCCAA                                                         256
```

(2) INFORMATION FOR SEQ ID NO:23:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 42 bp EPO 3' hypoxia response
            enhancer element (Madan, et al, PNAS 90:3928, 1993)

(xi) SEQUENCE DESCRIPTION: SEQ ID NO:23:

```
GGGCCCTACG TGCTGTCTCA CACAGCCTGT CTGACCTCTC GA                            42
```

(2) INFORMATION FOR SEQ ID NO:24:

(i) SEQUENCE CHARACTERISTICS:
        (A) LENGTH: 86 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: 86 nucleotide fragment from
            'MHC promoter (xi) SEQUENCE DESCRIPTION: SEQ ID NO:24:

```
GTCCCAGCAG ATGACTCCAA ATTTAGGCAG CAGGCACGTG GAATGAGCTA TAAAGGGGCT         60

GGAGCGCTGA GAGCTGTCAG ACCGAG                                              86
```

(2) INFORMATION FOR SEQ ID NO:25:

(i) SEQUENCE CHARACTERISTICS:
        (A) LENGTH: 2423 base pairs
        (B) TYPE: nucleic acid
        (C) STRANDEDNESS: double
        (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: mouse catalase gene GenBank #L25069

(ix) FEATURE:
        (A) NAME/KEY: CDS
        (B) LOCATION: 88..1671

(xi) SEQUENCE DESCRIPTION: SEQ ID NO:25:

```
ATTGCCTTCT CCGGGTGGAG ACCAGACCGC TGCGTCCGTC CCTGCTGTCT CACGTTCCGC      60

AGCTCTGCAG CTCCGCAATC CTACACC ATG TCG GAC AGT CGG GAC CCA GCC         111
                              Met Ser Asp Ser Arg Asp Pro Ala
                               1               5

AGC GAC CAG ATG AAG CAG TGG AAG GAG CAG CGG GCC TCG CAG AGA CCT       159
Ser Asp Gln Met Lys Gln Trp Lys Glu Gln Arg Ala Ser Gln Arg Pro
 10              15                  20

GAT GTC CTG ACC ACC GGA GGC GGG AAC CCA ATA GGA GAT AAA CTT AAT       207
Asp Val Leu Thr Thr Gly Gly Gly Asn Pro Ile Gly Asp Lys Leu Asn
 25              30                  35                  40

ATC ATG ACC GCG GGG TCC CGA GGG CCC CTC CTC GTT CAG GAT GTG GTT       255
Ile Met Thr Ala Gly Ser Arg Gly Pro Leu Leu Val Gln Asp Val Val
                 45                  50                  55

TTC ACT GAC GAG ATG GCA CAC TTT GAC AGA GAG CGG ATT CCT GAG AGA       303
Phe Thr Asp Glu Met Ala His Phe Asp Arg Glu Arg Ile Pro Glu Arg
             60                  65                  70

GTG GTA CAC GCA AAA GGA GCA GGT GCT TTT GGA TAC TTT GAG GTC ACC       351
Val Val His Ala Lys Gly Ala Gly Ala Phe Gly Tyr Phe Glu Val Thr
         75                  80                  85

CAC GAT ATC ACC AGA TAC TCC AAG GGA AAG GTG TTT GAG CAT ATT GGA       399
His Asp Ile Thr Arg Tyr Ser Lys Gly Lys Val Phe Glu His Ile Gly
     90                  95                 100

AAG AGG ACC CCT ATT GCC GTT CGG TTC TCC ACA GTC GCT GGA GAG TCA       447
Lys Arg Thr Pro Ile Ala Val Arg Phe Ser Thr Val Ala Gly Glu Ser
105                 110                 115                 120

GGC TCA GCT GAC ACA GTT CGT GAC CCT CGG GGG TTT GCA GTG AAA TTT       495
Gly Ser Ala Asp Thr Val Arg Asp Pro Arg Gly Phe Ala Val Lys Phe
                125                 130                 135

TAC ACT GAA GAT GGT AAC TGG GAT CTT GTG GGA AAC AAC ACC CCT ATT       543
Tyr Thr Glu Asp Gly Asn Trp Asp Leu Val Gly Asn Asn Thr Pro Ile
            140                 145                 150

TTC TTC ATC AGG GAT GCC ATA TTG TTT CCA TCC TTT ATC CAT AGC CAG       591
Phe Phe Ile Arg Asp Ala Ile Leu Phe Pro Ser Phe Ile His Ser Gln
        155                 160                 165

AAG AGA AAC CCA CAG ACT CAC CTG AAG GAT CCT GAC ATG GTC TGG GAC       639
Lys Arg Asn Pro Gln Thr His Leu Lys Asp Pro Asp Met Val Trp Asp
    170                 175                 180

TTC TGG AGT CTT CGT CCC GAG TCT CTC CAT CAG GTT TCT TTC TTG TTC       687
Phe Trp Ser Leu Arg Pro Glu Ser Leu His Gln Val Ser Phe Leu Phe
185                 190                 195                 200

AGT GAC CGA GGG ATT CCC GAT GGT CAC CGG CAC ATG AAT GGC TAT GGA       735
Ser Asp Arg Gly Ile Pro Asp Gly His Arg His Met Asn Gly Tyr Gly
                205                 210                 215

TCA CAC ACC TTC AAG TTG GTT AAT GCA GAT GGA GAG GCA GTC TAT TGC       783
Ser His Thr Phe Lys Leu Val Asn Ala Asp Gly Glu Ala Val Tyr Cys
            220                 225                 230

AAG TTC CAT TAC AAG ACC GAC CAG GGC ATC AAA AAC TTG CCT GTT GGA       831
Lys Phe His Tyr Lys Thr Asp Gln Gly Ile Lys Asn Leu Pro Val Gly
        235                 240                 245

GAG GCA GGA AGG CTT GCT CAG GAA GAT CCG GAT TAT GGC CTC CGA GAT       879
Glu Ala Gly Arg Leu Ala Gln Glu Asp Pro Asp Tyr Gly Leu Arg Asp
    250                 255                 260

CTT TTC AAT GCC ATC GCC AAT GGC AAT TAC CCG TCC TGG ACG TTT TAC       927
Leu Phe Asn Ala Ile Ala Asn Gly Asn Tyr Pro Ser Trp Thr Phe Tyr
265                 270                 275                 280

ATC CAG GTC ATG ACT TTT AAG GAG GCA GAA ACT TTC CCA TTT AAT CCA       975
Ile Gln Val Met Thr Phe Lys Glu Ala Glu Thr Phe Pro Phe Asn Pro
                285                 290                 295
```

```
TTT GAT CTG ACC AAG GTT TGG CCT CAC AAG GAC TAC CCT CTT ATA CCA      1023
Phe Asp Leu Thr Lys Val Trp Pro His Lys Asp Tyr Pro Leu Ile Pro
            300                 305                 310

GTT GGC AAA GTG GTT TTA AAC AAA AAT CCA GTT AAT TAC TTT GCT GAA      1071
Val Gly Lys Val Val Leu Asn Lys Asn Pro Val Asn Tyr Phe Ala Glu
                315                 320                 325

GTT GAA CAG ATG GCT TTT GAC CCA AGC AAT ATG CCC CCT GGC ATC GAG      1119
Val Glu Gln Met Ala Phe Asp Pro Ser Asn Met Pro Pro Gly Ile Glu
        330                 335                 340

CCC AGC CCT GAC AAA AAG CTT CAG GGC CGC CTT TTT GCC TAC CCG GAC      1167
Pro Ser Pro Asp Lys Lys Leu Gln Gly Arg Leu Phe Ala Tyr Pro Asp
345                 350                 355                 360

ACT CAC CGC CAC CGC CTG GGA CCC AAC TAT CTG CAG ATA CCT GTG AAC      1215
Thr His Arg His Arg Leu Gly Pro Asn Tyr Leu Gln Ile Pro Val Asn
                365                 370                 375

TGT CCC TAC CGC GCT CGA GTG GCC AAC TAC CAG CGT GAT GGC CCC ATG      1263
Cys Pro Tyr Arg Ala Arg Val Ala Asn Tyr Gln Arg Asp Gly Pro Met
            380                 385                 390

TGC ATG CAT GAC AAC CAG GGT GGT GCC CCC AAC TAT TAC CCC AAC AGC      1311
Cys Met His Asp Asn Gln Gly Gly Ala Pro Asn Tyr Tyr Pro Asn Ser
                395                 400                 405

TTC AGC GCA CCA GAG CAG CAG CGC TCA GCC CTG GAG CAC AGC GTC CAG      1359
Phe Ser Ala Pro Glu Gln Gln Arg Ser Ala Leu Glu His Ser Val Gln
        410                 415                 420

TGC GCT GTA GAT GTG AAA CGC TTC AAC AGT GCT AAT GAA GAC AAT GTC      1407
Cys Ala Val Asp Val Lys Arg Phe Asn Ser Ala Asn Glu Asp Asn Val
425                 430                 435                 440

ACT CAG GTG CGG ACA TTC TAC ACA AAG GTG TTG AAT GAG GAG GAG AGG      1455
Thr Gln Val Arg Thr Phe Tyr Thr Lys Val Leu Asn Glu Glu Glu Arg
                445                 450                 455

AAA CGC CTG TGT GAG AAC ATT GCC GGC CAC CTG AAG GAC GCT CAG CTT      1503
Lys Arg Leu Cys Glu Asn Ile Ala Gly His Leu Lys Asp Ala Gln Leu
            460                 465                 470

TTC ATT CAG AAG AAA GCG GTC AAG AAT TTC ACT GAC GTC CAC CCT GAC      1551
Phe Ile Gln Lys Lys Ala Val Lys Asn Phe Thr Asp Val His Pro Asp
        475                 480                 485

TAT GGG GCC CGC ATC CAG GCT CTT CTG GAC AAG TAC AAC GCT GAG AAG      1599
Tyr Gly Ala Arg Ile Gln Ala Leu Leu Asp Lys Tyr Asn Ala Glu Lys
490                 495                 500

CCT AAG AAC GCA ATT CAC ACC TAC ACG CAG GCC GGC TCT CAC ATG GCT      1647
Pro Lys Asn Ala Ile His Thr Tyr Thr Gln Ala Gly Ser His Met Ala
505                 510                 515                 520

GCG AAG GGA AAA GCT AAC CTG TAACTCCGGT GCTCAGCCTC CGCTGAGGAG         1698
Ala Lys Gly Lys Ala Asn Leu
                525

ACCTCTCGTG AAGCCGAGCC TGAGGATCAC CTGTAATCAA CGCTGGATGG ATTCTCCCCC    1758

GCCGGAGCGC AGACTCACGC TGATGACTTT AAAACGATAA TCCGGGCTTC TAGAGTGAAT    1818

GATAACCATG CTTTTGATGC CGTTTCCTGA AGGGAAATGA AAGGTTAGGG CTTAGCAATC    1878

ATTTAACAGA AACATGGATC TAATAGGACT TCTGTTTGGA TTATTCATTT AAATGACTAC    1938

ATTTAAAATG ATTACAAGAA AGGTGTTCTA GCCAGAAACA TGACTTGATT AGACAAGATA    1998

AAAATCTTGG CGAGAATAGT GTATTCTCCT ATTACCTCAT GGTCTGGTAT ATATACAATA    2058

CAACACACAT ACCACACACA CACACACATG CAATACACAC ACTACACACA CATACACACA    2118

CTCACACACA CTCATACACA CACATGAAGA GATGATAAAG ATGGCCCACT CAGAATTTTT    2178

TTTTTATTTT TCTAAGGTCC TTATAAGCAA AACCATACTT GCATCATGTC TTCCAAAAGT    2238
```

```
AACTTTAGCA CTGTTGAAAC TTAATGTTTA TTCCTGTGCT GTGCGGTGCT GTGCTGTGCT    2298

GTGCTGTGCA GCTAATCAGA TTCTTGTTTT TTCCCACTTG GATTATGTTG ATGCTAATAC    2358

GCAGTGATTT CACATAGGAT GATTTGTACT TGCTTACATT TTTACAATAA AATGATCTAC    2418

ATGGA                                                                 2423
```

(2) INFORMATION FOR SEQ ID NO:26:

(i) SEQUENCE CHARACTERISTICS:
        (A) LENGTH: 527 amino acids
        (B) TYPE: amino acid
        (D) TOPOLOGY: linear (ii) MOLECULE TYPE: protein (xi) SEQUENCE DESCRIPTION: SEQ ID NO:26:

```
Met Ser Asp Ser Arg Asp Pro Ala Ser Asp Gln Met Lys Gln Trp Lys
 1               5                  10                  15

Glu Gln Arg Ala Ser Gln Arg Pro Asp Val Leu Thr Thr Gly Gly Gly
                20                  25                  30

Asn Pro Ile Gly Asp Lys Leu Asn Ile Met Thr Ala Gly Ser Arg Gly
            35                  40                  45

Pro Leu Leu Val Gln Asp Val Val Phe Thr Asp Glu Met Ala His Phe
        50                  55                  60

Asp Arg Glu Arg Ile Pro Glu Arg Val Val His Ala Lys Gly Ala Gly
65                  70                  75                  80

Ala Phe Gly Tyr Phe Glu Val Thr His Asp Ile Thr Arg Tyr Ser Lys
                85                  90                  95

Gly Lys Val Phe Glu His Ile Gly Lys Arg Thr Pro Ile Ala Val Arg
            100                 105                 110

Phe Ser Thr Val Ala Gly Glu Ser Gly Ser Ala Asp Thr Val Arg Asp
        115                 120                 125

Pro Arg Gly Phe Ala Val Lys Phe Tyr Thr Glu Asp Gly Asn Trp Asp
    130                 135                 140

Leu Val Gly Asn Asn Thr Pro Ile Phe Phe Ile Arg Asp Ala Ile Leu
145                 150                 155                 160

Phe Pro Ser Phe Ile His Ser Gln Lys Arg Asn Pro Gln Thr His Leu
                165                 170                 175

Lys Asp Pro Asp Met Val Trp Asp Phe Trp Ser Leu Arg Pro Glu Ser
            180                 185                 190

Leu His Gln Val Ser Phe Leu Phe Ser Asp Arg Gly Ile Pro Asp Gly
        195                 200                 205

His Arg His Met Asn Gly Tyr Gly Ser His Thr Phe Lys Leu Val Asn
    210                 215                 220

Ala Asp Gly Glu Ala Val Tyr Cys Lys Phe His Tyr Lys Thr Asp Gln
225                 230                 235                 240

Gly Ile Lys Asn Leu Pro Val Gly Glu Ala Gly Arg Leu Ala Gln Glu
                245                 250                 255

Asp Pro Asp Tyr Gly Leu Arg Asp Leu Phe Asn Ala Ile Ala Asn Gly
            260                 265                 270

Asn Tyr Pro Ser Trp Thr Phe Tyr Ile Gln Val Met Thr Phe Lys Glu
        275                 280                 285

Ala Glu Thr Phe Pro Phe Asn Pro Phe Asp Leu Thr Lys Val Trp Pro
    290                 295                 300

His Lys Asp Tyr Pro Leu Ile Pro Val Gly Lys Val Val Leu Asn Lys
305                 310                 315                 320
```

-continued

```
Asn Pro Val Asn Tyr Phe Ala Glu Val Glu Gln Met Ala Phe Asp Pro
            325                 330                 335

Ser Asn Met Pro Pro Gly Ile Glu Pro Ser Pro Asp Lys Lys Leu Gln
        340                 345                 350

Gly Arg Leu Phe Ala Tyr Pro Asp Thr His Arg His Arg Leu Gly Pro
        355                 360                 365

Asn Tyr Leu Gln Ile Pro Val Asn Cys Pro Tyr Arg Ala Arg Val Ala
        370                 375                 380

Asn Tyr Gln Arg Asp Gly Pro Met Cys Met His Asp Asn Gln Gly Gly
385                 390                 395                 400

Ala Pro Asn Tyr Tyr Pro Asn Ser Phe Ser Ala Pro Glu Gln Gln Arg
            405                 410                 415

Ser Ala Leu Glu His Ser Val Gln Cys Ala Val Asp Val Lys Arg Phe
            420                 425                 430

Asn Ser Ala Asn Glu Asp Asn Val Thr Gln Val Arg Thr Phe Tyr Thr
            435                 440                 445

Lys Val Leu Asn Glu Glu Glu Arg Lys Arg Leu Cys Glu Asn Ile Ala
        450                 455                 460

Gly His Leu Lys Asp Ala Gln Leu Phe Ile Gln Lys Lys Ala Val Lys
465                 470                 475                 480

Asn Phe Thr Asp Val His Pro Asp Tyr Gly Ala Arg Ile Gln Ala Leu
            485                 490                 495

Leu Asp Lys Tyr Asn Ala Glu Lys Pro Lys Asn Ala Ile His Thr Tyr
            500                 505                 510

Thr Gln Ala Gly Ser His Met Ala Ala Lys Gly Lys Ala Asn Leu
            515                 520                 525
```

(2) INFORMATION FOR SEQ ID NO:27:

(i) SEQUENCE CHARACTERISTICS:
        (A) LENGTH: 969 base pairs
        (B) TYPE: nucleic acid
        (C) STRANDEDNESS: double
        (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
        (C) INDIVIDUAL ISOLATE: human manganese superoxide dismutase
           EMBL #X59445

(ix) FEATURE:
        (A) NAME/KEY: CDS
        (B) LOCATION: 61..729

(xi) SEQUENCE DESCRIPTION: SEQ ID NO:27:

```
TGGCTTCGGC AGCGGCTTCA GCAGATCGGC GGCATCAGCG GTAGCACCAG CACTAGCAGC      60

ATG TTG AGC CGG GCA GTG TGC GGC ACC AGC AGG CAG CTG GCT CCG GCT     108
Met Leu Ser Arg Ala Val Cys Gly Thr Ser Arg Gln Leu Ala Pro Ala
  1               5                  10                  15

TTG GGG TAT CTG GGC TCC AGG CAG AAG CAC AGC CTC CCC GAC CTG CCC     156
Leu Gly Tyr Leu Gly Ser Arg Gln Lys His Ser Leu Pro Asp Leu Pro
            20                  25                  30

TAC GAC TAC GGC GCC CTG GAA CCT CAC ATC AAC GCG CAG ATC ATG CAG     204
Tyr Asp Tyr Gly Ala Leu Glu Pro His Ile Asn Ala Gln Ile Met Gln
        35                  40                  45
```

```
CTG CAC CAC AGC AAG CAC CAC GCG GCC TAC GTG AAC AAC CTG AAC GTC      252
Leu His His Ser Lys His His Ala Ala Tyr Val Asn Asn Leu Asn Val
    50                  55                  60

AAC GAG GAG AAG TAC CAG GAG GCG TTG GCC AAG GGA GAT GTT ACA GCC      300
Asn Glu Glu Lys Tyr Gln Glu Ala Leu Ala Lys Gly Asp Val Thr Ala
65                  70                  75                  80

CAG ATA GCT CTT CAG CCT GCA CTG AAG TTC AAT GGT GGT GGT CAT ATC      348
Gln Ile Ala Leu Gln Pro Ala Leu Lys Phe Asn Gly Gly Gly His Ile
                85                  90                  95

AAT CAT AGC ATT TTC TGG ACA AAC CTC AGC CCT AAC GGT GGT GGA GAA      396
Asn His Ser Ile Phe Trp Thr Asn Leu Ser Pro Asn Gly Gly Gly Glu
            100                 105                 110

CCC AAA GGG GAG TTG CTG GAA GCC ATC AAA CGT GAC TTT GGT TCC TTT      444
Pro Lys Gly Glu Leu Leu Glu Ala Ile Lys Arg Asp Phe Gly Ser Phe
        115                 120                 125

GAC AAG TTT AAG GAG AAG CTG ACG GCT GCA TCT GTT GGT GTC CAA GGC      492
Asp Lys Phe Lys Glu Lys Leu Thr Ala Ala Ser Val Gly Val Gln Gly
130                 135                 140

TCA GGT TGG GGT TGG CTT GGT TTC AAT AAG GAA CGG GGA CAC TTA CAA      540
Ser Gly Trp Gly Trp Leu Gly Phe Asn Lys Glu Arg Gly His Leu Gln
145                 150                 155                 160

ATT GCT GCT TGT CCA AAT CAG GAT CCA CTG CAA GGA ACA ACA GGC CTT      588
Ile Ala Ala Cys Pro Asn Gln Asp Pro Leu Gln Gly Thr Thr Gly Leu
                165                 170                 175

ATT CCA CTG CTG GGG ATT GAT GTG TGG GAG CAC GCT TAC TAC CTT CAG      636
Ile Pro Leu Leu Gly Ile Asp Val Trp Glu His Ala Tyr Tyr Leu Gln
            180                 185                 190

TAT AAA AAT GTC AGG CCT GAT TAT CTA AAA GCT ATT TGG AAT GTA ATC      684
Tyr Lys Asn Val Arg Pro Asp Tyr Leu Lys Ala Ile Trp Asn Val Ile
        195                 200                 205

AAC TGG GAG AAT GTA ACT GAA AGA TAC ATG GCT TGC AAA AAG TAAACCACGA  736
Asn Trp Glu Asn Val Thr Glu Arg Tyr Met Ala Cys Lys Lys
210                 215                 220

TCGTTATGCT GAGTATGTTA AGCTCTTTAT GACTGTTTTT GTAGTGGTAT AGAGTACTGC   796

AGAATACAGT AAGCTGCTCT ATTGTAGCAT TTCTTGATGT TGCTTAGTCA CTTATTTCAT   856

AAACAACTTA ATGTTCTGAA TAATTTCTTA CTAAACATTT TGTTATTGGG CAAGTGATTG   916

AAAATAGTAA ATGCTTTGTG TGATTGAAAA AAAAAAAAA AAAAAAAAA AAA            969
```

(2) INFORMATION FOR SEQ ID NO:28:

(i) SEQUENCE CHARACTERISTICS:
        (A) LENGTH: 222 amino acids
        (B) TYPE: amino acid
        (D) TOPOLOGY: linear (ii) MOLECULE TYPE: protein (xi) SEQUENCE DESCRIPTION: SEQ ID NO:28:

```
Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Asn Glu Glu Lys Tyr Gln Glu Ala Leu Ala Lys Gly Asp Val Thr Ala
65                  70                  75                  80
```

```
Gln Ile Ala Leu Gln Pro Ala Leu Lys Phe Asn Gly Gly His Ile
                85                  90                  95

Asn His Ser Ile Phe Trp Thr Asn Leu Ser Pro Asn Gly Gly Glu
                100                 105                 110

Pro Lys Gly Glu Leu Leu Glu Ala Ile Lys Arg Asp Phe Gly Ser Phe
            115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
                180                 185                 190

Tyr Lys Asn Val Arg Pro Asp Tyr Leu Lys Ala Ile Trp Asn Val Ile
            195                 200                 205

Asn Trp Glu Asn Val Thr Glu Arg Tyr Met Ala Cys Lys Lys
    210                 215                 220

(2) INFORMATION FOR SEQ ID NO:29:

(i) SEQUENCE CHARACTERISTICS:
        (A) LENGTH: 691 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: human enolase gene (EMBL #X56832)
            fragment containinig nucleotides -628 to +63

(ix) FEATURE:
        (A) NAME/KEY: CDS
        (B) LOCATION: 629..691

(xi) SEQUENCE DESCRIPTION: SEQ ID NO:29:

CCTGGGGGTG GAGGTAGTAA AGGGTGAGCA TGGTATTGGC TTGGAGGAAG TGGGGGACAT    60

TTCTGCTTTT TTTCCTCCTG GGACTGGAGA TGCTTGAAAA AGCTGGGGGA AGGGGCGGCT   120

GGAGCAAGCA GATGGGACAA ACTCTGGGAA CACCGAAGGA TCTAGGGAAA GGAGGCTGTG   180

AGGAGGGCAG CAGGGATGGA TAGAAAAGGG CAGCTAGAGC TGGAACCTGA TAGGGAATTG   240

GGGGCCCAAG GAGATTTCGG AGCAGGAAAA TGAGAACCAG AAAGGATTTG AAGGCCACCA   300

GCCATGGAGA ACAGACTGCT TGACCAGAGG GGTGGAAGGA GAAGGCCTAA GTGGAGGCTT   360

GGGGGAGGTG GGGGCTTGGT GAGCGGTGGC ATCCCAGGAG CTATAGATAA GAGGCCCCTG   420

GATTCTTAGG ATGGGAGGGT GGAATAAGAG CTGTTCTGAG TGGGGAGGG GGCTGCGCCT    480

GCCTCTTTGG TCTGTGACCT TTTTGTAGGG TATTTTTAGC TCCAGCACCT GCCTTCTTGG   540

AGTGGGGAAG AATCTTAAAG GGCAAGGGAT TTCTGGTTCC TTAAGAGATC AACTGTCTAC   600

ACTCACTCAC ACCTCCTGTC CTGCAGCC ATG GCC ATG CAG AAA ATC TTT GCC      652
                              Met Ala Met Gln Lys Ile Phe Ala
                                1               5

CGG GAA ATC TTG GAC TCC AGG GGC AAC CCC ACG GTG GAG                 691
Arg Glu Ile Leu Asp Ser Arg Gly Asn Pro Thr Val Glu
    10                  15                  20
```

(2) INFORMATION FOR SEQ ID NO:30:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:30:

```
Met Ala Met Gln Lys Ile Phe Ala Arg Glu Ile Leu Asp Ser Arg Gly
 1               5                  10                  15

Asn Pro Thr Val Glu
            20
```

(2) INFORMATION FOR SEQ ID NO:31:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PKM/ENO3 consensus sequence (xi) SEQUENCE DESCRIPTION: SEQ ID NO:31:

```
GAGAGGCGGG CTNNCTG                                              17
```

(2) INFORMATION FOR SEQ ID NO:32:

(i) SEQUENCE CHARACTERISTICS:
        (A) LENGTH: 786 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: -760 MTAIIa promoter fragment (xi) SEQUENCE DESCRIPTION: SEQ ID NO:32:

```
AAGCTTGTGG CTTCTTCTCC TTACTCTTCC TCCTTGGTGT CTCTATGTTA GAGGGCCGTT    60

AGCATCTGCT GGGGCCTGGT CGCATTCACC CTGCTCTGCC ACTCACTGGC TGTGTGACTC   120

TGGACAAATT AACTTCTCTG GACCTGGCAG TTTCTCCTCT CTACAATGAG AATACTGGAG   180

AGTCCTTATC TTATGGGTTG CTACAGAATT AAGTGACATC TCACACACAA CACACTTCCT   240

ACAGTCCCTG TTACACGCTA AAAGTACTCA ACTAGCTTCG GATACGTCAT CAGCAACCAC   300

CCCACGGGTT ACTGTGATGC TGCACAATTA TTAAGCCCTG GCTGCTACAG AGTTGTAACC   360

TGTCTGCACT TCCAACCGGC GCCGCAAGCA GCATTCCCAG TCCCGCTTTC ACCCGCGCGC   420

TAACGGCTCA GGTTCGAGTA CAGGACAGGA GGGAGGGGAG CTGTGCACAC GGCGGAGGCG   480

CACGGCGTGG GCACCCAGCA CCCGGTACAC TGTGTCCTCC CGCTGCACCC AGCCCCTTCA   540
```

```
GCCCGAGGCG TCCCCGAGGC GCAAGTGGGC CGCCTTCAGG GAACTGACCG CCCGCGGCCC      600

GTGTGCAGAG CCGGGTGCGC CCGGCCCAGT GCGCGCGGCC GGGTGTTTCG CTTGGAGCCG      660

CAAGTGACTT CTAGCGCGGG GCGTGTGCAG GCACGGCCGG GGCGGGGCTT TTGCACTCGT      720

CCCGGCTCTT TCTAGCTATA AACACTGCTT GCCGCGCTGC ACTCCACCAC GCCTCCTCCA      780

AGTCCC                                                                786

(2) INFORMATION FOR SEQ ID NO:33:

(i) SEQUENCE CHARACTERISTICS:
        (A) LENGTH: 366 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: -345 MTAIIa promoter fragment (xi) SEQUENCE DESCRIPTION: SEQ ID NO:33:

TAACGGCTCA GGTTCGAGTA CAGGACAGGA GGGAGGGGAG CTGTGCACAC GGCGGAGGCG       60

CACGGCGTGG GCACCCAGCA CCCGGTACAC TGTGTCCTCC CGCTGCACCC AGCCCCTTCA      120

GCCCGAGGCG TCCCCGAGGC GCAAGTGGGC CGCCTTCAGG GAACTGACCG CCCGCGGCCC      180

GTGTGCAGAG CCGGGTGCGC CCGGCCCAGT GCGCGCGGCC GGGTGTTTCG CTTGGAGCCG      240

CAAGTGACTT CTAGCGCGGG GCGTGTGCAG GCACGGCCGG GGCGGGGCTT TTGCACTCGT      300

CCCGGCTCTT TCTAGCTATA AACACTGCTT GCCGCGCTGC ACTCCACCAC GCCTCCTCCA      360

AGTCCC                                                                366

(2) INFORMATION FOR SEQ ID NO:34:

(i) SEQUENCE CHARACTERISTICS:
        (A) LENGTH: 184 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: -163 MTAIIa promoter fragment (xi) SEQUENCE DESCRIPTION: SEQ ID NO:34:

GTGCAGAGCC GGGTGCGCCC GGCCCAGTGC GCGCGGCCGG GTGTTTCGCT TGGAGCCGCA       60

AGTGACTTCT AGCGCGGGGC GTGTGCAGGC ACGGCCGGGG CGGGGCTTTT GCACTCGTCC      120

CGGCTCTTTC TAGCTATAAA CACTGCTTGC CGCGCTGCAC TCCACCACGC CTCCTCCAAG      180

TCCC                                                                  184

(2) INFORMATION FOR SEQ ID NO:35:

(i) SEQUENCE CHARACTERISTICS:
        (A) LENGTH: 111 base pairs
        (B) TYPE: nucleic acid
        (C) STRANDEDNESS: double
```

(D) TOPOLOGY: unknown (ii) MOLECULE TYPE: DNA (genomic)

(iii) HYPOTHETICAL: NO (iv) ANTI-SENSE: NO (vi) ORIGINAL SOURCE:
             (C) INDIVIDUAL ISOLATE: -90 MTAIIa promoter fragment (xi) SEQUENCE DESCRIPTION: SEQ ID NO:35:

```
GCGGGGCGTG TGCAGGCACG GCCGGGGCGG GGCTTTTGCA CTCGTCCCGG CTCTTTCTAG      60

CTATAAACAC TGCTTGCCGC GCTGCACTCC ACCACGCCTC CTCCAAGTCC C              111
```

(2) INFORMATION FOR SEQ ID NO:36:

(i) SEQUENCE CHARACTERISTICS:
            (A) LENGTH: 1643 base pairs
            (B) TYPE: nucleic acid
            (C) STRANDEDNESS: double
            (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
            (C) INDIVIDUAL ISOLATE: TNF cDNA HSTNFR (EMBL Accession
                #X01394)

(ix) FEATURE:
            (A) NAME/KEY: CDS
            (B) LOCATION: 153..851

(xi) SEQUENCE DESCRIPTION: SEQ ID NO:36:

```
GCAGAGGACC AGCTAAGAGG GAGAGAAGCA ACTACAGACC CCCCCTGAAA ACAACCCTCA       60

GACGCCACAT CCCCTGACAA GCTGCCAGGC AGGTTCTCTT CCTCTCACAT ACTGACCCAC      120

GGCTCCACCC TCTCTCCCCT GGAAAGGACA CC ATG AGC ACT GAA AGC ATG ATC        173
                                   Met Ser Thr Glu Ser Met Ile
                                    1               5

CGG GAC GTG GAG CTG GCC GAG GAG GCG CTC CCC AAG AAG ACA GGG GGG        221
Arg Asp Val Glu Leu Ala Glu Glu Ala Leu Pro Lys Lys Thr Gly Gly
         10              15                  20

CCC CAG GGC TCC AGG CGG TGC TTG TTC CTC AGC CTC TTC TCC TTC CTG        269
Pro Gln Gly Ser Arg Arg Cys Leu Phe Leu Ser Leu Phe Ser Phe Leu
     25                  30                  35

ATC GTG GCA GGC GCC ACC ACG CTC TTC TGC CTG CTG CAC TTT GGA GTG        317
Ile Val Ala Gly Ala Thr Thr Leu Phe Cys Leu Leu His Phe Gly Val
 40                  45                  50                  55

ATC GGC CCC CAG AGG GAA GAG TTC CCC AGG GAC CTC TCT CTA ATC AGC        365
Ile Gly Pro Gln Arg Glu Glu Phe Pro Arg Asp Leu Ser Leu Ile Ser
                 60                  65                  70

CCT CTG GCC CAG GCA GTC AGA TCA TCT TCT CGA ACC CCG AGT GAC AAG        413
Pro Leu Ala Gln Ala Val Arg Ser Ser Ser Arg Thr Pro Ser Asp Lys
             75                  80                  85

CCT GTA GCC CAT GTT GTA GCA AAC CCT CAA GCT GAG GGG CAG CTC CAG        461
Pro Val Ala His Val Val Ala Asn Pro Gln Ala Glu Gly Gln Leu Gln
         90                  95                 100

TGG CTG AAC CGC CGG GCC AAT GCC CTC CTG GCC AAT GGC GTG GAG CTG        509
Trp Leu Asn Arg Arg Ala Asn Ala Leu Leu Ala Asn Gly Val Glu Leu
    105                 110                 115

AGA GAT AAC CAG CTG GTG GTG CCA TCA GAG GGC CTG TAC CTC ATC TAC        557
```

```
Arg Asp Asn Gln Leu Val Val Pro Ser Glu Gly Leu Tyr Leu Ile Tyr
120                 125                 130                 135

TCC CAG GTC CTC TTC AAG GGC CAA GGC TGC CCC TCC ACC CAT GTG CTC         605
Ser Gln Val Leu Phe Lys Gly Gln Gly Cys Pro Ser Thr His Val Leu
                140                 145                 150

CTC ACC CAC ACC ATC AGC CGC ATC GCC GTC TCC TAC CAG ACC AAG GTC         653
Leu Thr His Thr Ile Ser Arg Ile Ala Val Ser Tyr Gln Thr Lys Val
                155                 160                 165

AAC CTC CTC TCT GCC ATC AAG AGC CCC TGC CAG AGG GAG ACC CCA GAG         701
Asn Leu Leu Ser Ala Ile Lys Ser Pro Cys Gln Arg Glu Thr Pro Glu
                170                 175                 180

GGG GCT GAG GCC AAG CCC TGG TAT GAG CCC ATC TAT CTG GGA GGG GTC         749
Gly Ala Glu Ala Lys Pro Trp Tyr Glu Pro Ile Tyr Leu Gly Gly Val
        185                 190                 195

TTC CAG CTG GAG AAG GGT GAC CGA CTC AGC GCT GAG ATC AAT CGG CCC         797
Phe Gln Leu Glu Lys Gly Asp Arg Leu Ser Ala Glu Ile Asn Arg Pro
200                 205                 210                 215

GAC TAT CTC GAC TTT GCC GAG TCT GGG CAG GTC TAC TTT GGG ATC ATT         845
Asp Tyr Leu Asp Phe Ala Glu Ser Gly Gln Val Tyr Phe Gly Ile Ile
                220                 225                 230

GCC CTG TGAGGAGGAC GAACATCCAA CCTTCCCAAA CGCCTCCCCT GCCCCAATCC          901
Ala Leu

CTTTATTACC CCCTCCTTCA GACACCCTCA ACCTCTTCTG GCTCAAAAAG AGAATTGGGG       961

GCTTAGGGTC GGAACCCAAG CTTAGAACTT TAAGCAACAA GACCACCACT TCGAAACCTG      1021

GGATTCAGGA ATGTGTGGCC TGCACAGTGA ATTGCTGGCA ACCACTAAGA ATTCAAACTG      1081

GGGCCTCCAG AACTCACTGG GGCCTACAGC TTTGATCCCT GACATCTGGA ATCTGGAGAC      1141

CAGGGAGCCT TTGGTTCTGG CCAGAATGCT GCAGGACTTG AGAAGACCTC ACCTAGAAAT      1201

TGACACAAGT GGACCTTAGG CCTTCCTCTC TCCAGATGTT TCCAGACTTC CTTGAGACAC      1261

GGAGCCCAGC CCTCCCCATG GAGCCAGCTC CCTCTATTTA TGTTTGCACT TGTGATTATT      1321

TATTATTTAT TTATTATTTA TTTATTTACA GATGAATGTA TTTATTTGGG AGACCGGGGT      1381

ATCCTGGGGG ACCCAATGTA GGAGCTGCCT TGGCTCAGAC ATGTTTTCCG TGAAAACGGA      1441

GCTGAACAAT AGGCTGTTCC CATGTAGCCC CCTGGCCTCT GTGCCTTCTT TTGATTATGT      1501

TTTTTAAAAT ATTTATCTGA TTAAGTTGTC TAAACAATGC TGATTGGTG ACCAACTGTC       1561

ACTCATTGCT GAGCCTCTGC TCCCCAGGGG AGTTGTGTCT GTAATCGCCC TACTATTCAG      1621

TGGCGAGAAA TAAAGTTTGC TT                                               1643
```

(2) INFORMATION FOR SEQ ID NO:37:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:37:

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60
```

-continued

```
Arg Asp Leu Ser Leu Ile Ser Pro Leu Ala Gln Ala Val Arg Ser Ser
 65              70                  75                  80

Ser Arg Thr Pro Ser Asp Lys Pro Val Ala His Val Val Ala Asn Pro
             85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```